(12) United States Patent
Shluzas

(10) Patent No.: US 8,016,828 B2
(45) Date of Patent: *Sep. 13, 2011

(54) METHODS AND APPARATUSES FOR STABILIZING THE SPINE THROUGH AN ACCESS DEVICE

(75) Inventor: Alan Shluzas, Redwood City, CA (US)

(73) Assignee: Zimmer Spine, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/651,808

(22) Filed: Jan. 4, 2010

(65) Prior Publication Data

US 2011/0009905 A1 Jan. 13, 2011

Related U.S. Application Data

(63) Continuation of application No. 11/527,764, filed on Sep. 26, 2006, now Pat. No. 7,658,739.

(60) Provisional application No. 60/721,580, filed on Sep. 27, 2005.

(51) Int. Cl.
*A61B 17/56* (2006.01)

(52) U.S. Cl. ............ 606/61; 606/250; 606/278

(58) Field of Classification Search ............ 606/60–61, 606/246–265, 278; 623/17.1, 17.3
See application file for complete search history.

(56) References Cited

U.S. PATENT DOCUMENTS

| | | | |
|---|---|---|---|
| 3,789,852 A | 2/1974 | Kim et al. | |
| 4,041,939 A | 8/1977 | Hall | |
| 4,545,374 A | 10/1985 | Jacobson | |
| 4,601,713 A | 7/1986 | Fuqua | |
| 4,697,582 A | 10/1987 | William | |
| 4,716,901 A | 1/1988 | Jackson et al. | |
| 4,743,260 A | 5/1988 | Burton | |
| 4,819,620 A | 4/1989 | Okutsu | |
| 4,863,133 A | 9/1989 | Bonnell | |
| 4,921,478 A | 5/1990 | Solano et al. | |
| 4,984,564 A | 1/1991 | Yuen | |
| 5,024,213 A * | 6/1991 | Asher et al. | 606/278 |
| 5,025,778 A | 6/1991 | Silverstein et al. | |

(Continued)

FOREIGN PATENT DOCUMENTS

EP 0516567 A1 2/1992

(Continued)

OTHER PUBLICATIONS

Davis, Reginald et al., "Dynesys LIS Less Invasive Surgery," Dynamic Stabilization System, Zimmer Spine Inc., 2005.

*Primary Examiner* — Michael A. Brown
(74) *Attorney, Agent, or Firm* — Seager Tufte & Wickhem LLC

(57) ABSTRACT

An apparatus for stabilizing vertebrae while permitting a range of motion therebetween may include first and second fasteners for engaging adjacent vertebrae and a motion preserving device that can be coupled to the first and second fasteners. The motion preserving device may include a longitudinal member that includes an array of load-bearing elements. The longitudinal member may be configured to permit the load-bearing elements to move relative to each other and/or relative to other portions of the member. In some embodiments, the longitudinal member is relatively inflexible along a longitudinal axis and relatively flexible in a direction transverse to the longitudinal axis.

18 Claims, 40 Drawing Sheets

U.S. PATENT DOCUMENTS

| | | |
|---|---|---|
| 5,131,382 A | 7/1992 | Meyer |
| 5,139,499 A | 8/1992 | Small et al. |
| 5,163,949 A | 11/1992 | Bonutti |
| 5,171,279 A | 12/1992 | Mathews |
| 5,176,708 A | 1/1993 | Frey et al. |
| 5,190,561 A | 3/1993 | Graber |
| 5,195,541 A | 3/1993 | Obenchain |
| 5,197,971 A | 3/1993 | Bonutti |
| 5,224,680 A | 7/1993 | Greenstein et al. |
| 5,287,845 A | 2/1994 | Faul et al. |
| 5,295,994 A | 3/1994 | Bonutti |
| 5,312,417 A | 5/1994 | Wilk |
| 5,345,927 A | 9/1994 | Bonutti |
| 5,354,302 A | 10/1994 | Ko |
| 5,370,647 A | 12/1994 | Graber et al. |
| 5,375,823 A | 12/1994 | Navas |
| 5,395,317 A | 3/1995 | Kambin |
| 5,437,669 A * | 8/1995 | Yuan et al. ............ 606/278 |
| 5,439,464 A | 8/1995 | Shapiro |
| 5,464,365 A | 11/1995 | Kirn |
| 5,472,426 A | 12/1995 | Bonati et al. |
| 5,484,437 A | 1/1996 | Michelson |
| 5,489,307 A | 2/1996 | Kuslich et al. |
| 5,520,607 A | 5/1996 | Frassica et al. |
| 5,540,688 A | 7/1996 | Navas |
| 5,562,660 A | 10/1996 | Grob |
| 5,571,072 A | 11/1996 | Kronner |
| 5,575,754 A | 11/1996 | Konomura |
| 5,601,590 A | 2/1997 | Bonutti et al. |
| 5,667,520 A | 9/1997 | Bonutti |
| 5,707,359 A | 1/1998 | Bufalini |
| 5,725,582 A | 3/1998 | Bevan et al. |
| 5,782,531 A | 7/1998 | Shindle |
| 5,792,044 A | 8/1998 | Foley et al. |
| 5,795,289 A | 8/1998 | Wyttenbach |
| 5,827,319 A | 10/1998 | Carlson et al. |
| RE36,221 E | 6/1999 | Breard et al. |
| 5,954,635 A | 9/1999 | Foley et al. |
| 5,961,499 A | 10/1999 | Bonutti et al. |
| 5,961,516 A | 10/1999 | Graf |
| 5,997,508 A | 12/1999 | Lunn et al. |
| 6,036,693 A | 3/2000 | Yuan et al. |
| 6,080,156 A | 6/2000 | Asher et al. |
| 6,083,224 A | 7/2000 | Gertzbein et al. |
| 6,120,437 A | 9/2000 | Yoon et al. |
| 6,162,236 A | 12/2000 | Osada |
| 6,171,299 B1 | 1/2001 | Bonutti |
| 6,187,000 B1 | 2/2001 | Davison et al. |
| 6,193,715 B1 | 2/2001 | Wrublewski et al. |
| 6,214,005 B1 * | 4/2001 | Benzel et al. ............ 606/250 |
| 6,241,730 B1 | 6/2001 | Alby |
| 6,248,106 B1 | 6/2001 | Ferree |
| 6,267,764 B1 | 7/2001 | Elberg |
| 6,290,700 B1 | 9/2001 | Schmotzer |
| 6,306,137 B2 | 10/2001 | Troxell |
| 6,306,170 B2 | 10/2001 | Ray |
| 6,312,443 B1 | 11/2001 | Stone |
| 6,338,730 B1 | 1/2002 | Bonutti et al. |
| 6,358,226 B1 | 3/2002 | Ryan |
| 6,358,266 B1 | 3/2002 | Bonutti |
| 6,361,488 B1 | 3/2002 | Davison et al. |
| 6,371,968 B1 | 4/2002 | Kogasaka et al. |
| 6,383,195 B1 | 5/2002 | Richard |
| 6,440,169 B1 | 8/2002 | Elberg et al. |
| 6,494,893 B2 | 12/2002 | Dubrul et al. |
| 6,497,654 B1 | 12/2002 | Leonard et al. |
| 6,524,320 B2 | 2/2003 | DiPoto |
| 6,530,880 B2 | 3/2003 | Pagliuca |
| 6,530,926 B1 | 3/2003 | Davison |
| 6,564,078 B1 | 5/2003 | Marino et al. |
| 6,610,079 B1 | 8/2003 | Li et al. |
| 6,645,207 B2 | 11/2003 | Dixon et al. |
| 6,761,719 B2 | 7/2004 | Justis et al. |
| 6,783,527 B2 | 8/2004 | Drewry et al. |
| 6,800,084 B2 | 10/2004 | Davison et al. |
| 6,802,844 B2 | 10/2004 | Ferree |
| 6,821,243 B2 | 11/2004 | Pagliuca et al. |
| 6,837,889 B2 | 1/2005 | Shluzas |
| 6,986,771 B2 | 1/2006 | Paul et al. |
| 6,989,011 B2 | 1/2006 | Paul et al. |
| 7,004,947 B2 | 2/2006 | Shluzas et al. |
| 7,008,424 B2 | 3/2006 | Teitelbaum |
| 7,029,475 B2 | 4/2006 | Panjabi |
| 7,056,321 B2 | 6/2006 | Pagliuca et al. |
| 7,066,937 B2 | 6/2006 | Shluzas |
| 7,137,985 B2 | 11/2006 | Jahng |
| 7,144,393 B2 | 12/2006 | DiPoto et al. |
| 7,144,396 B2 | 12/2006 | Shluzas |
| 7,226,451 B2 | 6/2007 | Shluzas et al. |
| 7,326,210 B2 | 2/2008 | Jahng et al. |
| 7,641,673 B2 | 1/2010 | Le Couedic et al. |
| 2001/0011170 A1 | 8/2001 | Davison et al. |
| 2001/0037111 A1 | 11/2001 | Dixon et al. |
| 2001/0049498 A1 | 12/2001 | Davison et al. |
| 2002/0002360 A1 | 1/2002 | Orth et al. |
| 2002/0013586 A1 | 1/2002 | Justis et al. |
| 2002/0035366 A1 | 3/2002 | Walder et al. |
| 2002/0052603 A1 | 5/2002 | Nichols et al. |
| 2002/0120269 A1 | 8/2002 | Lange |
| 2002/0120270 A1 | 8/2002 | Trieu et al. |
| 2003/0009130 A1 | 1/2003 | Stecker et al. |
| 2003/0014068 A1 | 1/2003 | Bonutti et al. |
| 2003/0040656 A1 | 2/2003 | Pagliuca et al. |
| 2003/0073998 A1 | 4/2003 | Pagliuca et al. |
| 2003/0083657 A1 | 5/2003 | Drewry et al. |
| 2003/0139648 A1 | 7/2003 | Foley et al. |
| 2003/0153927 A1 | 8/2003 | DiPoto et al. |
| 2003/0191371 A1 | 10/2003 | Smith et al. |
| 2003/0195405 A1 | 10/2003 | Marino et al. |
| 2003/0195493 A1 | 10/2003 | Davison et al. |
| 2003/0195549 A1 | 10/2003 | Davison et al. |
| 2003/0195550 A1 | 10/2003 | Davison et al. |
| 2003/0195551 A1 | 10/2003 | Davison et al. |
| 2003/0199871 A1 | 10/2003 | Foley et al. |
| 2003/0199884 A1 | 10/2003 | Davison et al. |
| 2003/0199885 A1 | 10/2003 | Davison et al. |
| 2003/0220643 A1 | 11/2003 | Ferree |
| 2004/0049189 A1 | 3/2004 | Le Couedic et al. |
| 2004/0215191 A1 | 10/2004 | Kitchen |
| 2004/0225289 A1 | 11/2004 | Biedermann et al. |
| 2005/0010220 A1 | 1/2005 | Casutt et al. |
| 2005/0056979 A1 | 3/2005 | Studer et al. |
| 2005/0065416 A1 | 3/2005 | Subotics |
| 2005/0065515 A1 | 3/2005 | Jahng |
| 2005/0065516 A1 | 3/2005 | Jahng |
| 2005/0085815 A1 | 4/2005 | Harms et al. |
| 2005/0090822 A1 * | 4/2005 | DiPoto ............ 606/61 |
| 2005/0096652 A1 | 5/2005 | Burton |
| 2005/0124991 A1 | 6/2005 | Jahng |
| 2005/0143737 A1 | 6/2005 | Pafford et al. |
| 2005/0154390 A1 | 7/2005 | Biedermann et al. |
| 2005/0177157 A1 | 8/2005 | Jahng |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203517 A1 | 9/2005 | Jahng et al. |
| 2005/0277922 A1 | 12/2005 | Trieu et al. |
| 2006/0106380 A1 | 5/2006 | Colleran et al. |
| 2006/0106381 A1 | 5/2006 | Ferree et al. |
| 2006/0111715 A1 | 5/2006 | Jackson |
| 2006/0142758 A1 | 6/2006 | Petit |
| 2006/0149238 A1 | 7/2006 | Sherman et al. |
| 2006/0173454 A1 | 8/2006 | Spitler et al. |
| 2006/0195093 A1 | 8/2006 | Jahng |
| 2006/0200129 A1 | 9/2006 | Denti |
| 2006/0212033 A1 | 9/2006 | Rothman et al. |
| 2006/0229615 A1 | 10/2006 | Abdou |
| 2006/0247638 A1 | 11/2006 | Trieu et al. |
| 2006/0264937 A1 | 11/2006 | White |
| 2007/0005062 A1 | 1/2007 | Lange et al. |
| 2007/0005063 A1 | 1/2007 | Bruneau et al. |
| 2007/0016200 A1 | 1/2007 | Jackson |
| 2007/0021750 A1 | 1/2007 | Shluzas et al. |
| 2007/0055244 A1 | 3/2007 | Jackson |
| 2007/0078461 A1 | 4/2007 | Shluzas |
| 2007/0100341 A1 | 5/2007 | Reglos et al. |
| 2007/0118119 A1 | 5/2007 | Hestad |

| | | | |
|---|---|---|---|
| 2007/0129729 A1 | 6/2007 | Petit et al. | |
| 2007/0198088 A1 | 8/2007 | Biedermann et al. | |
| 2007/0225710 A1 | 9/2007 | Jahng et al. | |
| 2007/0233075 A1 | 10/2007 | Dawson | |
| 2007/0233087 A1 | 10/2007 | Schlapfer | |
| 2007/0233095 A1 | 10/2007 | Schlaepfer | |
| 2007/0239158 A1 | 10/2007 | Trieu et al. | |
| 2007/0270814 A1 | 11/2007 | Lim et al. | |
| 2007/0270821 A1 | 11/2007 | Trieu et al. | |
| 2007/0270837 A1 | 11/2007 | Eckhardt et al. | |
| 2007/0270838 A1 | 11/2007 | Bruneau et al. | |
| 2007/0270860 A1 | 11/2007 | Jackson | |
| 2007/0293862 A1 | 12/2007 | Jackson | |
| 2008/0009863 A1 | 1/2008 | Bond et al. | |
| 2008/0021459 A1 | 1/2008 | Lim | |
| 2008/0021465 A1 | 1/2008 | Shadduck et al. | |
| 2008/0039483 A1 | 2/2008 | Salama | |
| 2008/0039843 A1 | 2/2008 | Abdou | |
| 2008/0051787 A1 | 2/2008 | Remington et al. | |
| 2008/0091213 A1 | 4/2008 | Jackson | |
| 2008/0140076 A1 | 6/2008 | Jackson | |
| 2008/0140133 A1 | 6/2008 | Allard et al. | |
| 2008/0147122 A1 | 6/2008 | Jackson | |
| 2008/0161857 A1 | 7/2008 | Hestad et al. | |
| 2008/0172091 A1 | 7/2008 | Anderson | |
| 2008/0177317 A1 | 7/2008 | Jackson | |
| 2008/0183216 A1 | 7/2008 | Jackson | |
| 2008/0195153 A1 | 8/2008 | Thompson | |
| 2008/0234737 A1 | 9/2008 | Boschert | |
| 2008/0234738 A1 | 9/2008 | Zylber et al. | |
| 2008/0234744 A1 | 9/2008 | Zylber et al. | |
| 2008/0262551 A1 | 10/2008 | Rice et al. | |
| 2008/0275456 A1 | 11/2008 | Vonwiller et al. | |
| 2008/0294198 A1 | 11/2008 | Jackson | |
| 2008/0300633 A1 | 12/2008 | Jackson | |
| 2008/0319486 A1 | 12/2008 | Hestad et al. | |
| 2009/0005817 A1 | 1/2009 | Friedrich et al. | |
| 2009/0012562 A1 | 1/2009 | Hestad et al. | |
| 2009/0030464 A1 | 1/2009 | Hestad et al. | |
| 2009/0036924 A1 | 2/2009 | Egli et al. | |
| 2009/0082815 A1 | 3/2009 | Zylber et al. | |
| 2009/0093845 A1 | 4/2009 | Hestad et al. | |
| 2009/0093846 A1 | 4/2009 | Hestad | |
| 2009/0099606 A1 | 4/2009 | Hestad et al. | |
| 2009/0112265 A1 | 4/2009 | Hudgins et al. | |
| 2009/0118767 A1 | 5/2009 | Hestad et al. | |
| 2009/0198281 A1 | 8/2009 | Rice et al. | |
| 2009/0216281 A1 | 8/2009 | Vonwiller et al. | |

FOREIGN PATENT DOCUMENTS

| | | |
|---|---|---|
| EP | 0528562 A2 | 2/1993 |
| EP | 0669109 A1 | 8/1995 |
| EP | 0807415 A2 | 11/1997 |
| EP | 0807415 A3 | 8/1998 |
| EP | 0669109 B1 | 5/1999 |
| EP | 0980677 A1 | 2/2000 |
| EP | 1305077 A1 | 5/2003 |
| EP | 1523949 A1 | 4/2005 |
| EP | 1719468 A1 | 11/2006 |
| EP | 1523949 B1 | 6/2007 |
| FR | 2715057 A1 | 7/1995 |
| FR | 2775583 A1 | 9/1999 |
| FR | 2844180 A1 | 3/2004 |
| FR | 2867057 A1 | 9/2005 |
| JP | 2000-083960 A2 | 3/2000 |
| JP | 2001-149376 A2 | 6/2001 |
| NL | 7610576 A | 3/1978 |
| WO | 9221292 A2 | 12/1992 |
| WO | 9314801 | 8/1993 |
| WO | 9403114 | 2/1994 |
| WO | 9510218 A1 | 4/1995 |
| WO | 9519149 A1 | 7/1995 |
| WO | 9532663 | 12/1995 |
| WO | 9905980 A1 | 2/1999 |
| WO | 9940866 A1 | 8/1999 |
| WO | 9944527 A1 | 9/1999 |
| WO | 0154560 A2 | 8/2001 |
| WO | 0209801 A1 | 2/2002 |
| WO | 02078767 A2 | 10/2002 |
| WO | 03007783 A2 | 1/2003 |
| WO | 2004024011 A1 | 3/2004 |
| WO | 2004089244 A2 | 10/2004 |
| WO | 2005037110 A2 | 10/2004 |
| WO | 2005037150 A1 | 10/2004 |
| WO | 2005087121 A1 | 3/2005 |
| WO | 2006066685 A1 | 6/2006 |
| WO | 2007087476 A1 | 1/2007 |
| WO | 2007038429 A1 | 4/2007 |
| WO | 2007044795 A2 | 4/2007 |
| WO | 2008006098 A2 | 1/2008 |
| WO | 2008013892 A2 | 1/2008 |
| WO | 2008021319 A2 | 2/2008 |
| WO | 2008034130 A2 | 3/2008 |
| WO | 2008134703 A2 | 11/2008 |

* cited by examiner

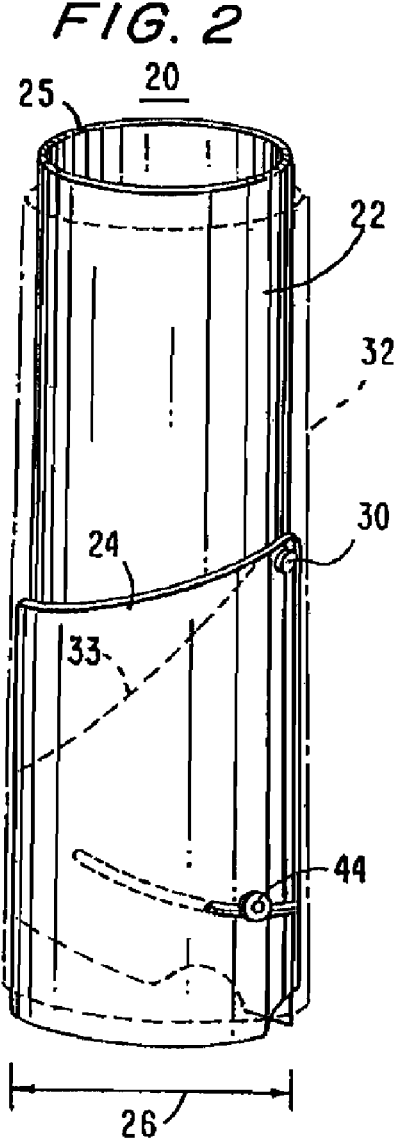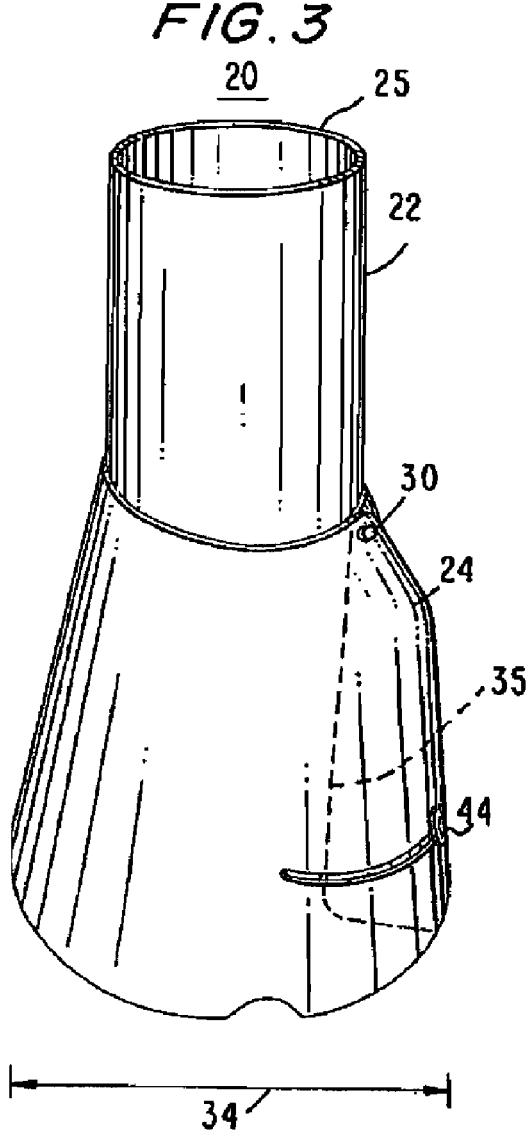

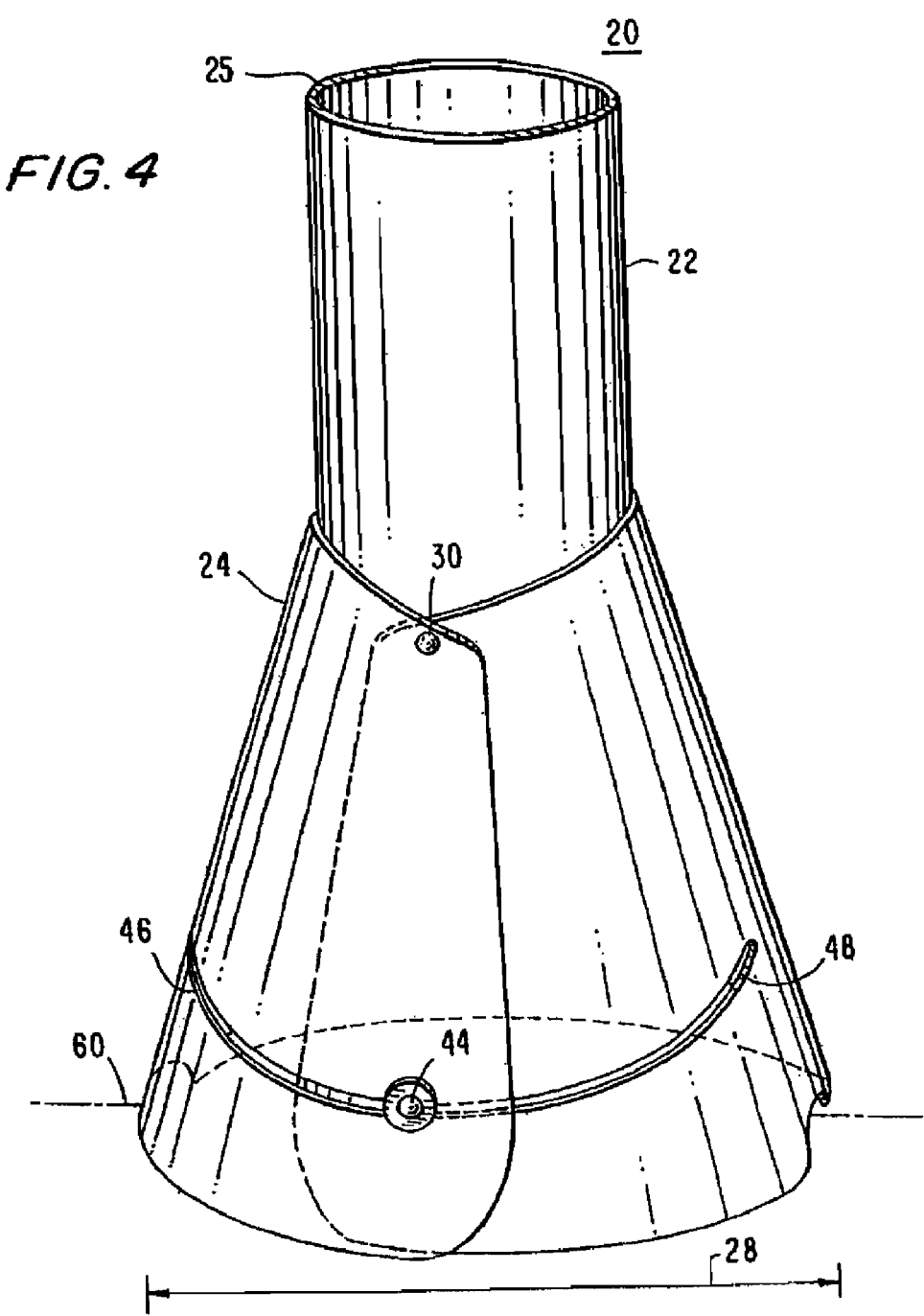

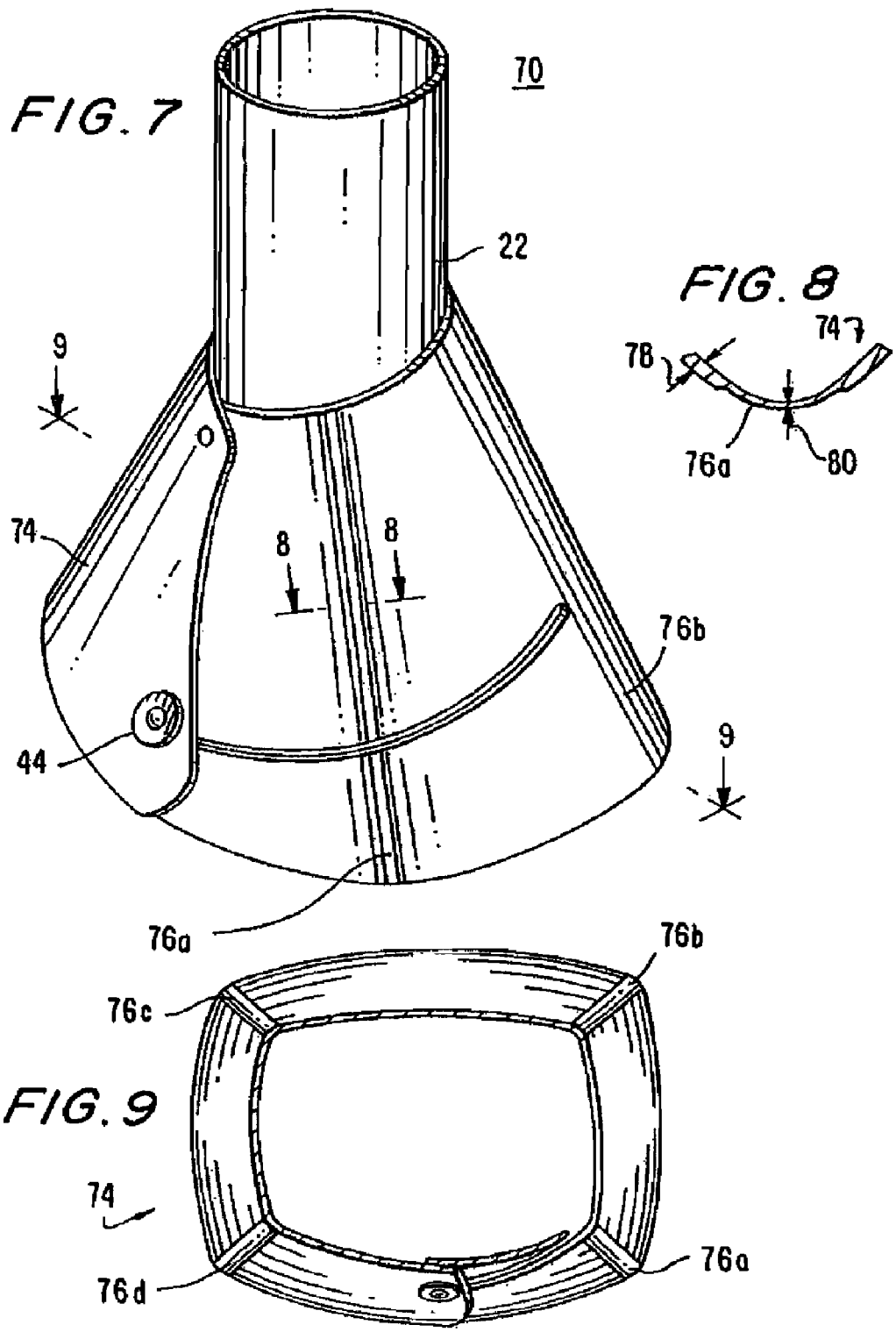

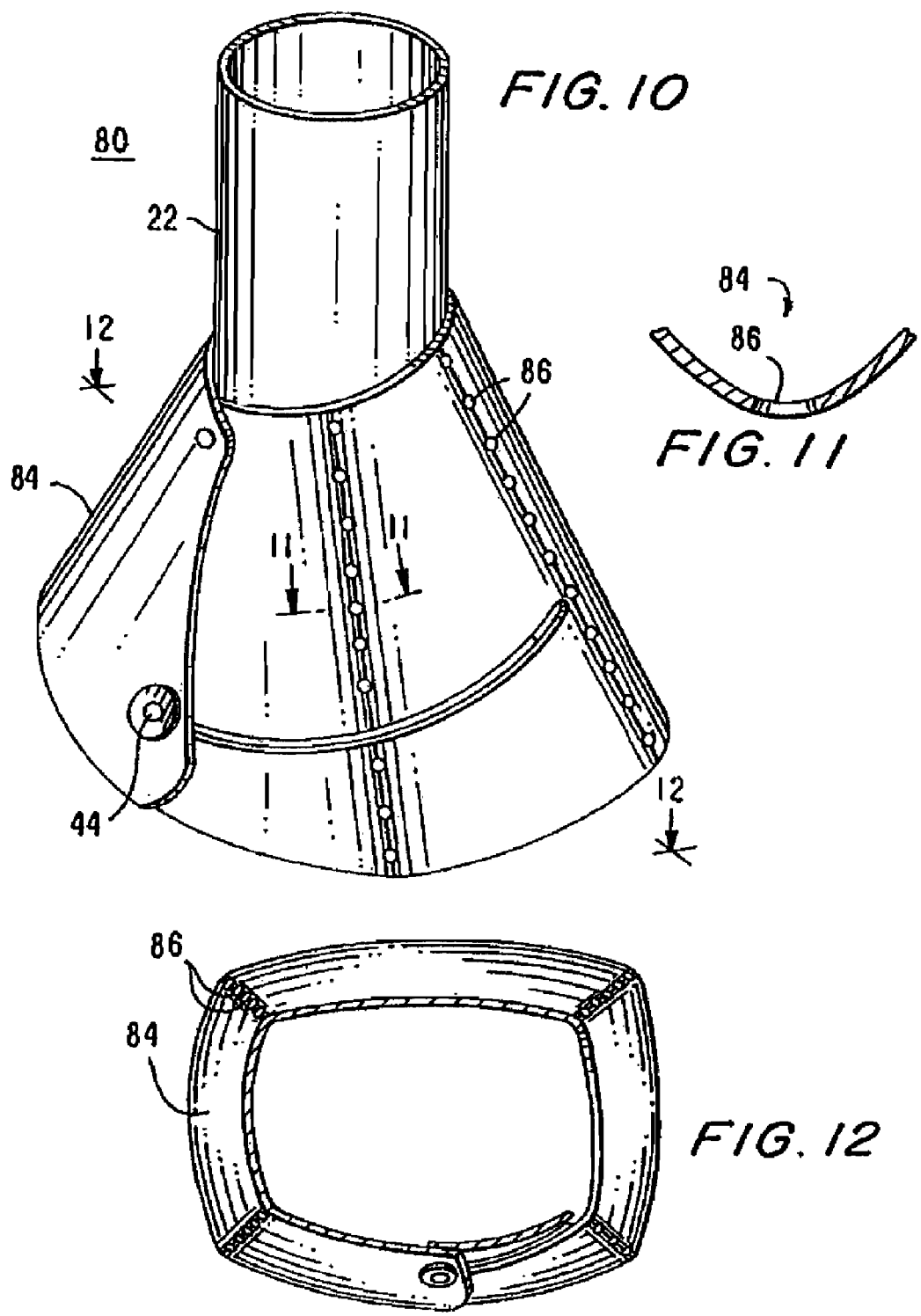

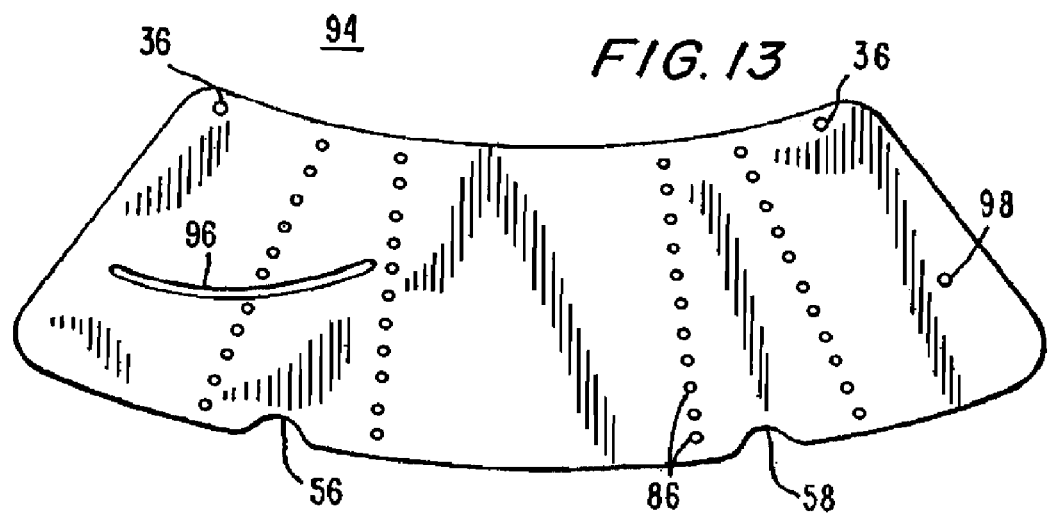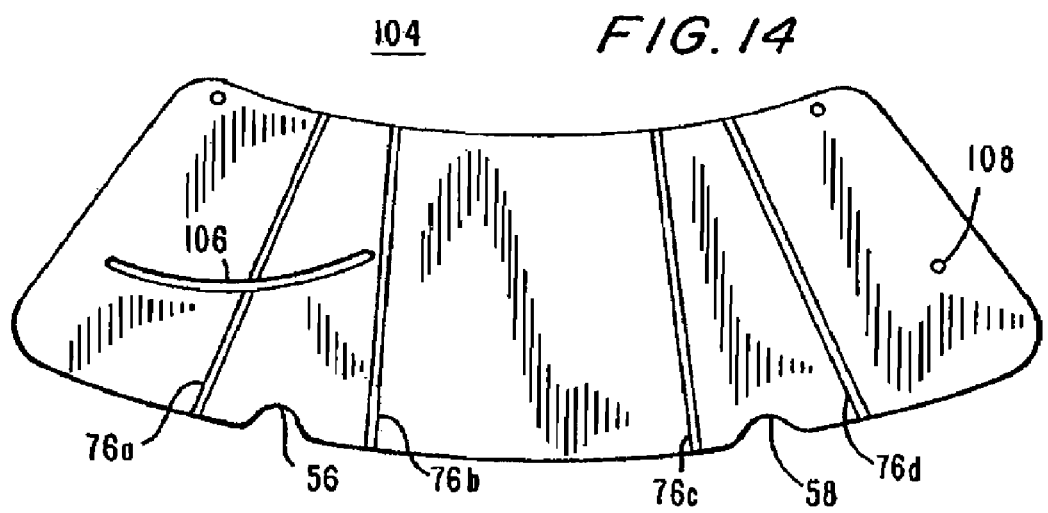

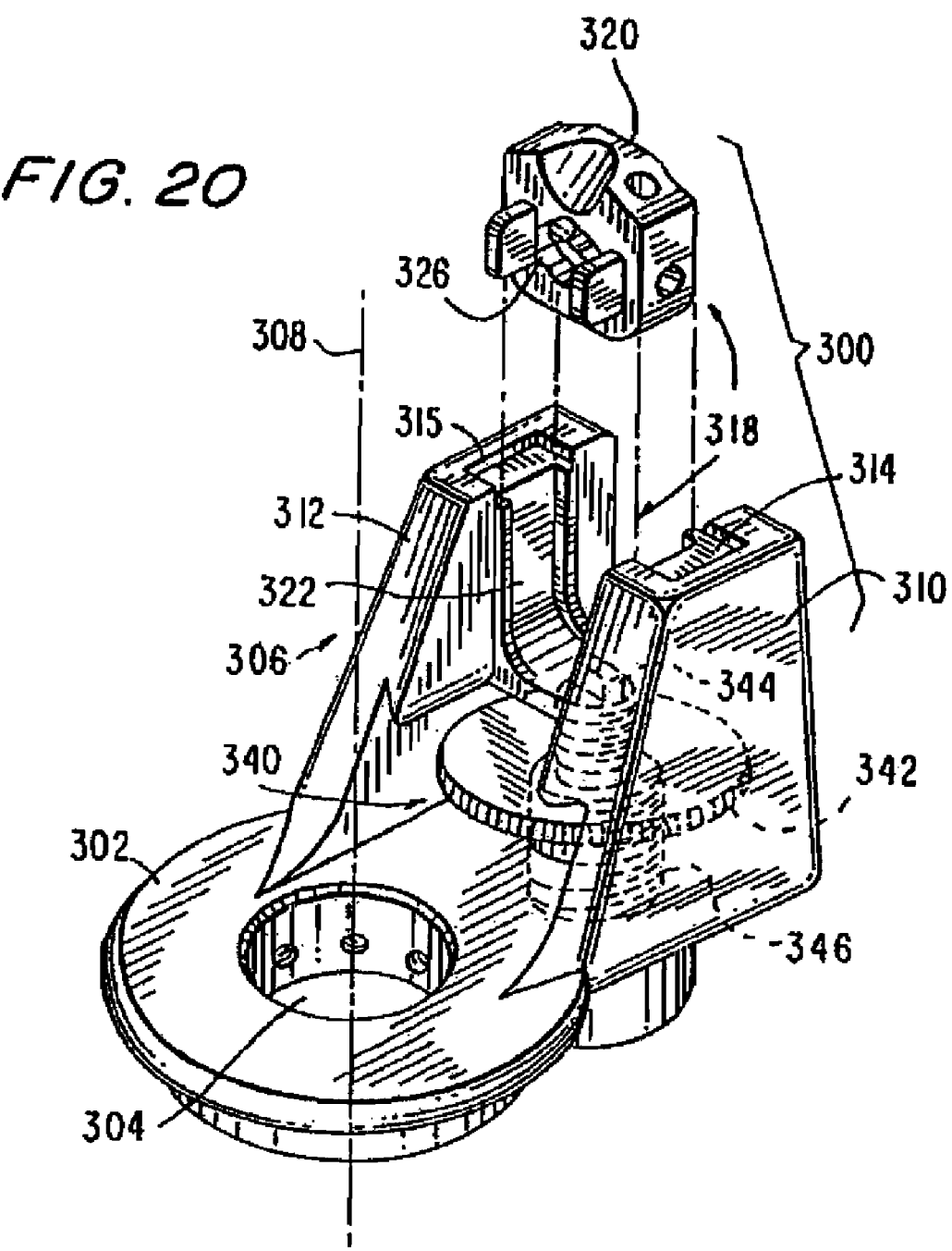

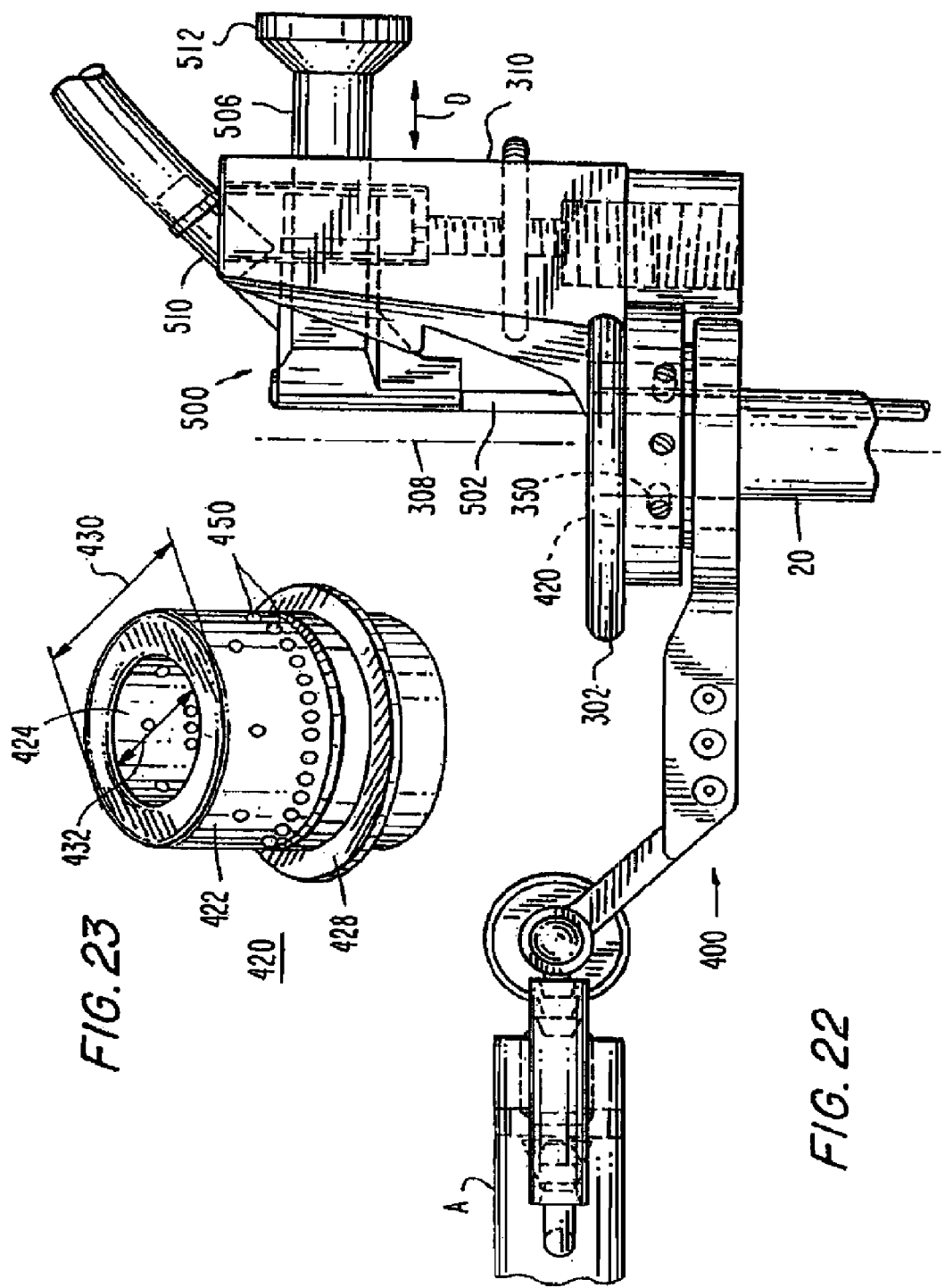

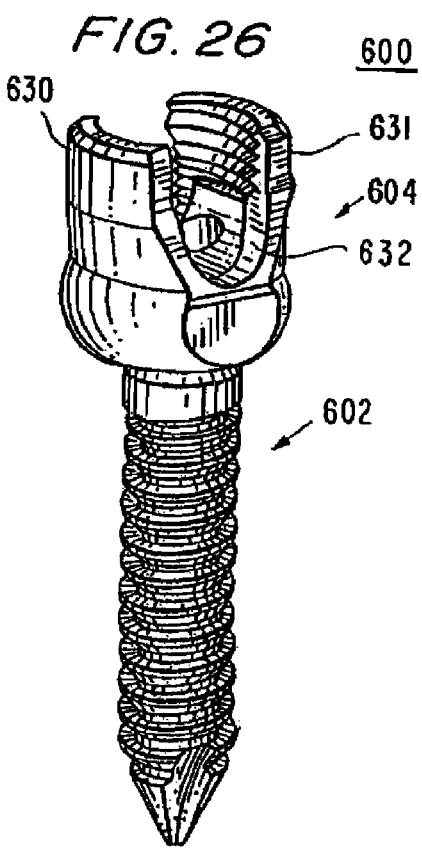
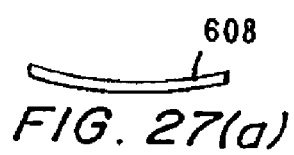
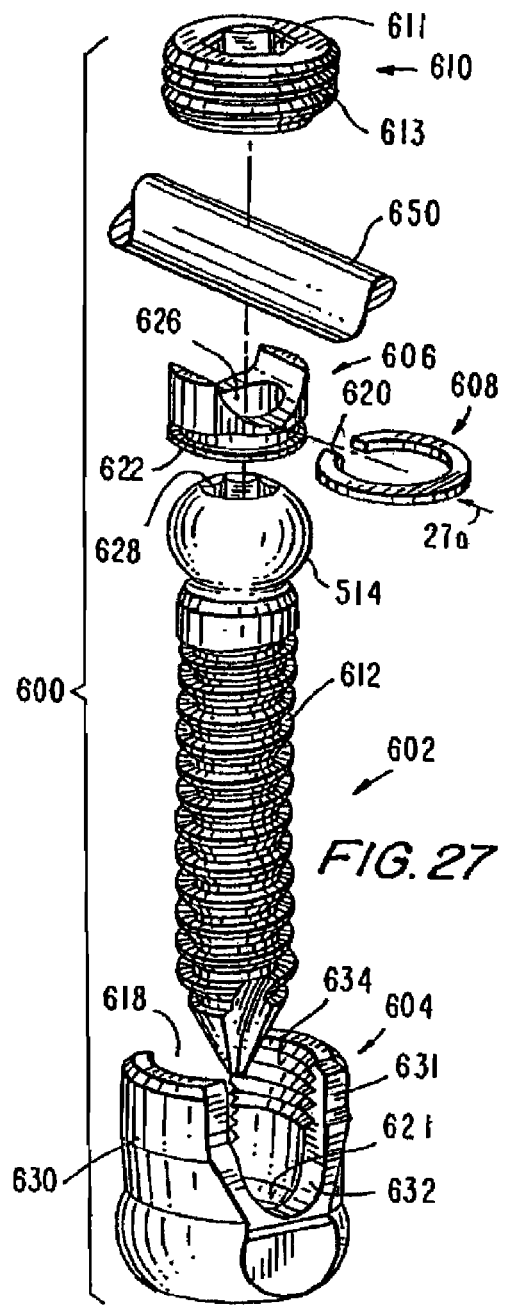

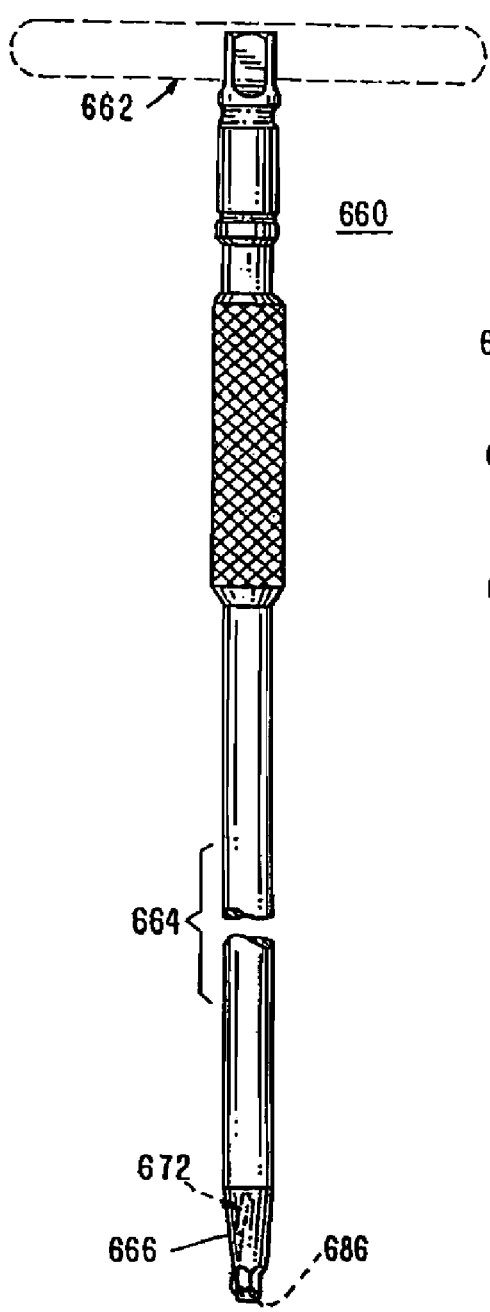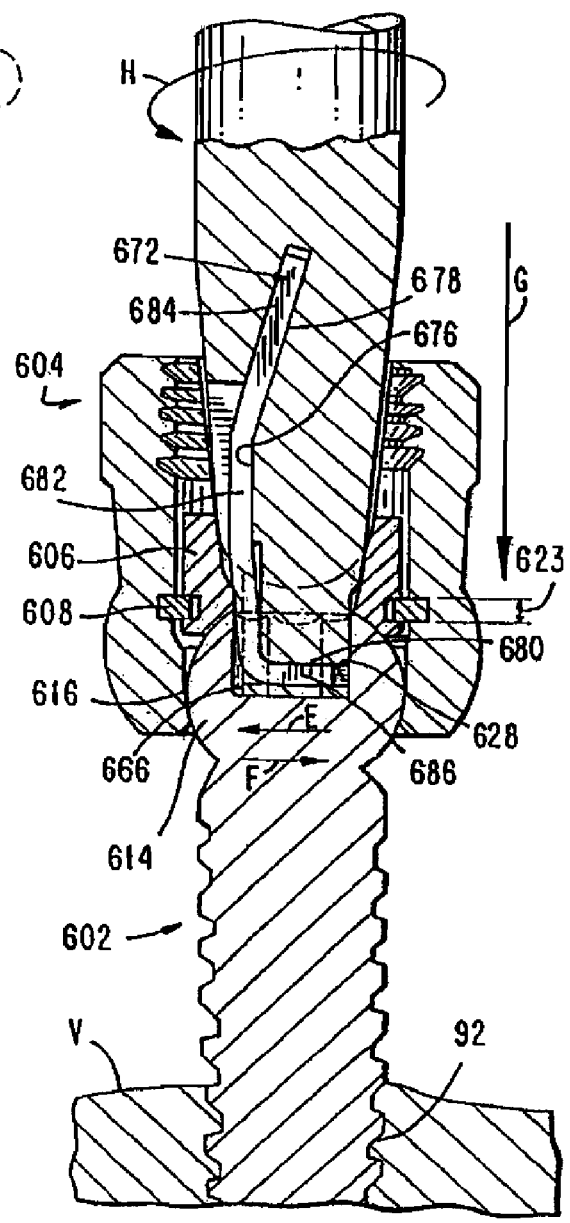

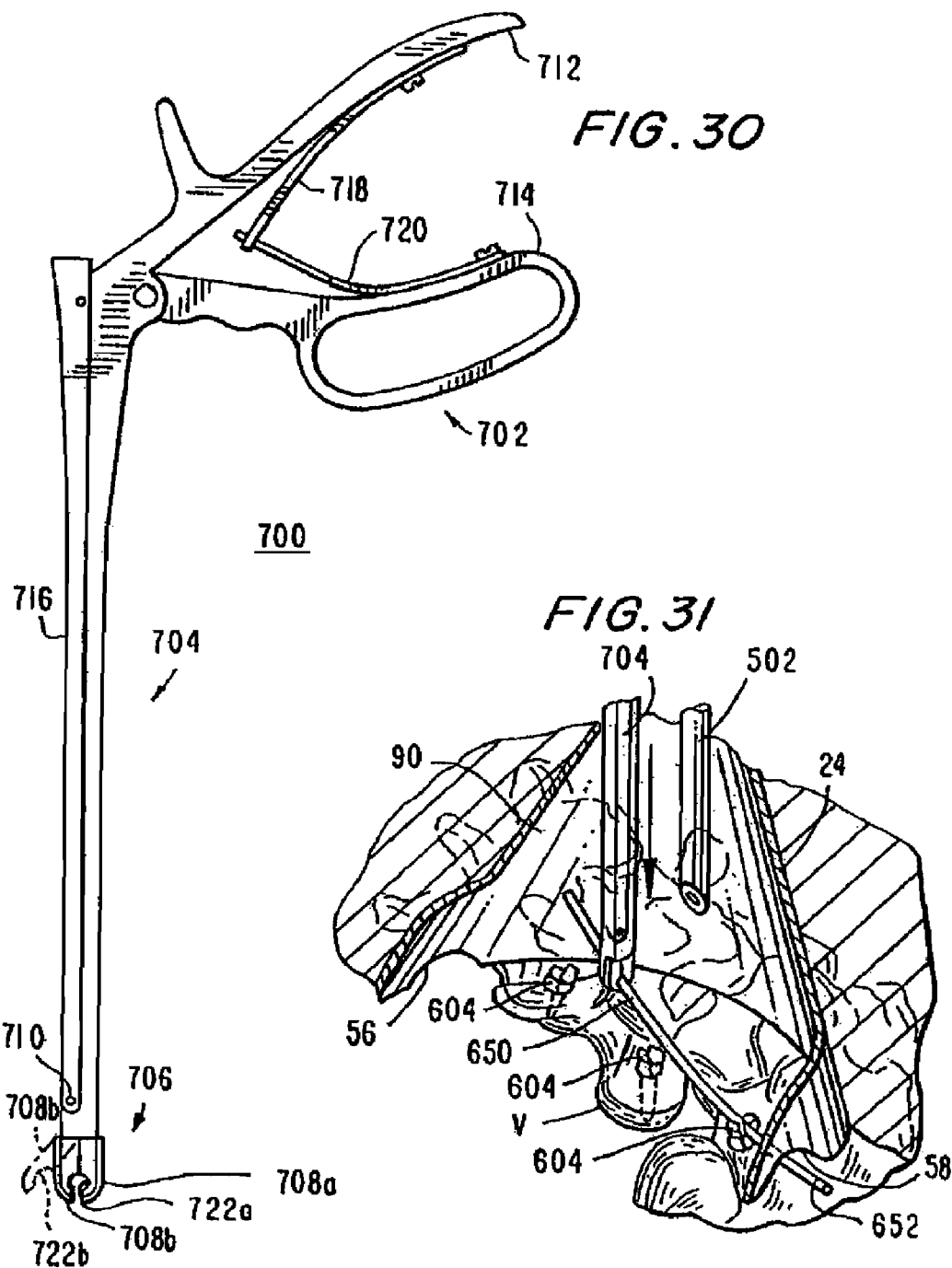

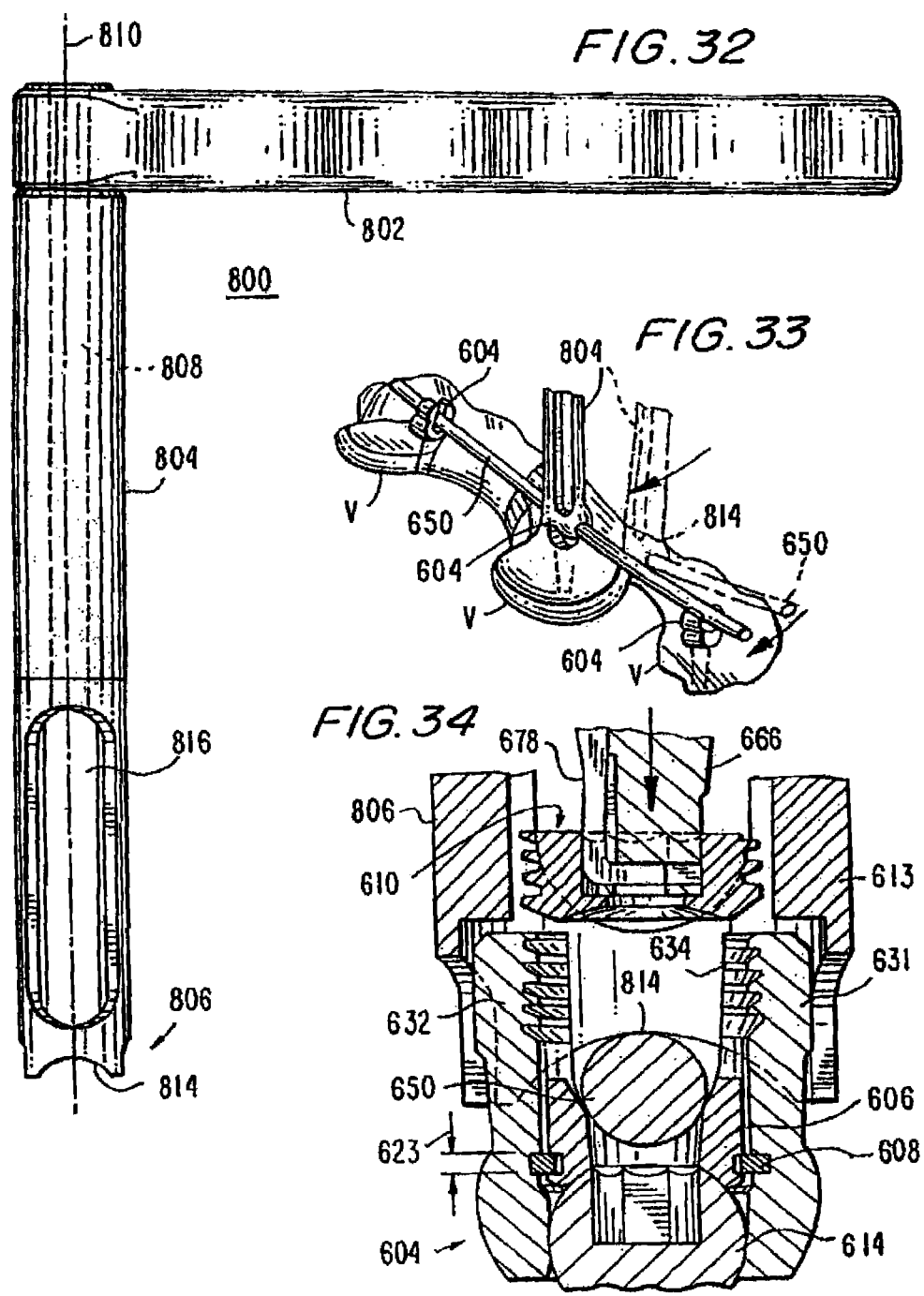

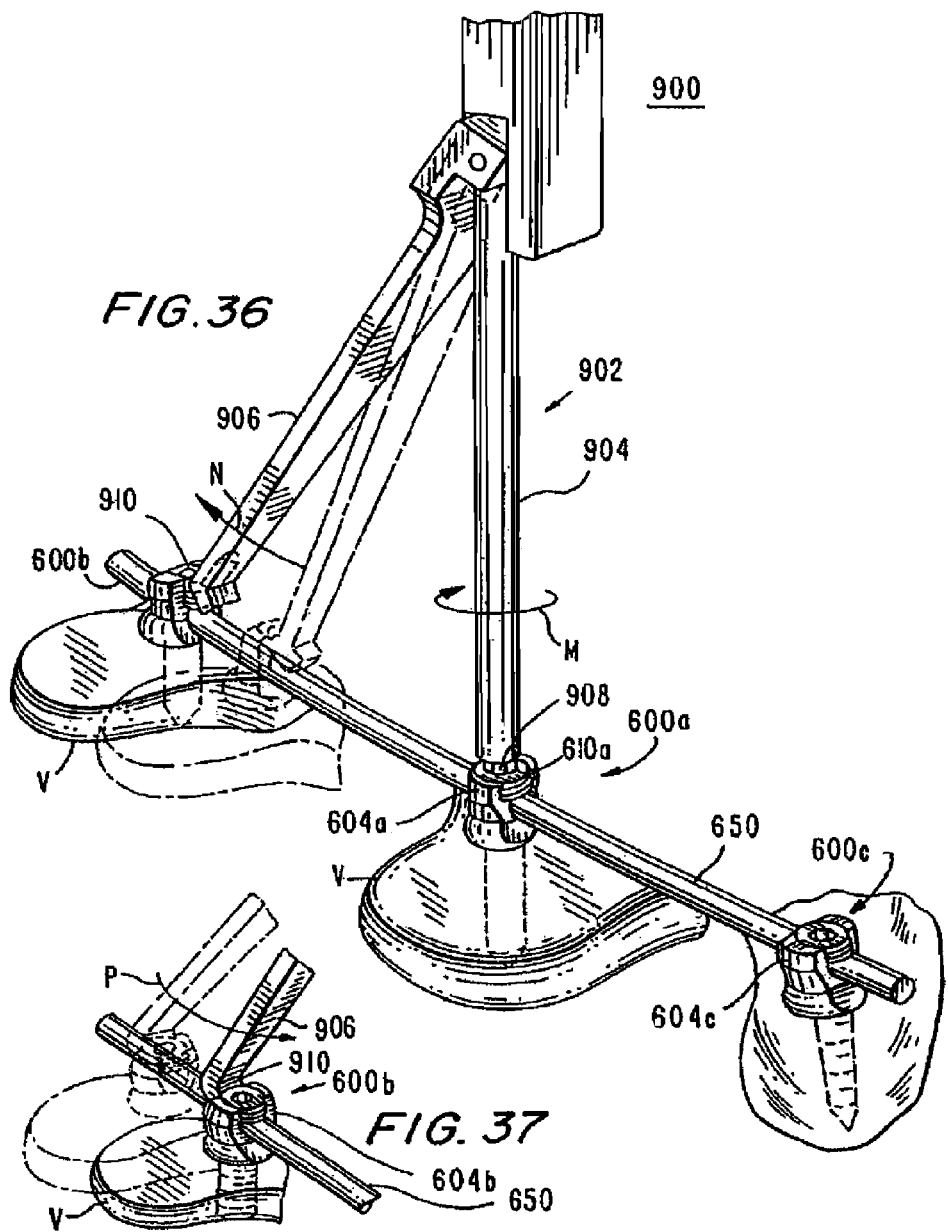

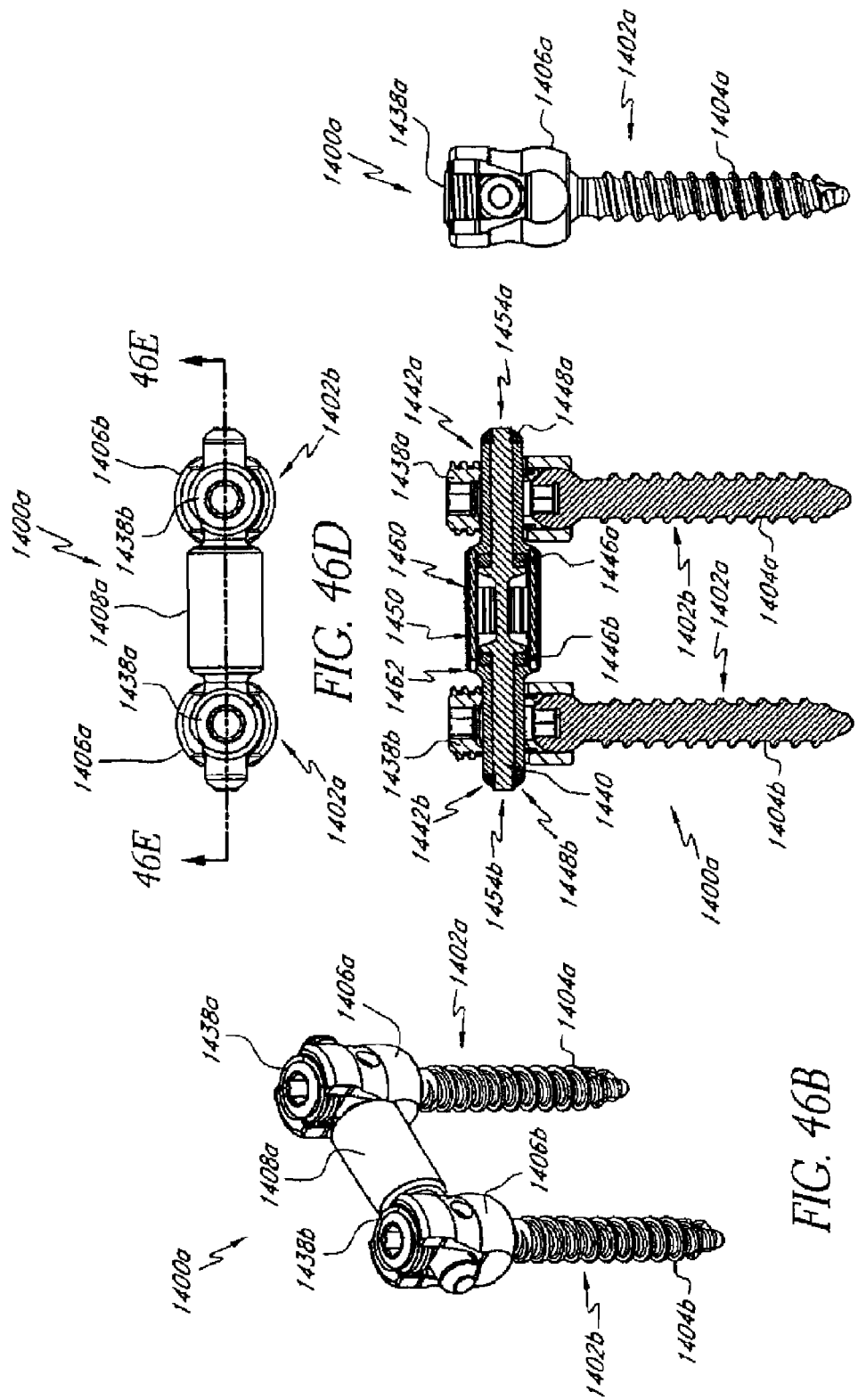

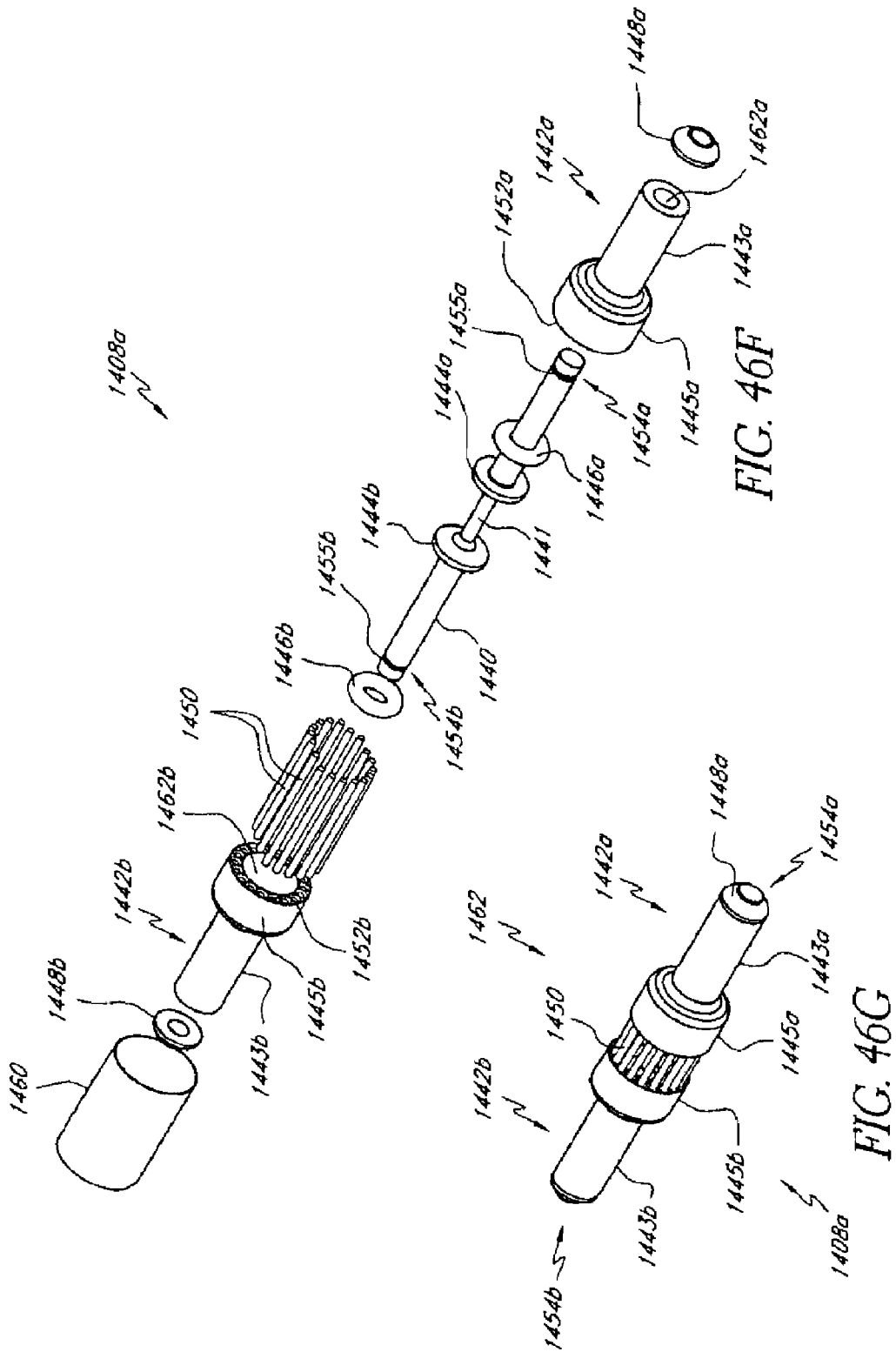

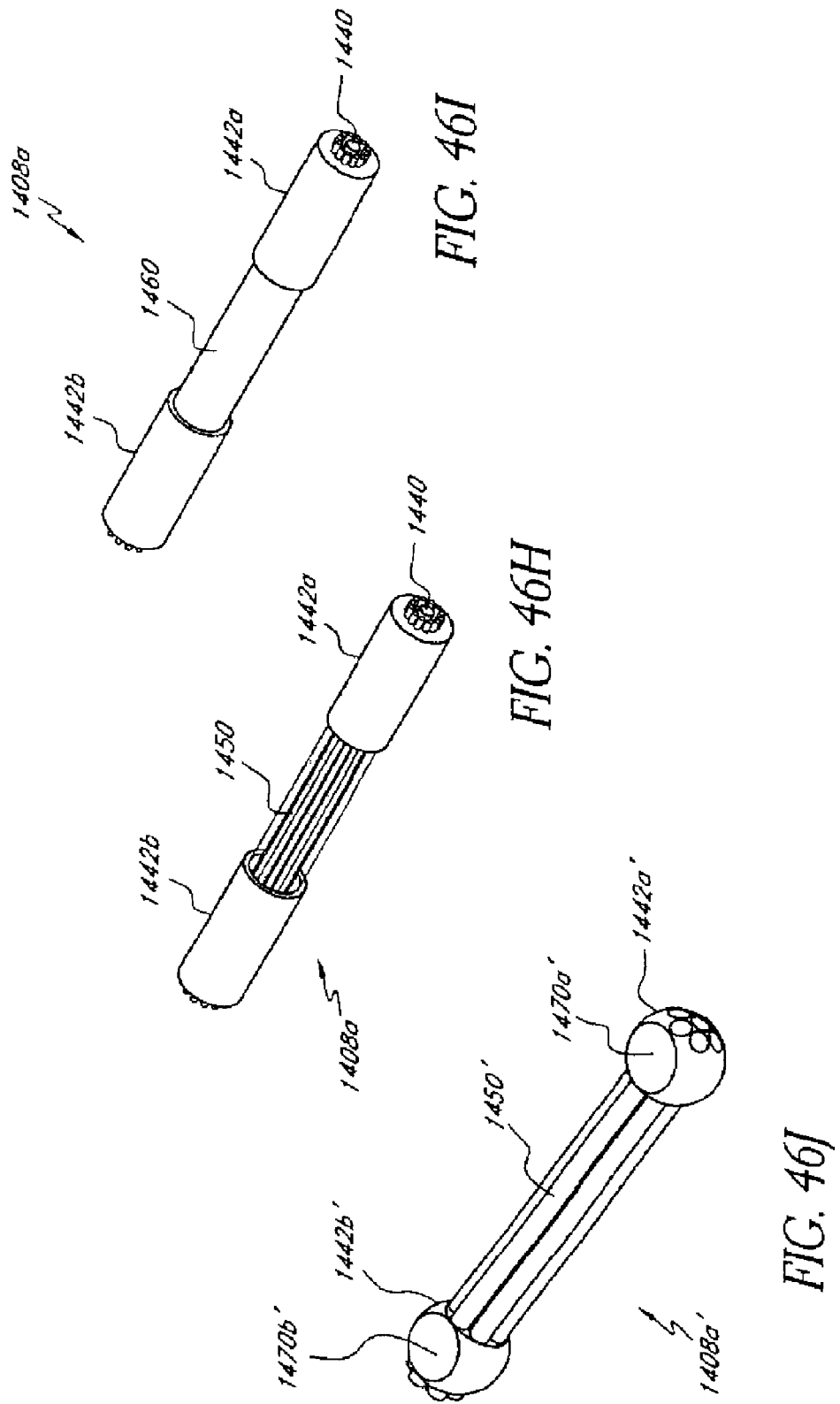

METHODS AND APPARATUSES FOR STABILIZING THE SPINE THROUGH AN ACCESS DEVICE

RELATED APPLICATION

This application is a continuation of U.S. patent application Ser. No. 11/527,764, filed on Sep. 26, 2006, now U.S. Pat. No. 7,658,739, which claims the benefit under 35 U.S.C. §119(e) of U.S. Provisional Patent Application No. 60/721,580, filed on Sep. 27, 2005, entitled "METHODS AND APPARATUSES FOR STABILIZING THE SPINE THROUGH AN ACCESS DEVICE," which are hereby incorporated by reference herein in their entirety.

BACKGROUND OF THE DISCLOSURE

1. Field of the Disclosure

This application relates generally to methods and apparatuses for performing minimally invasive surgery, and more particularly to methods and apparatuses for performing procedures for stabilizing adjacent bones while preserving motion therebetween.

2. Description of the Related Art

In the past, patients suffering from degenerative spine conditions, such as progressive degeneration of intervertebral discs, have been treated by various techniques. For example, fixation and fusion are two procedures that are sometimes performed in combination to address degeneration of the intervertebral discs. Fusion involves the replacement of an intervertebral disc with a bone graft intended to fuse the adjacent vertebrae together. Fixation provides an external structure that bridges from one vertebra to an adjacent vertebra to eliminate motion therebetween. While fusion and fixation may reduce some symptoms of disc degeneration, the elimination of motion reduces the patient's flexibility and may cause other complications.

Also, these procedures are typically performed by way of open spine surgery. In open spine surgery, the surgeon typically makes large incisions and cuts or strips muscle tissue surrounding the spine to provide open access to the troubled area. This technique exposes nerves in the open area, which can be injured when exposed. Consequently, open surgery carries significant risks of scarring, pain, nerve damage, and blood loss. Open surgery also subjects patients to extended recovery times.

Less invasive techniques have been proposed to reduce the trauma of open spine surgery. For example, a constant diameter cannula has been proposed to reduce incision length associated with open surgery. Unfortunately, such cannulae are usually very narrow and therefore they provide minimal space for the physician to observe the body structures and manipulate surgical instruments.

SUMMARY OF THE DISCLOSURE

Accordingly, there is a need in the art for minimally invasive systems and methods for stabilizing adjacent bone, e.g., vertebrae, while preserving motion therebetween. These systems and methods may advantageously provide a more normal post-recovery range of motion, and may also limit stresses associated with other stabilization procedures placed on adjacent vertebrae and intervening discs.

One embodiment of the stabilization system comprises an apparatus for retaining a vertebrae of a spinal column in a desired spatial relationship. The apparatus comprises a first fastener that has a threaded shank and an enlarged head. The threaded shank of the first fastener engages a portion of a vertebra in use. The apparatus has a first housing having a first passage and a second passage having a longitudinal axis extending transverse to the first passage. The first fastener extends through an opening in the first housing into the second passage. The apparatus comprises a second fastener having a threaded shank and an enlarged head. The threaded shank of the second fastener engages a portion of a vertebra in use. The apparatus has a second housing that has a first passage and a second passage having a longitudinal axis extending transverse to the first passage. The second fastener extends through an opening in the second housing into the second passage. A longitudinal member having a first end and a second end and comprising a plurality of thin sheets is configured to extend between the first and second housings. A first clamping device is coupled with the first housing and is configured to secure the first end of the longitudinal member to the first housing. A second clamping device is coupled with the second housing and is configured to secure the second end of the longitudinal member to the second housing while allowing the thin sheets to slide relative to each other and relative to the second housing.

In another form, a method of stabilizing at least two vertebrae of the spine of a patient is provided. The method comprises coupling a first screw with a vertebra, the first screw having a first housing. A second screw having a second housing is coupled with another vertebra. A first end of a multi-layered longitudinal member is secured with the first screw. A second end of the multi-layered longitudinal member is secured with the second screw while allowing relative motion between the layers of the longitudinal member. In one variation, the first end is clamped with the first screw, substantially preventing relative motion between the layers of the longitudinal member at the first end.

In other techniques, a first cap screw is secured onto the first end of the longitudinal member to secure the longitudinal member in the first housing. A second cap screw is secured on the second end of the longitudinal member to secure the second end of the longitudinal member in the second housing while allowing relative motion between the second end of the longitudinal member and the second housing. In some embodiments, the cap screw comprises a threaded portion configured to engage the housing and a yoke that is rotatably coupled with the threaded portion and configured to engage the longitudinal member.

In another aspect, an apparatus for retaining vertebrae of a spinal column in a desired spatial relationship is disclosed. The apparatus comprises a first fastener having a threaded shank for engaging a vertebral portion and a first housing having a first passage and a second passage having a longitudinal axis extending transverse to the first passage. The first fastener extends through an opening in the housing into the second passage. The apparatus also comprises a second fastener having a threaded shank for engaging a vertebral portion and a second housing having a first passage and a second passage having a longitudinal axis extending transverse to the first passage. The second fastener extends through an opening in the housing into the second passage. The apparatus further comprises a longitudinal member having a first end and a second end and a member axis extending therebetween. The longitudinal member comprises an array that comprises a plurality of elongated load-bearing elements. The array may be configured to be relatively inflexible along the member axis but to be relatively flexible in a direction transverse to the member axis. The array extends at least partially between the first end and the second end of the longitudinal member. The longitudinal member is configured to extend between the first passage of the first housing and the first passage of the second housing. The apparatus also comprises a first clamping device configured to be coupled with the first housing and to secure the first end of the longitudinal member to the first housing, and a second clamping device configured to be coupled with the second housing and to secure the second end of the longitudinal member to the second housing while allowing the array of elongated elements to provide a range of relative movement of the vertebrae.

An embodiment of a longitudinal member is disclosed. The longitudinal member has a first end and a second end and a member axis extending therebetween. The longitudinal member comprises an array that comprises a plurality of elongated load-bearing elements. The array may be configured to be relatively inflexible along the member axis but to be relatively flexible in a direction transverse to the member axis. The array extends at least partially between the first end and the second end of the longitudinal member. In some embodiments, the array comprises a linear array or a cylindrical array. The elongated load bearing elements may include sheets, plates, rods, or a combination thereof.

An embodiment of a dynamic stabilization device for preserving a range of motion between adjacent vertebrae is provided. The dynamic stabilization device comprises a longitudinal member having a first end and a second end and a longitudinal axis extending therebetween. The dynamic stabilization device further comprises an array that comprises a plurality of elongated load-bearing elements. The array is relatively inflexible along the longitudinal axis and relatively flexible in a direction transverse to the longitudinal axis. The array extends at least partially between the first end and the second end of the stabilization device, wherein in use the longitudinal member allows a range of relative movement of the vertebrae. An embodiment of an apparatus for retaining vertebrae of a spinal column in a desired spatial relationship is disclosed. The apparatus comprises a first fastener for engaging a first vertebra, a second fastener for engaging a second vertebra, and an embodiment of the dynamic stabilization device, wherein in use the dynamic stabilization device is coupled to and extends between the first fastener and the second fastener.

In another form, an apparatus for retaining vertebrae of a spinal column in a desired spatial relationship is disclosed. The apparatus comprises a first fastener for engaging a portion of a vertebra and a second fastener for engaging a portion of a vertebra. The apparatus also comprises a longitudinal member having a first end and a second end and a member axis extending therebetween. The longitudinal member comprises an array that comprises a plurality of elongated load-bearing elements. The array may be configured to be relatively inflexible along the member axis but to be relatively flexible in a direction transverse to the member axis. The array extends at least partially between the first end and the second end of the longitudinal member. The longitudinal member may be configured to extend between the first fastener and the second fastener when engaged in the vertebrae and to allow a range of relative movement of the vertebrae.

An embodiment of an apparatus for stabilizing vertebrae while permitting a range of motion therebetween may include first and second fasteners for engaging adjacent vertebrae and a motion preserving device that may be coupled to the first and second fasteners. The motion preserving device may include a longitudinal member that includes an array of load-bearing elements. The longitudinal member may be configured to permit the load-bearing elements to move relative to each other and/or relative to other portions of the member. In some embodiments, the longitudinal member is relatively inflexible along a longitudinal axis and relatively flexible in a direction transverse to the longitudinal axis.

In other embodiments, the longitudinal member comprises an array of elongated elements. The elements may comprise different materials, including, for example, titanium, titanium alloys, or other biocompatible materials. In some embodiments, the longitudinal member comprises a low friction material that is used to promote sliding between the elements (and/or between other portions of the longitudinal member) and to reduce wear and to substantially prevent generation of loose debris due to the relative motion within the member. A suitable low-friction material includes ultra high molecular weight polyethylene (UHMWPE). In some embodiments, the longitudinal member includes layers that alternate in composition, for example, in one embodiment the layers alternate between titanium and UHMWPE.

In some embodiments, one or both ends of the longitudinal member may be secured to the housings such that the layers may slide relative to each other and relative to the housings. In other embodiments, one end of the longitudinal member may be clamped to the housing such that motion of the layers relative to each other and relative to the housing is minimized. In such embodiments, the layers at one end of the longitudinal member may be mechanically coupled together to prevent their relative motion, for example, by the use of rivets, welds, or adhesives.

The spinal stabilization apparatus may comprise retention members that limit the longitudinal motion of an end of the longitudinal member while allowing the elements to slide relative to each other and relative to at least one of the retention members. In some embodiments, the retention members may comprise a set of notches on the longitudinal member that are mated to a set of notches on the housing or on the cap screw. The set of notches may be disposed on one or more layers of the longitudinal member.

By coupling the multi-layered longitudinal member to the vertebrae as described, the longitudinal member acts as a spring that resists extension and flexion of the vertebrae to which the stabilization device is coupled, thereby imparting stability and natural stiffness to a diseased or damaged portion of the spine. The characteristics of the spring such as its spring rate and stiffness may be chosen by appropriately selecting the number, the length and thickness, and the material properties of the layers. The spring rate may be linear or nonlinear. In some embodiments, the spring acts as a leaf spring. In some embodiments, the longitudinal member acts as a spring in multiple dimensions, for example, in two or more directions substantially transverse to a longitudinal axis of the member. In certain embodiments, the longitudinal member is relatively inflexible along the longitudinal axis and/or is relatively flexible in directions transverse to the longitudinal axis.

BRIEF DESCRIPTION OF THE DRAWINGS

Further objects, features and advantages of the disclosure will become apparent from the following detailed description taken in conjunction with the accompanying figures showing certain illustrative embodiments of the disclosure, in which:

FIG. 2 is a perspective view of one embodiment of an expandable conduit in a reduced profile configuration;

FIG. 3 is a perspective view of the expandable conduit of FIG. 2 in a first enlarged configuration;

FIG. 4 is a perspective view of the expandable conduit of FIG. 2 in a second enlarged configuration;

FIG. 7 is a perspective view of another embodiment of an expandable conduit in an enlarged configuration;

FIG. 8 is an enlarged sectional view of the expandable conduit of FIG. 7 taken along lines 8-8 of FIG. 7;

FIG. 9 is a sectional view of the expandable conduit of FIG. 7 taken along lines 9-9 of FIG. 7;

FIG. 10 is a perspective view of another embodiment of an expandable conduit in an enlarged configuration;

FIG. 11 is an enlarged sectional view of the expandable conduit of FIG. 10 taken along lines 11-11 of FIG. 10;

FIG. 12 is a sectional view of the expandable conduit of FIG. 10 taken along lines 12-12 of FIG. 10;

FIG. 13 is a view of a portion of another embodiment of the expandable conduit;

FIG. 14 is a view of a portion of another embodiment of the expandable conduit;

FIG. 20 is an exploded perspective view of one embodiment of an endoscope mount platform;

FIG. 22 is a side view of the endoscope mount platform of FIG. 20 illustrated with one embodiment of an indexing arm and one embodiment of an endoscope;

FIG. 23 is a perspective view of one embodiment of an indexing collar of the endoscope mount platform FIG. 20;

FIG. 26 is a perspective view of one embodiment of a fastener;

FIG. 27 is an exploded perspective view of the fastener of FIG. 26;

FIG. 27(a) is an enlarged side view of one embodiment of a biasing member illustrated in FIG. 27 taken from the perspective of the arrow 27a;

FIG. 28 is a perspective view of one embodiment of a surgical instrument;

FIG. 29 is an enlarged sectional view of the fastener of FIGS. 26-27 coupled with the surgical instrument of FIG. 28, illustrating one embodiment of a stage of one embodiment of a method for treating the spine of a patient;

FIG. 30 is side view of one embodiment of another surgical instrument;

FIG. 31 is a partial sectional view of one embodiment of a stage of one embodiment of a method for treating the spine of a patient;

FIG. 32 is a side view of one embodiment of another surgical instrument;

FIG. 33 is a perspective view similar to FIG. 31 illustrating the apparatuses of FIGS. 26 and 32, in one embodiment of a stage of one embodiment of a method for treating the spine of a patient;

FIG. 34 is an enlarged sectional view of the apparatus of FIGS. 26 and 32, illustrating one embodiment of a stage of one embodiment of a method for treating the spine of a patient;

FIG. 36 is an enlarged view in partial section illustrating one embodiment of a stage of one embodiment of a method for treating the spine of a patient;

FIG. 37 is a partial view illustrating one embodiment of a stage of one embodiment of a method for treating the spine of a patient;

FIG. 46B is a perspective view of another embodiment of a dynamic stabilization apparatus;

FIG. 46C is a side plan view of the dynamic stabilization apparatus of FIG. 46B;

FIG. 46D is a top plan view of the dynamic stabilization apparatus of FIG. 46B;

FIG. 46E is a side cross-section view of the dynamic stabilization apparatus taken along section plane 46E-46E of FIG. 46D;

FIG. 46F is an exploded perspective view illustrating one embodiment of a longitudinal member;

FIG. 46G is a perspective view of the longitudinal member of FIG. 46F, with an optional sheath removed for clarity of illustration;

FIG. 46H is a perspective view of another embodiment of a longitudinal member;

FIG. 46I is a perspective view of another embodiment of a longitudinal member;

FIG. 46J is a perspective view of another embodiment of a longitudinal member;

Figure 1:
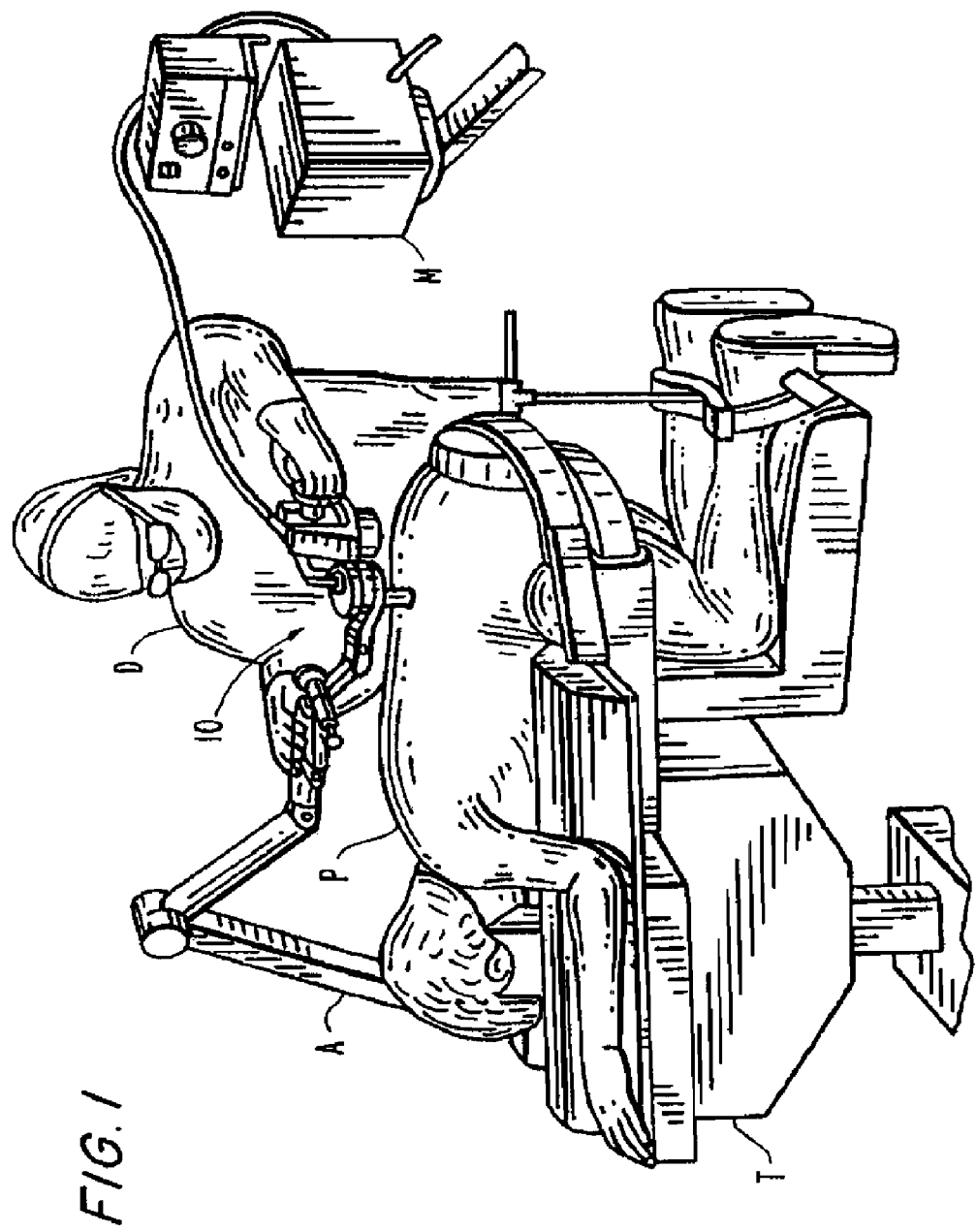
FIG. 1 is a perspective view of one embodiment of a surgical system and one embodiment of a method for treating the spine of a patient.
Figure 6:
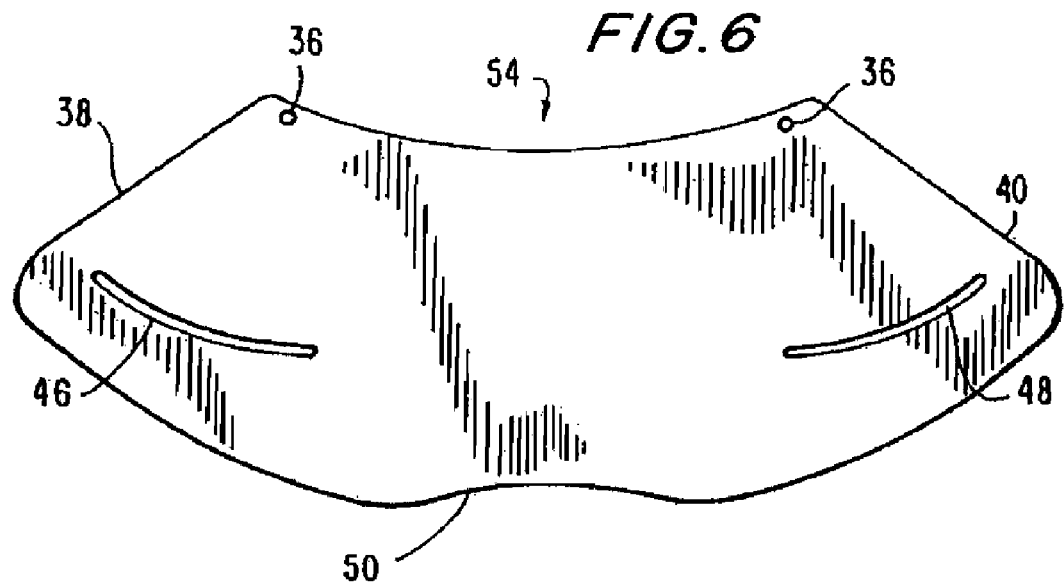
FIG. 6 is a view of another embodiment of a skirt portion of an expandable conduit.

Throughout the figures, the same reference numerals and characters, unless otherwise stated, are used to denote like features, elements, components or portions of the illustrated embodiments. Moreover, while the subject matter of the disclosure will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF PREFERRED EMBODIMENTS

As should be understood in view of the following detailed description, this application is directed to apparatuses and methods for treating the spine of a patient through an access device, also referred to herein as an expandable conduit. More particularly, the systems described below provide access to surgical locations at or near the spine and provide a variety of tools and implants or implantable devices useful in performing treatment of the spine. For example, systems and methods are described herein that may be used to provide motion preserving stabilization of the spine, such as dynamic stabilization. Access devices and systems described herein enable these systems and methods to be practiced minimally invasively. Also, the systems described herein enable a surgeon to perform a wide variety of methods as described herein.

I. Systems for Performing Procedures at a Surgical Location

Various embodiments of apparatuses and procedures described herein will be discussed in terms minimally invasive procedures and apparatuses, e.g., of endoscopic apparatuses and procedures. Many aspects of the present disclosure may also find use in conventional, open, and mini-open procedures. In the drawings and description which follows, the term "proximal," as is traditional, refers to the end portion of the apparatus which is closest to the operator, while the term "distal" will refer to the end portion which is farthest from the operator.

FIG. 1 shows one embodiment of a surgical system 10 that can be used to perform a variety of methods or procedures. In at least a portion of the procedure, as discussed more fully below, the patient P can be placed in the prone position on operating table T, taking care that the abdomen is not compressed and physiological lordosis is preserved, as is known in the art. The physician D is able to access the surgical site and perform the surgical procedure with the components of the system 10, which will be described in greater detail herein. The system 10 may be supported, in part, by a mechanical support arm A, such as the type generally disclosed in U.S. Pat. No. 4,863,133, which is hereby incorporated by reference herein in its entirety. One mechanical arm of this type is manufactured by Leonard Medical, Inc., 1464 Holcomb Road, Huntington Valley, Pa., 19006.

Visualization of the surgical site may be achieved in any suitable manner, e.g., by use of a viewing element, such as an endoscope, a camera, loupes, a microscope, direct visualization, or any other suitable viewing element, or a combination of the foregoing. In one embodiment, the viewing element provides a video signal representing images, such as images of the surgical site, to a monitor M. The viewing element may be an endoscope and camera which captures images to be displayed on the monitor M whereby the physician D is able to view the surgical site as the procedure is being performed. The endoscope and camera will be described in greater detail herein.

The systems and procedures will be described herein in connection with minimally invasive postero-lateral spinal surgery. One such method is a two level postero-lateral fixation of the spine involving the L4, L5, and S1 vertebrae. (In the drawings, the vertebrae will generally be denoted by reference letter V.) The usefulness of the apparatuses and procedures is neither restricted to the postero-lateral approach nor to the L4, L5, and S1 vertebrae, but it may be used in other anatomical approaches and other vertebra(e) within the cervical, thoracic, and lumbar regions of the spine. The procedures may be directed toward surgery involving one or more vertebral levels. It is also useful for anterior and lateral procedures. Moreover, it is believed that many embodiments may be also particularly useful where any body structures must be accessed beneath the skin and muscle tissue of the patient, and where it desirable to provide sufficient space and visibility in order to manipulate surgical instruments and treat the underlying body structures. For example, certain features or instrumentation described herein are particularly useful for a minimally invasive procedures, e.g., arthroscopic procedures. As discussed more fully below, one embodiment of an apparatus described herein provides an expandable conduit that has an expandable distal portion. The expandable distal portion prevents or substantially prevents the expandable conduit or instruments extended therethrough to the surgical site from being dislodging or popping out of the operative site.

The system 10 includes an expandable conduit or access device that provides a internal passage for surgical instruments to be inserted through the skin and muscle tissue of the patient P to the surgical site. The expandable conduit has a wall portion defining reduced profile configuration for initial percutaneous insertion into the patient. This wall portion may have any suitable arrangement. In one embodiment, discussed in more detail below, the wall portion has a generally tubular configuration that may be passed over a dilator that has been inserted into the patient to atraumatically enlarge an opening sufficiently large to receive the expandable conduit therein.

The wall portion of the expandable conduit is subsequently expanded to an enlarged configuration, by moving against the surrounding muscle tissue to at least partially define an enlarged surgical space in which the surgical procedures will be performed. In a sense, it acts as its own dilator. The expandable conduit may also be thought of as a retractor, and may be referred to herein as such. The distal portion can be expanded to a greater extent than the proximal portion, because the surgical procedures are to be performed at the surgical site which is adjacent the distal portion when the expandable conduit is inserted into the patient.

While in the reduced profile configuration, the expandable conduit defines a first unexpanded configuration. Thereafter, the expandable conduit enlarges the surgical space defined thereby by engaging the tissue surrounding the conduit and displacing the tissue radially outwardly as the conduit expands. The expandable conduit may be sufficiently rigid to displace such tissue during the expansion thereof. The expandable conduit may be resiliently biased to expand from the reduced profile configuration to the enlarged configuration. In addition, the conduit may also be manually expanded by an expander device with or without one or more surgical instruments inserted therein, as will be described below. The surgical site is at least partially defined by the expanded conduit itself. During expansion, the conduit moves from the first overlapping configuration to a second overlapping configuration.

In addition to enlargement, the distal end portion of the expandable conduit may be configured for relative movement with respect to the proximal end portion in order to allow the physician to precisely position the distal end portion at the desired location. This relative movement also provides the advantage that the proximal portion of the expandable conduit nearest the physician D may remain substantially stable during such distal movement. In an exemplary embodiment, the distal portion is a separate component which is pivotably or movably attached relative to the proximal portion. In another embodiment, the distal portion is flexible or resilient in order to permit such relative movement.

One embodiment of an expandable conduit is illustrated in FIGS. 2-6 and designated by reference number 20. The expandable conduit 20 includes a proximal wall portion 22, which has a tubular configuration, and a distal wall portion, which is an expandable skirt portion 24. The skirt portion 24 is enlargeable from a reduced profile configuration having an initial dimension 26 and corresponding cross-sectional area (illustrated in FIG. 2), to an enlarged configuration having a dimension 28 and corresponding cross-sectional area (illustrated in FIG. 4). In one embodiment, the skirt portion 24 is attached to the proximal wall portion 22 with a rivet 30, pin, or similar connecting device to permit movement of the skirt portion 24 relative to the proximal wall portion 22.

In the illustrated embodiment, the skirt portion 24 is manufactured from a resilient material, such as stainless steel. The skirt portion 24 is manufactured so that it normally assumes an expanded configuration illustrated in FIG. 4. As illustrated in FIG. 3, the skirt portion 24 may assume an intermediate dimension 34 and corresponding cross-sectional area, which is greater than the dimension 26 of the reduced profile configuration of FIG. 2, and smaller than the dimension 28 of the enlarged configuration of FIG. 4. The skirt portion 24 may assume the intermediate configuration of FIG. 3 when deployed in the patient in response to the force of the tissue acting on the skirt portion 24. The intermediate dimension 34 will depend upon several factors, including the rigidity of the skirt portion 24, the surrounding tissue, and whether such surrounding tissue has relaxed or tightened during the course of the procedure. An outer plastic sleeve 32 (illustrated in dashed line in FIG. 2) may be provided which surrounds the expandable conduit 20 and maintains the skirt portion 24 in the reduced profile configuration. The outer sleeve 32 may have a braided polyester suture embedded within it (not shown), aligned substantially along the longitudinal axis thereof; such that when the suture is withdrawn, the outer sleeve 32 is torn, which allows the expandable conduit 20 to resiliently expand from the reduced profile configuration of FIG. 2 to the expanded configurations of FIGS. 3-4. While in the reduced profile configuration of FIG. 2, the skirt portion 24 defines a first overlapping configuration 33, as illustrated by the dashed line. As the skirt portion 24 resiliently expands, the skirt portion 24 assumes the expanded configuration, as illustrated in FIGS. 3-4.

The skirt portion 24 is sufficiently rigid that it is capable of displacing the tissue surrounding the skirt portion 24 as it expands. Depending upon the resistance exerted by surrounding tissue, the skirt portion is sufficiently rigid to provide some resistance against the tissue to remain in the configurations of FIGS. 3-4. Moreover, the expanded configuration of the skirt portion 24 is at least partially supported by the body tissue of the patient. The rigidity of the skirt portion 24 and the greater expansion at the distal portion creates a stable configuration that is at least temporarily stationary in the patient, which frees the physician from the need to actively support the conduit 20 until an endoscope mount platform 300 and a support arm 400 are subsequently added in one embodiment (see FIGS. 21-22).

Figure 5:
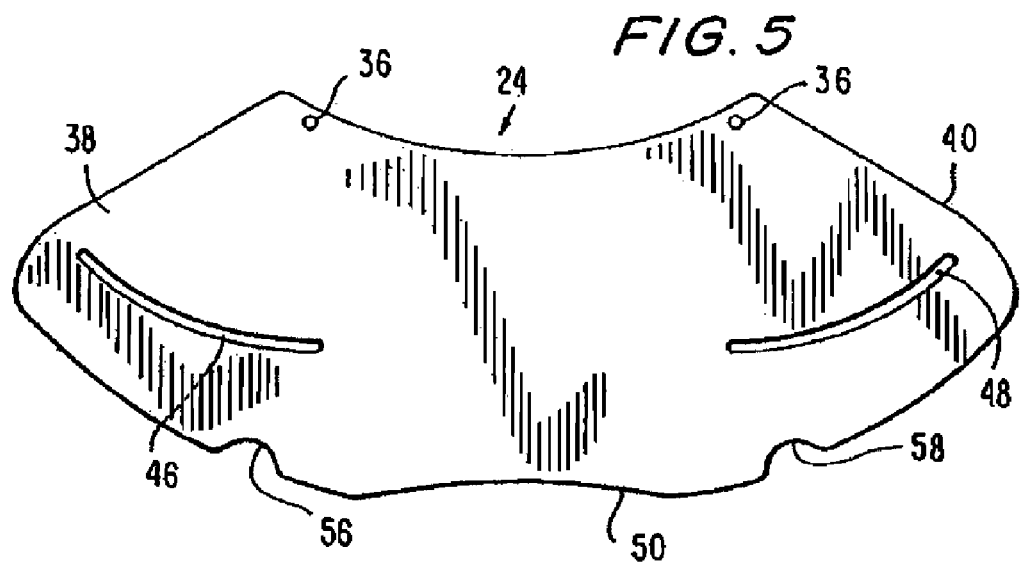
FIG. 5 is a view of one embodiment of a skirt portion of an expandable conduit.

The skirt portion 24 of the expandable conduit 20 is illustrated in an initial flattened configuration in FIG. 5. The skirt portion 24 may be manufactured from a sheet of stainless steel having a thickness of about 0.007 inches. In various embodiments, the dimension 28 of the skirt portion 24 is about equal to or greater than 50 mm, is about equal to or greater than 60 mm, is about equal to or greater than 70 mm, is about equal to or greater than 80 mm, or is any other suitable size, when the skirt portion 24 is in the enlarged configuration. In one embodiment, the dimension 28 is about 63 mm, when the skirt portion 24 is in the enlarged configuration. As discussed above, the unrestricted shape of the skirt portion 24 preferably is a circular or an oblong shape. The skirt portion 24 may also take on an oval shape, wherein the dimension 28 would define a longer dimension the skirt portion 24 and would be about 85 mm in one embodiment. In another embodiment, the skirt portion 24 has an oval shape and the dimension 28 defines a longer dimension of the skirt portion 24 and would be about 63 mm. An increased thickness, e.g., about 0.010 inches, may be used in connection with skirt portions having a larger diameter, such as about 65 mm. Other materials, such as nitinol or plastics having similar properties, may also be useful.

As discussed above, the skirt portion 24 is attached to the proximal wall portion 22 with a pivotable connection, such as rivet 30. A pair of rivet holes 36 is provided in the skirt portion 24 to receive the rivet 30. The skirt portion 24 also has two free ends 38 and 40 in one embodiment that are secured by a slidable connection, such as second rivet 44 (not shown in FIG. 5, illustrated in FIGS. 2-4). A pair of complementary slots 46 and 48 is defined in the skirt portion 24 adjacent the free ends 38 and 40. The rivet 44 is permitted to move freely within the slots 46 and 48. This slot and rivet configuration allows the skirt portion 24 to move between the reduced profile configuration of FIG. 2 and the enlarged or expanded configurations of FIGS. 3-4. The use of a pair of slots 46 and 48 reduces the risk of the "button-holing" of the rivet 44, e.g., a situation in which the opening of the slot becomes distorted and enlarged such that the rivet may slide out of the slot, and cause failure of the device. However, the likelihood of such occurrence is reduced in skirt portion 24 because each of the slots 46 and 48 in the double slot configuration has a relatively shorter length than a single slot configuration. Being shorter, the slots 46, 48 are less likely to be distorted to the extent that a rivet may slide out of position. In addition, the configuration of rivet 44 and slots 46 and 48 permits a smoother operation of enlarging and reducing the skirt portion 24, and allows the skirt portion 24 to expand to span as many as three vertebrae, e.g., L4, L5, and SI, to perform multi-level fixation alone or in combination with a variety of other procedures, as discussed below.

An additional feature of the skirt portion 24 is the provision of a shallow concave profile 50 defined along the distal edge of the skirt portion 24, which allows for improved placement of the skirt portion 24 with respect to the body structures and the surgical instruments defined herein. In one embodiment, a pair of small scalloped or notched portions 56 and 58 is provided, as illustrated in FIG. 5. When the skirt portion 24 is assembled, the notched portions 56 and 58 are oriented in the cephcaudal direction (indicated by an arrow 60 in FIG. 4) and permit instrumentation, such as an elongated member 650 used in a fixation procedure (described in detail below), to extend beyond the area enclosed by the skirt portion 24 without moving or raising the skirt portion 24 from its location to allow the elongated member 650 to pass under the skirt portion 24. The notched portions 56, 58 are optional, as illustrated in connection with another embodiment of an expandable conduit 54, illustrated in FIG. 6, and may be eliminated where the physician deems the notches to be unnecessary for the procedures to be performed, (e.g., where fixation does not require extended access, as discussed more fully below.)

As illustrated in FIG. 4, the skirt portion 24 may be expanded to a substantially conical configuration having a substantially circular or elliptical profile. In another embodiment, features may be provided on the skirt portion which facilitate the bending of the skirt portion at several locations to provide a pre-formed enlarged configuration. For example, another embodiment of an expandable conduit 70, illustrated in FIGS. 7-9, provides a skirt portion 74 that has four sections 76a, 76b, 76c, 76d having a reduced thickness. For a skirt portion 74 having a thickness 78 of about 0.007 inches, reduced thickness sections 76a, 76b, 76c, 76d may have a thickness 80 of about 0.002-0.004 inches (FIG. 8). The reduced thickness sections 76a, 76b, 76c, 76d may have a width 82 of about 1-5 mm. The thickness 78 of the skirt portion 74 may be reduced by milling or grinding, as is known in the art. When the skirt portion 74 is opened, it moves toward a substantially rectangular configuration, as shown in FIG. 9, subject to the resisting forces of the body tissue. In another embodiment (not shown), a skirt portion may be provided with two reduced thickness sections (rather than the four reduced thickness sections of skirt 74) which would produce a substantially "football"-shaped access area.

FIGS. 10-12 show another embodiment of an expandable conduit 80. The expandable conduit 80 has a skirt portion 84 with a plurality of perforations 86. The perforations 86 advantageously increase the flexibility at selected locations. The size and number of perforations 86 may vary depending upon the desired flexibility and durability. In another embodiment, the skirt portion 84 may be scored or otherwise provided with a groove or rib in order to facilitate the bending of the skirt portion at the desired location.

FIG. 13 illustrates another embodiment of an expandable conduit that has a skirt portion 94 having one slot 96 and an aperture 98. A rivet (not shown) is stationary with respect to the aperture 98 and slides within the slot 96. FIG. 14 illustrates another embodiment of an expandable conduit that has a skirt portion 104 that includes an aperture 108. The apertures 108 receives a rivet (not shown) that slides within elongated slot 106.

Further details of the expandable conduit are described in U.S. Pat. No. 6,187,000, and in U.S. patent application Ser. No. 09/772,605, filed Jan. 30, 2001, U.S. application Ser. No. 10/361,887 filed Feb. 10, 2003, and application Ser. No. 10/280,489 filed Oct. 25, 2002, which are incorporated by reference in their entirety herein.

In one embodiment of a procedure, an early stage involves determining a point in the skin of the patient at which to insert the expandable conduit. The access point preferably corresponds to the posterior-lateral aspects of the spine. Manual palpation and Anterior-Posterior (AP) fluoroscopy may be used to determine preferred or optimal locations for forming an incision in the skin of the patient. In one embodiment, the expandable conduit 20 preferably is placed midway (in the cephcaudal direction) between the L4 through SI vertebrae, centrally about 4-7 cm from the midline of the spine.

After the above-described location is determined, an incision is made at the location. A guide wire (not shown) is introduced under fluoroscopic guidance through the skin, fascia, and muscle to the approximate surgical site. A series of dilators is used to sequentially expand the incision to the desired width, about 23 mm in one procedure, without damaging the structure of surrounding tissue and muscles. A first dilator is placed over the guide wire, which expands the opening. The guide wire is then subsequently removed. A second dilator that is slightly larger than the first dilator is placed over the first dilator, which expands the opening further. Once the second dilator is in place, the first dilator is subsequently removed. This process of (1) introducing a next-larger-sized dilator coaxially over the previous dilator and (2) subsequently removing the previous dilator when the next-larger-sized dilator is in place continues until an opening of the desired size is created in the skin, muscle, and subcutaneous tissue. In one embodiment of the method, desired opening size is about 23 mm. (Other dimensions of the opening, e.g., about 20 mm, 27 mm, 30 mm, etc., are also useful with this apparatus in connection with spinal surgery, and still other dimensions are contemplated.)

Figure 15:
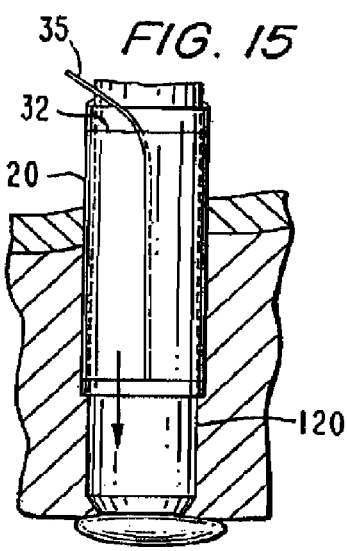
FIG. 15 is a sectional view illustrating one embodiment of a stage of one embodiment of a method for treating the spine of a patient.

FIG. 15 shows that following placement of a dilator 120, which is the largest dilator in the above-described dilation process, the expandable conduit 20 is introduced in its reduced profile configuration and positioned in a surrounding relationship over the dilator 120. The dilator 120 is subsequently removed from the patient, and the expandable conduit 20 is allowed to remain in position.

Once positioned in the patient, the expandable conduit 20 may be enlarged to provide a passage for the insertion of various surgical instruments and to provide an enlarged space for performing the procedures described herein. As described above, the expandable conduit may achieve the enlargement in several ways. In one embodiment, a distal portion of the conduit may be enlarged, and a proximal portion may maintain a constant diameter. The relative lengths of the proximal portion 22 and the skirt portion 24 may be adjusted to vary the overall expansion of the conduit 20. Alternatively, such expansion may extend along the entire length of the expandable conduit 20. In one embodiment of a procedure, the expandable conduit 20 may be expanded by removing a suture 35 and tearing the outer sleeve 32 surrounding the expandable conduit 20, and subsequently allowing the skirt portion 24 to resiliently expand towards its fully expanded configuration as (illustrated in FIG. 4) to create an enlarged surgical space from the L4 to the SI vertebrae. The resisting force exerted on the skirt portion 24 may result in the skirt portion 24 assuming the intermediate configuration illustrated in FIG. 3. Under many circumstances, the space created by the skirt portion 24 in the intermediate configuration is a sufficiently large working space to perform the procedure described herein. Once the skirt portion 24 has expanded, the rigidity and resilient characteristics of the skirt portion 24 allow the expandable conduit 20 to resist closing to the reduced profile configuration of FIG. 2 and to at least temporarily resist being expelled from the incision. These characteristics create a stable configuration for the conduit 20 to remain in position in the body, supported by the surrounding tissue. It is understood that additional support may be needed, especially if an endoscope is added.

According to one embodiment of a procedures, the expandable conduit 20 may be further enlarged at the skirt portion 24 using an expander apparatus to create a surgical access space. An expander apparatus useful for enlarging the expandable conduit has a reduced profile configuration and an enlarged configuration. The expander apparatus is inserted into the expandable conduit in the reduced profile configuration, and subsequently expanded to the enlarged configuration. The expansion of the expander apparatus also causes the expandable conduit to be expanded to the enlarged configuration. In some embodiments, the expander apparatus may increase the diameter of the expandable conduit along substantially its entire length in a conical configuration. In other embodiments, the expander apparatus expands only a distal portion of the expandable conduit, allowing a proximal portion to maintain a constant diameter.

In addition to expanding the expandable conduit, the expander apparatus may also be used to position the distal portion of the expandable conduit at the desired location for the surgical procedure. The expander engages an interior wall of the expandable conduit, and moves the conduit to the proper location. For the embodiments in which the distal portion of the expandable conduit is relatively movable with respect to the proximal portion, the expander apparatus is useful to position the distal portion without substantially disturbing the proximal portion.

Figure 17:
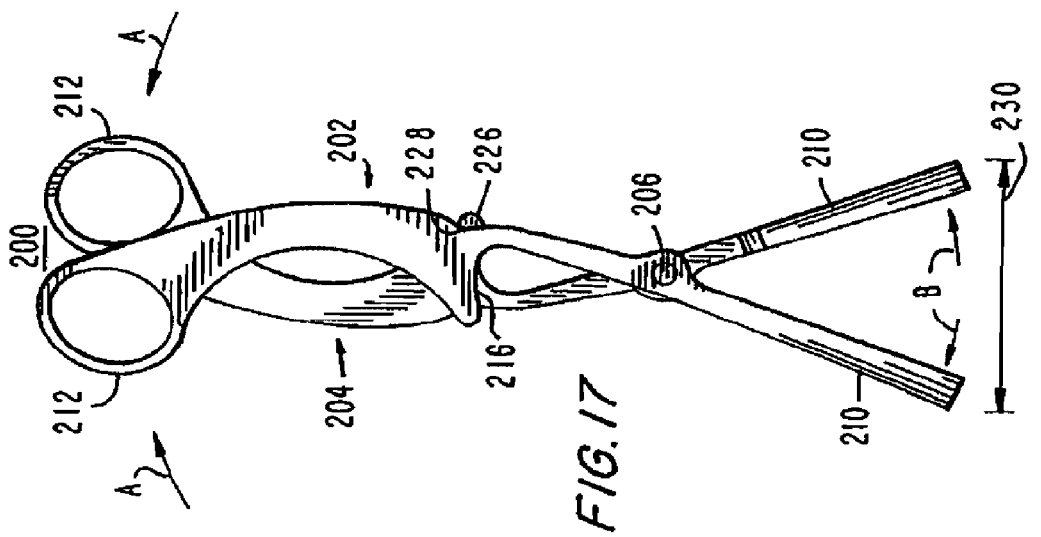
FIG. 17 is a side view of the expander apparatus of FIG. 16 in an expanded configuration.
Figure 16:
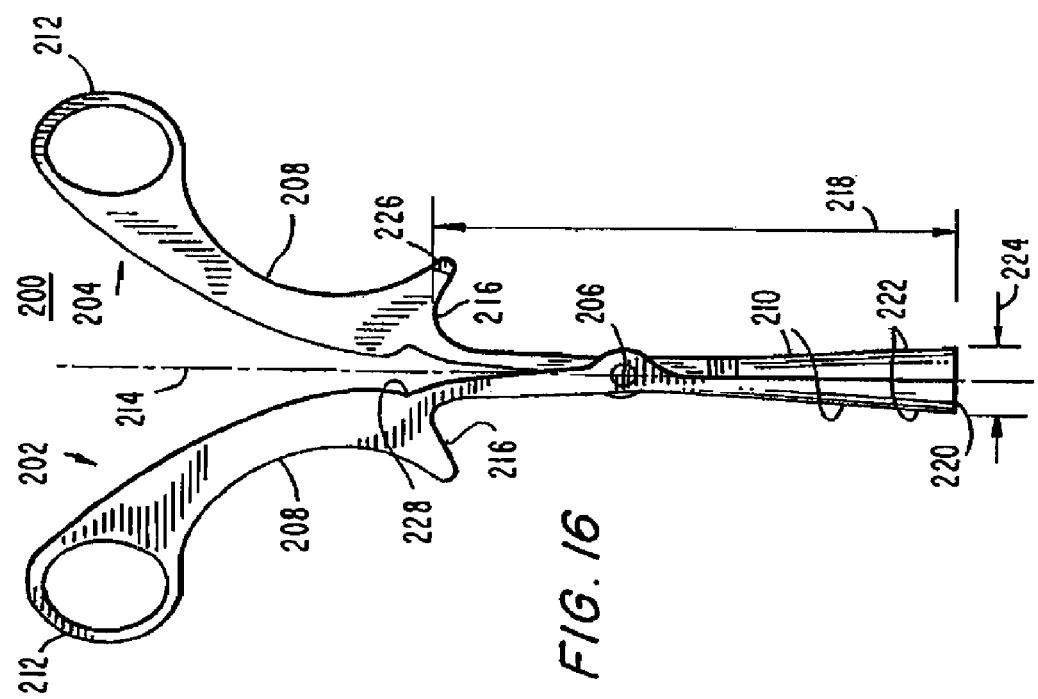
FIG. 16 is a side view of one embodiment of an expander apparatus in a reduced profile configuration.

In some procedures, an expander apparatus is used to further expand the skirt portion 24 towards the enlarged configuration (illustrated in FIG. 4). The expander apparatus is inserted into the expandable conduit, and can have two or more members which are movable to engage the interior wall of the skirt portion 24 and apply a force sufficient to further expand the skirt portion 24. FIGS. 16 and 17 show one embodiment of an expander apparatus 200 that has a first component 202 and a second component 204. A first component 202 and a second component 204 of the expander apparatus 200 are arranged in a tongs-like configuration and are pivotable about a pin 206. The first and second components 202 and 204 can be constructed of steel having a thickness of about 9.7 min. Each of the first and second components 202 and 204 has a proximal handle portion 208 and a distal expander portion 210. Each proximal handle portion 208 has a finger grip 212 that may extend transversely from an axis, e.g., a longitudinal axis 214, of the apparatus 200. The proximal handle portion 208 may further include a stop element, such as flange 216 that extends transversely from the longitudinal axis 214. The flange 216 is dimensioned to engage the proximal end 25 of the expandable conduit 20 when the apparatus 200 is inserted a predetermined depth. This arrangement provides a visual and tactile indication of the proper depth for inserting the expander apparatus 200. In one embodiment, a dimension 218 from the flange 216 to the distal tip 220 is about 106 mm. The dimension 218 is determined by the typical depth of the body structures beneath the skin surface at which the surgical procedure is being performed. The distal portions 210 are each provided with an outer surface 222 for engaging the inside wall of the skirt portion 24. The outer surface 222 is a frusto-conical surface in one embodiment. The expander apparatus 200 has an unexpanded distal width 224 at the distal tip 220 that is about 18.5 mm in one embodiment.

In use, the finger grips 212 are approximated towards one another, as indicated by an arrow A in FIG. 17, which causes the distal portions 210 to move to the enlarged configuration, as indicated by arrows B. The components 202 and 204 are also provided with a cooperating tab 226 and shoulder portion 228 which are configured for "mutual engagement when the distal portions 210 are in the expanded configuration. In the illustrated embodiment, the expander apparatus 200 has an expanded distal width 230 that extends between the distal portions 210. The expanded distal width 230 can be about 65 mm or less, about as large as 83 mm or less, or any other suitable width. The tab 226 and shoulder portion 228 together limit the expansion of the expander apparatus 200 to prevent expansion of the skirt portion 24 of the expandable conduit 20 beyond its designed dimension, and to minimize trauma to the underlying tissue. Further details of the expander apparatus are described in U.S. patent application Ser. No. 09/906,463 filed Jul. 16, 2001, which is incorporated by reference in their entirety herein.

When the expandable conduit 20 is inserted into the patient and the outer sleeve 32 is removed, the skirt portion 24 expands to a point where the outward resilient expansion of the skirt portion 24 is balanced by the force of the surrounding tissue. The surgical space defined by the conduit may be sufficient to perform any of a number of surgical procedures or combination of surgical procedures described herein. However, if it is desired to expand the expandable conduit 20 further, the expander apparatus 200 may be inserted into the expandable conduit 20 in the reduced profile configuration until the shoulder portions 216 are in approximation with the proximal end 25 of the skirt portion 24 of the expandable conduit 20, as shown in FIG. 18.

Figure 18:
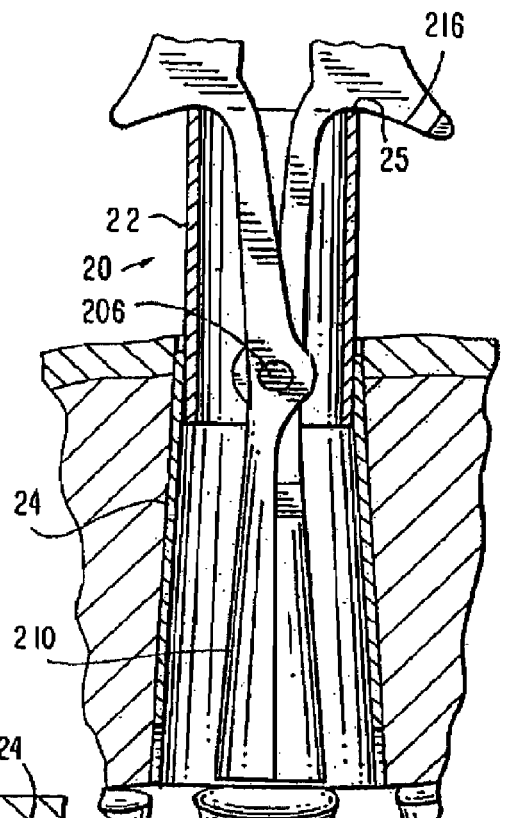
FIG. 18 is a sectional view of the expander apparatus of FIGS. 16-17 inserted into the expandable conduit of FIG. 2, which has been inserted into a patient.
Figure 19:
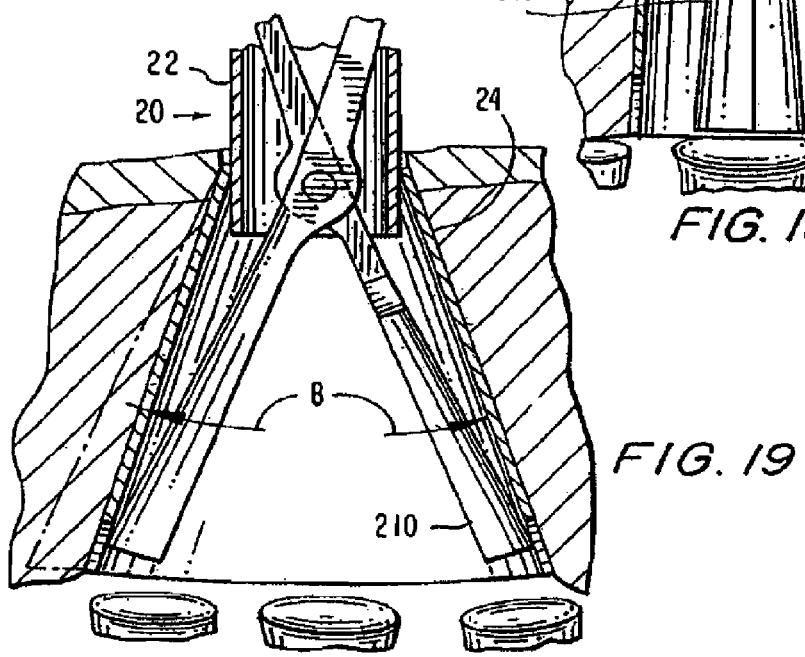
FIG. 19 is a sectional view of the expander apparatus of FIGS. 16-17 inserted into the expandable conduit of FIG. 2 and expanded to the expanded configuration to retract tissue.

FIG. 18 shows the expander apparatus 200 is inserted in the expandable conduit 20 in the reduced profiled configuration. Expansion of the expander apparatus 200 is achieved by approximating the handle portions 212 (not shown in FIG. 18), which causes the distal portions 210 of the expander apparatus 200 to move to a spaced apart configuration. As the distal portions 210 move apart and contact the inner wall of the skirt portion 24, the skirt portion 24 is expanded by allowing the rivet 44 to slide within the slots 46 and 48 of the skirt portion 24. When the distal portions 210 reach the maximum expansion of the skirt portion 24 (illustrated by a dashed line in FIG. 19), the tab 226 and shoulder portion 228 of the expander apparatus 200 come into engagement to prevent further expansion of the tong portions (as illustrated in FIG. 17). The conduit 20 may be alternatively further expanded with a balloon or similar device.

A subsequent, optional step in the procedure is to adjust the location of the distal portion of the expandable conduit 20 relative to the body structures to be operated on. For example, the expander apparatus 200 may also be used to engage the inner wall of the skirt portion 24 of the expandable conduit 20 in order to move the skirt portion 24 of the expandable conduit 20 to the desired location. For an embodiment in which the skirt portion 24 of the expandable conduit 20 is relatively movable relative to the proximal portion, e.g. by use of the rivet 30, the expander apparatus 200 is useful to position the skirt portion 24 without substantially disturbing the proximal portion 22 or the tissues closer to the skin surface of the patient. As will be described below, the ability to move the distal end portion, e.g., the skirt portion 24, without disturbing the proximal portion is especially beneficial when an additional apparatus is mounted relative to the proximal portion of the expandable conduit, as described below.

An endoscope mount platform 300 and indexing arm 400 provide securement of an endoscope 500 on the proximal end 25 of the expandable conduit 20 for remotely viewing the surgical procedure, as illustrated in FIGS. 20-23. The endoscope mount platform 300 may also provide several other functions during the surgical procedure. The endoscope mount platform 300 includes a base 302 that extends laterally from a central opening 304 in a general ring-shaped configuration. The base 302 provides an aid for the physician, who is primarily viewing the procedure by observing a monitor, when inserting surgical instruments into the central opening 304. For example, the size of the base 302 provides visual assistance (as it may be observable in the physician's peripheral vision) as well as provides tactile feedback as the instruments are lowered towards the central opening 304 and into the expandable conduit 20.

The endoscope mount platform 300 further provides a guide portion 306 that extends substantially parallel to a longitudinal axis 308 away from the central opening 304. The base 302 can be molded as one piece with the guide portion 306. The base 302 and guide portion 306 may be constructed as a suitable polymer such as polyetheretherketone (PEEK).

The guide portion 306 includes a first upright member 310 that extends upward from the base 302 and a second upright member 312 that extends upward from the base 302. The upright members 310, 312 each have a respective vertical grooves 314 and 315 that can slidably receive an endoscopic mount assembly 318.

The endoscope 500 (not shown in FIG. 20) is movably mounted to the endoscope mount platform 300 by the endoscope mount assembly 318. The endoscope mount assembly 318 includes an endoscope mount 320 and a saddle unit 322. The saddle unit 322 is slidably mounted is within the grooves 314 and 315 in the upright members 310 and 312. The endoscope mount 320 receives the endoscope 500 through a bore 326 which passes through the endoscope mount 320. Part of the endoscope 500 may extend through the expandable conduit 20 substantially parallel to longitudinal axis 308 into the patient's body 130.

The endoscope mount 320 is removably positioned in a recess 328 defined in the substantially "U"-shaped saddle unit 322, which is selectively movable in a direction parallel to the longitudinal axis 308 in order to position the endoscope 500 at the desired height within the expandable conduit 20 to provide a zoom feature to physician's view of the surgical procedure.

A screw mechanism 340 is positioned on the base 302 between the upright members 310 and 312, and is used to selectively move the saddle unit 322, and the endoscope mount 320 and the endoscope 500 which are supported by the saddle unit 322. The screw mechanism 340 comprises a thumb wheel 342 and a spindle 344. The thumb wheel 343 is rotatably mounted in a bore in the base 302. The thumb wheel 342 has an external thread 346 received in a cooperating thread in the base 302. The spindle 344 is mounted for movement substantially parallel to the central axis 308. The spindle 344 has a first end received in a rectangular opening in the saddle unit 322, which inhibits rotational movement of the spindle 344. The second end of the spindle 344 has an external thread which cooperates with an internal thread formed in a bore within the thumb wheel 342. Rotation of the thumb wheel 342 relative to the spindle 344, causes relative axial movement of the spindle unit 344 along with the saddle unit 322. Further details of the endoscope mount platform are described in U.S. patent application Ser. No. 09/491,808 filed Jan. 28, 2000, application Ser. No. 09/821,297 filed Mar. 29, 2001, and application Ser. No. 09/940,402 filed Aug. 27, 2001.

Figure 21:
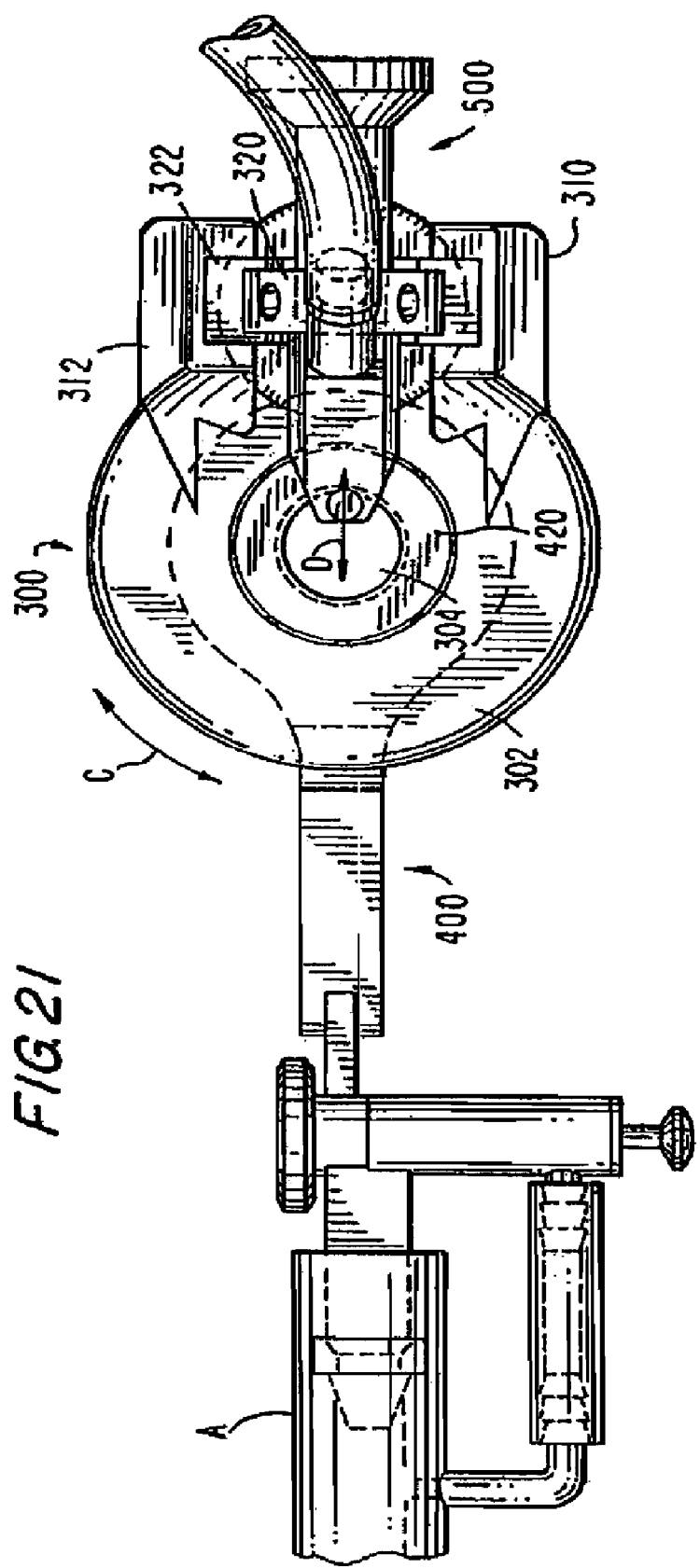
FIG. 21 is a top view of the endoscope mount platform of FIG. 20 coupled with one embodiment of an indexing arm and one embodiment of an endoscope.

FIG. 21-23 show that the endoscope mount platform 300 is mountable to the support arm 400 in one embodiment. The support arm 400, in turn, preferably is mountable to mechanical support, such as mechanical support arm A, discussed above in connection with FIG. 1. The support arm 400 rests on the proximal end 25 of the expandable conduit 20. The support arm 400 includes an indexing collar 420, which is received in the central opening 304 of the base 302 of endoscope mount platform 300. The indexing collar 420 is substantially toroidal in section and has an outer peripheral wall surface 422, an inner wall surface 424, and a wall thickness 426 that is the distance between the wall surfaces 422, 424. The indexing collar 420 further includes a flange 428, which supports the indexing collar 420 on the support arm 400.

The collars 420 advantageously make the surgical system 10 a modular in that different expandable conduits 20 may be used with a single endoscope mount platform 300. For example, expandable conduits 20 of different dimensions may be supported by providing of indexing collars 420 to accommodate each conduit size while using a single endoscope mount platform 300. The central opening 304 of the endoscope mount platform 300 has constant dimension, e.g., a diameter of about 32.6 mm. An appropriate indexing collar 420 is selected, e.g., one that is appropriately sized to support a selected expandable conduit 20. Thus the outer wall 422 and the outer diameter 430 are unchanged between different indexing collars 420, although the inner wall 424 and the inner diameter 432 vary to accommodate differently sized conduits 20.

The indexing collar 420 is mounted to the proximal portion of the expandable conduit 20 and allows angular movement of the endoscope mount platform 300 with respect thereto about the longitudinal axis 308 (as indicated by an arrow C in FIG. 21). The outer wall 422 of the index collar 420 includes a plurality of hemispherical recesses 450 that can receive one or more ball plungers 350 on the endoscope mount platform 300 (indicated in dashed line.) This arrangement permits the endoscope mount platform 300, along with the endoscope 500, to be fixed in a plurality of discrete angular positions. Further details of the support arm and indexing collar are described in U.S. Pat. No. 6,361,488, issued Mar. 26, 2002, U.S. Pat. No. 6,530,880 issued Mar. 11, 2003, and application Ser. No. 09/940,402 filed Aug. 27, 2001.

Figure 24:
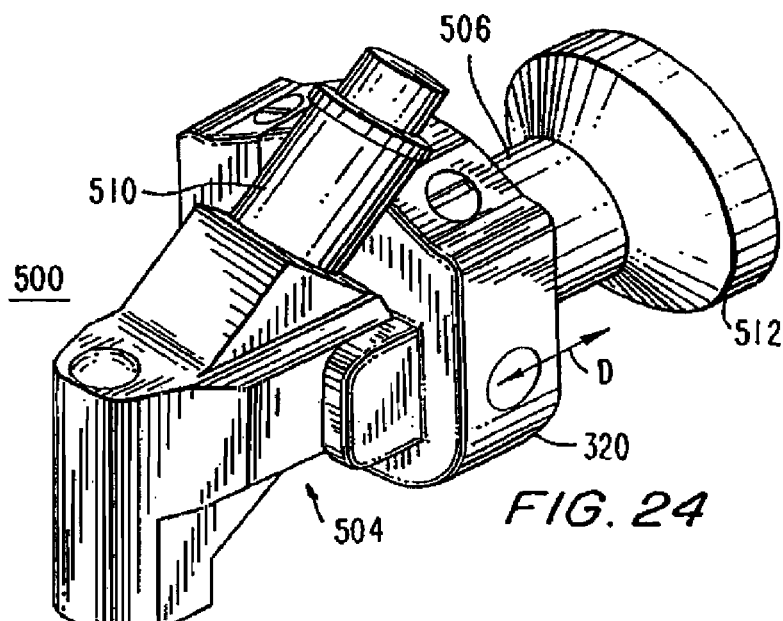
FIG. 24 is a perspective view of one embodiment of an endoscope.

FIG. 24 shows one embodiment of the endoscope 500, which has an elongated configuration that extends into the expandable conduit 20 in order to view the surgical site. In particular, the endoscope 500 has an elongated rod portion 502 and a body portion 504 which is substantially perpendicular thereto. In the illustrated embodiment, the rod portion 502 of endoscope 500 has a diameter of about 4 mm and a length of about 106 mm. Body portion 504 may define a tubular portion 506 which is configured to be slidably received in the bore 326 of endoscope mount 320 as indicated by an arrow D. The slidable mounting of the endoscope 500 on the endoscope mount platform 300 permits the endoscope 500 to adjust to configurations that incorporate different conduit diameters. Additional mobility of the endoscope 500 in viewing the surgical site may be provided by rotating the endoscope mount platform 300 about the central axis 308 (as indicated by arrow C in FIG. 21).

The rod portion 502 supports an optical portion (not shown) at a distal end 508 thereof, which may define a field of view of about 105 degrees and a direction of view 511 of about 25-30 degrees. An eyepiece 512 is positioned at an end portion of the body portion 504. A camera (not shown) preferably is attached to the endoscope 500 adjacent the eyepiece 512 with a standard coupler unit. A light post 510 supplies illumination to the surgical site at the distal end portion 508. A preferred camera for use in the system and procedures described herein is a three chip unit that provides greater resolution to the viewed image than a single chip device.

Figure 25:
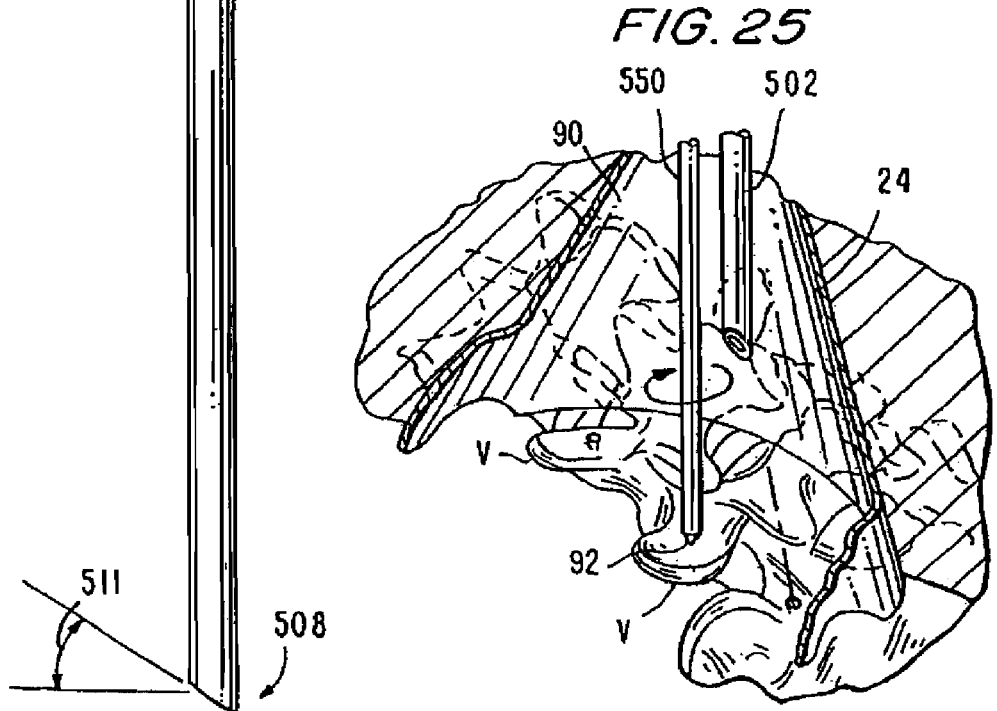
FIG. 25 is a partial sectional view of one embodiment of a stage of one embodiment of a method for treating the spine of a patient.

A subsequent stage in the procedure involves placing the support arm 400 and the endoscope mount platform 300 on the proximal portion, e.g., the proximal end 25, of the expandable conduit 20 (FIGS. 1 and 22), and mounting of the endoscope 500 on the endoscope mount platform 300. A next step is insertion of one or more surgical instruments into the expandable conduit 20 to perform the surgical procedure on the body structures at least partially within the operative space defined by the expanded portion of the expandable conduit. FIG. 25 shows that in one method, the skirt portion 24 of expandable conduit 20 at least partially defines a surgical site or operative space 90 in which the surgical procedures described herein may be performed. Depending upon the overlap of the skirt portion, the skirt portion may define a surface which is continuous about the circumference or which is discontinuous having one or more gaps where the material of the skirt portion does not overlap.

One procedure performable through the expandable conduit 20, described in greater detail below, is a two-level spinal fixation. Surgical instruments inserted into the expandable conduit may be used for debridement and decortication. In particular, the soft tissue, such as fat and muscle, covering the vertebrae may be removed in order to allow the physician to visually identify the various "landmarks," or vertebral structures, which enable the physician to locate the location for attaching a fastener, such a fastener 600, discussed below, or other procedures, as will be described herein. Allowing visual identification of the vertebral structures enables the physician to perform the procedure while viewing the surgical area through the endoscope, microscope, loupes, etc., or in a conventional, open manner.

Tissue debridement and decortication of bone are completed using one or more debrider blades, bipolar sheath, high speed burr, and additional conventional manual instruments. The debrider blades are used to excise, remove and aspirate the soft tissue. The bipolar sheath is used to achieve hemostasis through spot and bulk tissue coagulation. The debrider blades and bipolar sheath are described in greater detail in U.S. Pat. No. 6,193,715, assigned to Medical Scientific, Inc., which is incorporated by reference in its entirety herein. The high speed burr and conventional manual instruments are also used to continue to expose the structure of the vertebrae.

A subsequent stage is the attachment of fasteners to the vertebrae V. Prior to attachment of the fasteners, the location of the fastener attachment is confirmed. In the exemplary embodiment, the pedicle entry point of the L5 vertebrae is located using visual landmarks as well as lateral and A/P fluoroscopy, as is known in the art. With continued reference to FIG. 25, the entry point 92 is prepared with an awl 550. The pedicle hole 92 is completed using instruments known in the art such as a straight bone probe, a tap, and a sounder. The sounder, as is known in the art, determines whether the hole that is made is surrounded by bone on all sides, and that there has been no perforation of the pedicle wall.

After hole in the pedicle is provided at the entry point 92 (or at any point during the procedure), an optional step is to adjust the location of the distal portion of the expandable conduit 20. This may be performed by inserting the expander apparatus 200 into the expandable conduit 20, expanding the distal portions 210, and contacting the inner wall of the skirt portion 24 to move the skirt portion 24 to the desired location. This step may be performed while the endoscope 500 is positioned within the expandable conduit 20, and without substantially disturbing the location of the proximal portion of the expandable conduit 20 to which the endoscope mount platform 300 may be attached.

FIGS. 26-27 illustrate a fastener 600 that is particularly applicable in a procedures involving fixation. The fastener 600 is described in greater detail in U.S. patent application Ser. No. 10/075,668, filed Feb. 13, 2002 and application Ser. No. 10/087,489, filed Mar. 1, 2002, which are incorporated by reference in their entirety herein. Fastener 600 includes a screw portion 602, a housing 604, a spacer member 606, a biasing member 608, and a clamping member, such as a cap screw 610. The screw portion 602 has a distal threaded portion 612 and a proximal, substantially spherical joint portion 614. The threaded portion 612 is inserted into the hole 92 in the vertebrae, as will be described below. The substantially spherical joint portion 614 is received in a substantially annular, part spherical recess 616 in the housing 604 in a ball and socket joint relationship (see also FIG. 29).

As illustrated in FIG. 27, the fastener 600 is assembled by inserting the screw portion 602 into a bore in a passage 618 in the housing 604, until the joint portion 614 engages the annular recess 616. The screw portion 602 is retained in the housing 604 by the spacer member 606 and biasing member 608. The biasing member 608 provides a biasing force to drive the spacer member 606 in frictional engagement with the joint portion 614 of the screw member 602 and the annular recess 616 of the housing 604. The biasing provided by the biasing member 602 frictionally maintains the relative positions of the housing 604 with respect to the screw portion 602. The biasing member 608 is selected such that biasing force prevents unrestricted movement of the housing 604 relative to the screw portion 602. However, the biasing force is insufficient to resist the application of force by a physician to move the housing 604 relative to the screw portion 602. In other words, this biasing force is strong enough maintain the housing 604 stationary relative to the screw portion 602, but this force may be overcome by the physician to reorient the housing 604 with respect to the screw member 602, as will be described below.

In the illustrated embodiment, the biasing member 608 is a resilient ring having a gap 620, which permits the biasing member 608 to radially contract and expand. FIG. 27(a) illustrates that the biasing member 608 may have an arched shape, when viewed end-on. The arched shape of the spring member 608 provides the biasing force, as will be described below. The spacer member 606 and the biasing member 608 are inserted into the housing 604 by radially compressing the biasing member into an annular groove 622 in the spacer member 606. The spacer member 606 and the biasing member 608 are slid into the passage 618 until the distal surface of the spacer member 606 engages the joint portion 614 of the screw portion 602, and the biasing member 608 expands radially into the annular groove 622 in the housing 604. The annular groove 622 in the housing 604 has a dimension 623 which is smaller than the uncompressed height of the arched shape of the biasing member 608. When the biasing member 608 is inserted in the annular groove 620, the biasing member 608 is flattened against its normal bias, thereby exerting the biasing force to the spacer member 606. It is understood that similar biasing members, such as coiled springs, belleville washers, or the like may be used to supply the biasing force described herein.

The spacer member 606 is provided with a longitudinal bore 626, which provides access to a hexagonal recess 628 in the proximal end of the joint portion 614 of the screw member 602. The proximal portion of the housing 604 includes a pair of upright members 630 and 631 that are separated by substantially "U"-shaped grooves 632. A recess for receiving elongated member 650 is defined by the pair of grooves 632 between upright member 630 and 631. Elongated member 650 to be placed distally into the housing 604 in an orientation substantially transverse to the longitudinal axis of the housing 604, as will be described below. The inner walls of the upright members 630 and 631 are provided with threads 634 for attachment of the cap screw 610 by threads 613 therein.

The fastener 600 is inserted into the expandable conduit 20 and guided to the prepared hole 92 in the vertebrae as a further stage of the procedure. The fastener 600 must be simultaneously supported and rotated in order to be secured in hole 92. In the illustrated embodiment the fastener 600 is supported and attached to the bone by an endoscopic screwdriver apparatus 660, illustrated in FIGS. 28-29. The screwdriver 660 includes a proximal handle portion 662 (illustrated in dashed line), an elongated body portion 664, and a distal tool portion 666.

The distal tool portion 666, as illustrated in greater detail in FIG. 29 includes a substantially hexagonal outer periphery which is received in the substantially hexagonal recess 628 in the joint portion 614 of the screw member 602. A spring member at the distal tool portion 666 releasably engages the hexagonal recess 628 of the screw member 602 to support the fastener 600 during insertion and tightening. In the illustrated embodiment, a spring member 672 is configured to engage the side wall of the recess 628. More particularly, a channel/groove is provided in the tip portion 666 for receiving the spring member 672. The channel/groove includes a medial longitudinal notch portion 676, a proximal, angled channel portion 678, and a distal substantially transverse channel portion 680. The spring member 672 is preferably manufactured from stainless steel and has a medial portion 682 that is partially received in the longitudinal notch portion 676, an angled proximal portion 684 which is fixedly received in the angled channel portion 678, and a transverse distal portion 686 which is slidably received in the transverse channel 680. The medial portion 682 of the spring member 672 is partially exposed from the distal tip portion 666 and normally biased in a transverse outward direction with respect to the longitudinal axis (indicated by arrow E), in order to supply bearing force against the wall of the recess 628. Alternatively the distal tip portion of the screw driver may be magnetized in order to hold the screw portion 602. Similarly, the distal tip portion may include a ball bearing or similar member which is normally biased in a radially outward direction to engage the interior wall of the recess 628 to secure the fastener 600 to the screwdriver distal tip 666.

The insertion of the fastener 600 into the prepared hole 92 may be achieved by insertion of screwdriver 660 into conduit 20 (indicated by arrow G). This procedure may be visualized by the use of the endoscope 500 in conjunction with fluoroscopy. The screw portion 602 is threaded into the prepared hole 92 by the endoscopic screwdriver 660 (indicated by arrow H). The endoscopic screwdriver 660 is subsequently separated from the fastener 600, by applying a force in the proximal direction, and thereby releasing the distal tip portion 666 from the hexagonal recess 628 (e.g., causing the transverse distal portion 686 of the spring member 672 to slide within the transverse recess 680 against the bias, indicated by arrow F), and removing the screwdriver 660 from the expandable conduit 20. An alternative method may use a guidewire, which is fixed in the hole 92, and a cannulated screw which has an internal lumen (as is known in the art) and is guided over the guidewire into the hole 92. The screwdriver would be cannulated as well to fit over the guidewire.

For a two-level fixation, it may be necessary to prepare several holes and attach several fasteners 600. The expandable conduit 20 can be sized in order to provide simultaneous access to all vertebrae in which the surgical procedure is being performed. In some cases, however, additional enlargement or repositioning of the distal portion of the expandable conduit may be required in order to have sufficient access to the outer vertebrae, e.g., the L4 and S1 vertebrae. In the illustrated embodiment, the expander apparatus 200 may be repeatedly inserted into the expandable conduit 20 and expanded in order to further open or position the skirt portion 24. In one procedure, additional fasteners are inserted in the L4 and S1 vertebrae in a similar fashion as the fastener 600 inserted in to the L5 vertebra as described above. (When discussed individually or collectively, a fastener and/or its individual components will be referred to by the reference number, e.g., fastener 600, housing 604, and all fasteners 600. However, when several fasteners and/or their components are discussed in relation to one another, an alphabetic subscript will be used, e.g., fastener 600a is moved towards fastener 600b.)

In a further stage of the procedure, the housing portions 604 of the fasteners 600 are substantially aligned such that their upright portions 630 and 631 face upward, and the notches 632 are substantially aligned to receive the elongated member 650 therein. The frictional mounting of the housing 604 to the screw member 602, described above, allows the housing 604 to be temporarily positioned until a subsequent tightening step, described below. Positioning of the housing portions 604 may be performed by the use of an elongated surgical instrument capable of contacting and moving the housing portion to the desired orientation. One such instrument for positioning the housings 604 is a grasper apparatus 700, illustrated in FIG. 30. The grasper apparatus 700 includes a proximal handle portion 702, an elongated body portion 704, and distal nose portion 706. The distal nose portion 706 includes a pair of grasping jaws 708a and 708b, which are pivotable about pin 710 by actuation of the proximal handle portion 702. The grasping jaws 708a and 708b are illustrated in the closed position in FIG. 30. As is known in the art, pivoting the movable handle 714 towards stationary handle 714 causes longitudinal movement of actuator 716, which in turn pivots the jaw 708b towards an open position (illustrated in dashed line). The biasing members 718 and 720 are provided to return the handles 712 and 714 to the open position and bias the jaws 708a and 708b to the closed position.

A subsequent stage in the process is the insertion of the elongated member 650 into the expandable conduit. The elongated member 650 is manufactured from a biocompatible material and must be sufficiently strong to maintain the positioning of the vertebrae, or other body structures. In the exemplary embodiment, the elongated members 650 are manufactured from Titanium 6/4 or titanium alloy. Alternatively, the elongated member 650 may be manufactured from stainless steel or other suitable material. The radii and length of the elongated members 650 are selected by the physician to provide the best fit for the positioning of the screw heads. Such selection may be performed by placing the elongated member 650 on the skin of the patient overlying the location of the fasteners and viewed fluoroscopically. For example, a 70 mm preformed rod having a 3.5" bend radius may be selected for the spinal fixation.

The elongated member 650 is subsequently fixed to each of the fasteners 600, and more particularly, to the housings 604 of each fastener 600. The grasper apparatus 700, described above, is also particularly useful for inserting the elongated member 650 into the expandable conduit 20 and positioning it with respect to each housing 604. As illustrated in FIG. 30, the jaws 708a and 708b of the grasper apparatus 700 each has a curved contact portion 722a and 722b for contacting and holding the outer surface of the elongated member 650.

As illustrated in FIG. 31, the grasper apparatus 700 may be used to insert the elongated member 650 into the operative space 90 defined at least partially by the skirt portion 24 of the expandable conduit 20. The cut-out portions 56 and 58 provided in the skirt portion 24 assist in the process of installing the elongated member 650 with respect to the housings 604. The cut-out portions 56 and 58 allow an end portion 652 of the elongated member 650 to extend beyond the operative space without raising or repositioning the skirt portion 24. The elongated member 650 is positioned within the recesses in each housing 604 defined by grooves 632 disposed between upright members 630 and 631. The elongated member 650 is positioned in an orientation substantially transverse to the longitudinal axis of each housing 604.

Further positioning of the elongated member 650 may be performed by guide apparatus 800, illustrated in FIG. 32. Guide apparatus 800 is useful in cooperation with an endoscopic screwdriver, such as endoscopic screwdriver 660 (illustrated in FIG. 28), in order to position the elongated member 650, and to introduce and tighten the cap screw 610, described above and illustrated in FIG. 27. Tightening of the cap screw 610 with respect to the housing 604 fixes the orientation of the housing 604 with respect to the screw portion 602 and fixes the position of the elongated member 650 with respect to the housing 604.

In the illustrated embodiment, the guide apparatus 800 has a proximal handle portion 802, an elongated body portion 804, and a distal tool portion 806. The elongated body portion 804 defines a central bore 808 (illustrated in dashed line) along its longitudinal axis 810. The central bore 808 is sized and configured to receive the endoscopic screwdriver 660 and cap screw 610 therethrough. In the exemplary embodiment, the diameter of the central bore 808 of the elongated body portion 804 is about 0.384-0.388 inches in diameter, and the external diameter of the endoscopic screwdriver 660 (FIG. 28) is about 0.25 inches. The proximal handle portion 802 extends transverse to the longitudinal axis 810, which allows the physician to adjust the guide apparatus 800 without interfering with the operation of the screwdriver 660.

The distal portion 806 of the apparatus includes several semicircular cut out portions 814 which assist in positioning the elongated member 650. As illustrated in FIG. 33, the cut out portions 814 are sized and configured to engage the surface of elongated member 650 and move the elongated member 650 from an initial location (illustrated in dashed line) to a desired location.

As illustrated in FIG. 34, the guide apparatus 800 is used in cooperation with the endoscopic screwdriver 660 to attach the cap screw 610. The distal end of the body portion 804 includes a pair of elongated openings 816, which permit the physician to endoscopically view the cap screw 610 retained at the distal tip 666 of the endoscopic screw driver 660.

The guide apparatus 800 and the endoscopic screwdriver 660 may cooperate as follows. The guide apparatus 800 is configured to be positioned in a surrounding configuration with the screwdriver 600. In the illustrated embodiment, the body portion 804 is configured for coaxial placement about the screwdriver 660 in order to distribute the contact force of the guide apparatus 800 on the elongated member 650. The distal portion 806 of the guide apparatus 800 may bear down on the elongated member 650 to seat the elongated member 650 in the notches 632 in the housing 604. The "distributed" force of the guide apparatus 800 may contact the elongated member 650 on at least one or more locations. In addition, the diameter of central bore 808 is selected to be marginally larger than the exterior diameter of cap screw 610, such that the cap screw 610 may freely slide down the central bore 808, while maintaining the orientation shown in FIG. 34. This configuration allows the physician to have effective control of the placement of the cap screw 610 into the housing 604. The cap screw 610 is releasably attached to the endoscopic screwdriver 660 by means of spring member 672 engaged to the interior wall of hexagonal recess 611 as it is inserted within the bore 808 of the body portion 804 of guide apparatus 800. The cap screw 610 is attached to the housing 604 by engaging the threads 615 of the cap screw 610 with the threads 634 of the housing.

Figure 35:
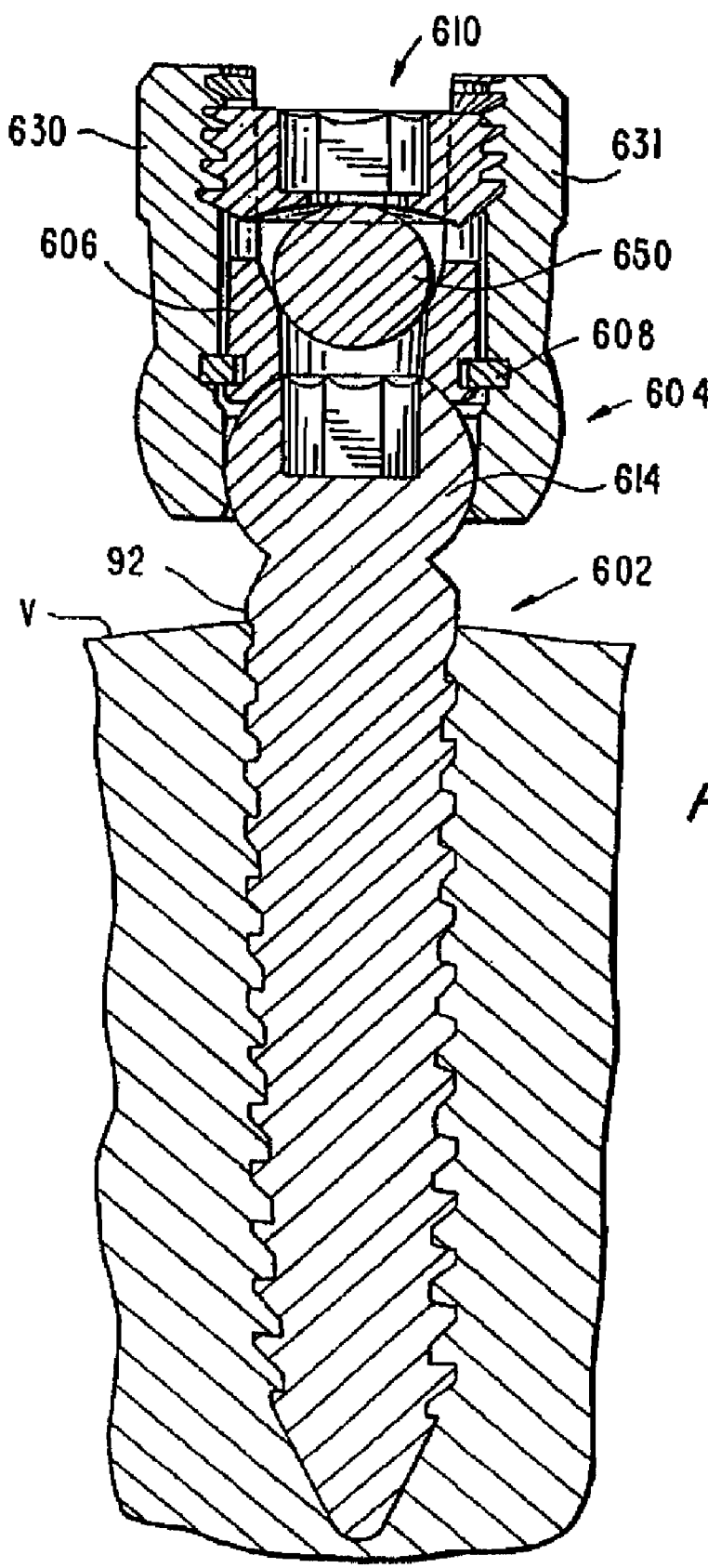
FIG. 35 is an enlarged sectional similar to FIG. 34, illustrating one embodiment of a stage of one embodiment of a method for treating the spine of a patient.

As illustrated in FIG. 35, tightening of the cap screw 610 fixes the assembly of the housing 604 with respect to the elongated member 650. In particular, the distal surface of the cap screw 610 provides a distal force against the elongated member 650, which in turn drives the spacer member 606 against the joint portion 614 of the screw portion 602, which is consequently fixed with respect to the housing 604.

If locations of the vertebrae are considered acceptable by the physician, then the fixation procedure is substantially complete once the cap screws 610 have been attached to the respective housings 604, and tightened to provide a fixed structure as between the elongated member 650 and the various fasteners 600. However, if compression or distraction of the vertebrae with respect to one another is required additional apparatus would be used to shift the vertebrae prior to final tightening all of the cap screws 610.

In the illustrated embodiment, this step is performed with a surgical instrument, such as compressor-distractor instrument 900, illustrated in FIG. 36, which is useful to relatively position bone structures in the cephcaudal direction and to fix their position with respect to one another. Thus, the compressor-distractor instrument 900 has the capability to engage two fasteners 600 and to space them apart while simultaneously tightening one of the fasteners to fix the spacing between the two vertebrae, or other bone structures. Moreover, the compressor-distractor instrument 900 may also be used to move two fasteners 600, and the vertebrae attached thereto into closer approximation and fix the spacing therebetween.

The distal tool portion 902 of the compressor-distractor instrument 900 is illustrated in FIG. 36. (Further details of the compressor-distractor apparatus is described in co-pending U.S. application Ser. No. 10/178,875, filed Jun. 24, 2002, entitled "Surgical Instrument for Moving Vertebrae," which is incorporated by reference in its entirety herein.) The distal tool portion 902 includes a driver portion 904 and a spacing member 906. The driver portion 904 has a distal end portion 908 with a plurality of wrenching flats configured to engage the recess 611 in the proximal face of the cap screw 610, and to apply torque to the cap screw. The driver portion 904 is rotatable about the longitudinal axis (indicated by arrow M) to rotate the cap screw 610 relative to the fastener 600. Accordingly, the driver portion 904 can be rotated to loosen the cap screw 610 on the fastener 600 and permit movement of the elongated member 650 connected with the vertebra relative to the fastener 600 connected with the vertebra. The cap screw 610 can also be rotated in order to tighten the cap screw 610 and clamp the elongated member 650 to the fastener 600.

The distal tool portion 902 may also include a spacing member, such as spacing member 906, which engages an adjacent fastener 600b while driver member 904 is engaged with the housing 604a to move the fastener 600b with respect to the fastener 600a. In the exemplary embodiment, spacing member 906 is a jaw portion which is pivotably mounted to move between a first position adjacent the driver portion and a second position spaced from the driver portion, as shown in FIG. 36. The distal tip 910 of the spacing member 906 is movable relative to the driver portion 904 in a direction extending transverse to the longitudinal axis.

As illustrated in FIG. 36, the spacer member 906 can be opened with respect to the driver portion 904 to space the vertebrae further apart (as indicated by arrow N). The distal portion 910 of the spacer member 906 engages the housing 604b of fastener 600b and moves fastener 600b further apart from fastener 600a to distract the vertebrae. Where the vertebrae are to be moved closer together, e.g. compressed, the spacer member 906 is closed with respect to the driver portion 904 (arrow P), as illustrated in FIG. 37. The distal portion 610 of spacer member 606 engages housing 604b of fastener 600b and moves fastener 600b towards fastener 600a. When the spacing of the vertebrae is acceptable to the physician, the cap screw 610a is tightened by the driver member 904, thereby fixing the relationship of the housing 604a with respect to elongated member 650, and thereby fixing the position of the vertebrae, or other bone structures, with respect to one another.

Once the elongated member 650 is fixed with respect to the fasteners 600, the procedure is substantially complete. The surgical instrumentation, such as the endoscope 500 is withdrawn from the surgical site. The expandable conduit 20 is also withdrawn from the site. The muscle and fascia can be allowed to close as the expandable conduit 20 is withdrawn through the dilated tissues in the reduced profile configuration. The fascia and skin incisions are closed in the typical manner, with sutures, etc. The procedure described above may be repeated for the other lateral side of the same vertebrae, if indicated.

II. Motion Preserving Stabilization Systems

Another type of procedure that can be performed by way of the systems and apparatuses described hereinabove provides stabilization of skeletal portions, e.g. adjacent vertebrae in the spine, as would be the case in more conventional fixation procedures, but advantageously preserves a degree of normal motion. A variety of system and methods that may be used to provide motion preserving stabilization, such as dynamic stabilization, are described below. The access devices and systems described above enable these systems and methods to be practiced minimally invasively.

A. Stabilization Devices Allowing Axial Motion

Figure 38:
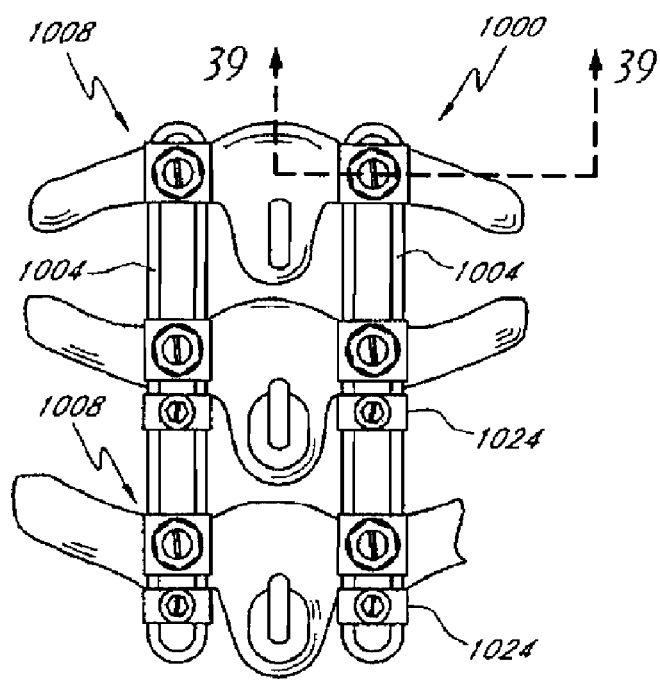
FIG. 38 is a schematic view of one embodiment of a dynamic stabilization device shown applied to a spine of a patient.
Figures 39, 40:
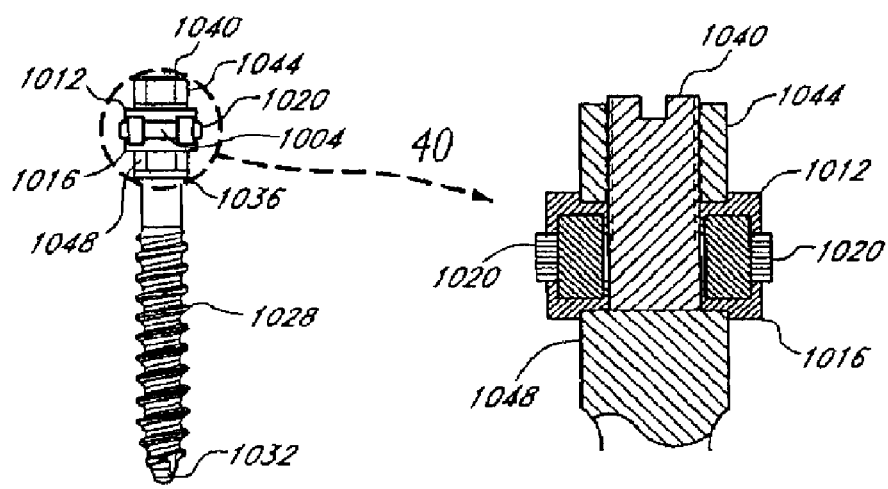
FIG. 39 is a partial cross-sectional view of a portion of the dynamic stabilization device of FIG. 38.
FIG. 40 is a detail view of a portion of the dynamic stabilization device of FIG. 38.

A first type of motion preserving stabilization device is shown in FIGS. 38-40. In the illustrated embodiment, the motion preserving stabilization device 1000 is attached on the posterior side of the spine. However, the device 1000 may be modified for use on the anterior or lateral sides of the spine, or at locations between the anterior and lateral sides, or at locations between the lateral and posterior sides, e.g., at a posterolateral location. In one embodiment, the components of this stabilization device 1000 may be fabricated from a biocompatible metal, preferably titanium or a titanium alloy. The components may also be fabricated from other metals, or other suitable materials.

In one embodiment, the stabilization device 1000 comprises a plate 1004, a plurality of fasteners 1008, a plurality of fastener clamp portions 1012 and 1016, fastener spacers 1020, and stop locks 1024, as shown in FIGS. 38-40. The stabilization device 1000 and its components are further described in the following paragraphs.

In one embodiment, the plate 1004 is the framework upon which the other components are attached. In one embodiment, the plate 1004 is an elongate member having a caudal end and a cephalad end, and defining a longitudinal axis extending from the caudal end to the cephalad end. The plate 1004 may have a slot parallel to its longitudinal axis to receive and contain the fasteners 1008. The slot advantageously allows the fasteners 1008 to be infinitely positioned axially to place it into the desired position relative to the vertebra. The plate optionally may be formed from a single piece of metal. Another approach would be to provide preformed holes, which would limit the location of the fasteners 1008 with respect to the plate 1004. The plate 1004 may be curved or otherwise shaped or configured to allow for stabilizing a spine or positioning individual vertebrae as required. Although not shown, the plate 1004 may have one or more open ends. The open ends can enable different fastener elements to be more easily inserted, and may then be closed and stiffened with one or more stop locks 1024. In another embodiment, the slot need not extend the entire length of the plate 1004, but can provide a more limited range of potential axial positions. In another embodiment, the plate 1004 may have a more rod-like shape with a hollowed out portion adapted to engage a portion of the fasteners 1008. In another embodiment, the plate 1004 may incorporate a hinge by which it is attached to at least one fastener 1008, such that the at least one fastener 1008 can move with respect to at least one other fastener 1008.

In FIG. 39, a partial cross-sectional view of one embodiment of the fastener 1008 is shown. The fastener 1008 may comprise a bone screw, such as a conventional pedicle screw similar to the fastener 600 described above. The fastener has tapered screw threads 1028 at a bone end 1032, a head which will accept a tool near a midsection 1036, and a machine screw threaded stud 1040 at a clamp end. In other embodiments, in place of a bone screw, other fastener means, such as straight pins or tapered pins, bone hooks, or others, may be used to provide attachment with the bone. In one embodiment, the fastener may also have a screwdriver slot to adjust the screw height as shown in FIG. 40.

In one embodiment, the fastener 1008 is attached to the plate 1004 via the fastener clamp portions 1012 and 1016, shown in FIG. 40 and more clearly in the detailed view shown in FIG. 40. In one embodiment, a nut 1044 clamps the upper fastener clamp portion 1012, through the plate 1004, to the lower fastener clamp portion 1016, and against a collar 1048 on the fastener 1008 to give metal-to-metal clamping. Because of the metal-to-metal clamping, the fastener 1008 does not require anti-rotational locks such as auxiliary screw clamps, cams, wedges or locking caps. The metal-to-metal clamping of the fastener 1008 to the plate 1004 provides a fully rigid bone stabilizer system. In other embodiments, other means of attaching the plate 1004 to the fasteners 1008 may be used. The fastener clamp portions 1012 and 1016 may be machined to angular shapes to allow the fastener 1008 to be attached to the plate 1004 at different angles.

In one application, spacers 1020 are selectively installed between the fastener clamp portions 1012 and 1016 to allow axial motion of the fasteners 1008 along the slot with respect to the plate 1004. This spacer 1020 installation may preserve motion between the fasteners 1008 and the plate 1004. A spacer 1020 is a piece of material with a width greater than the width of the plate 1004 placed between the fastener clamp portions 1012 and 1016, such that the fastener clamp portions 1012 and 1016 fixedly contact the spacer 1020 and not the plate 1004. In one embodiment, because of the metal-to-metal clamping through the spacer 1020, auxiliary screw clamps such as a cam, a wedge or a locking cap may not be needed. To reduce the number of small parts, the lower fastener clamp portion 1016 and the spacer 1020 may optionally be fabricated as one integral part. If desired, in a rigid installation without a spacer 1020, the nut 1044 may force the fastener clamp portions 1012 and 1016 directly against the plate 1004.

In one embodiment, the stop locks 1024 may be clamped to the plate 1004 to maintain plate rigidity, and they may serve as travel limit stops to preserve or to favor motion in one direction and to limit or eliminate it in the opposite direction. This action is sometimes referred to herein as unidirectional, dynamized action of the fasteners 1008 with respect to the plate 1004. In one embodiment, the motion of the fasteners 1008 in a cephcaudal direction is limited. In one embodiment, the stop lock 1024 includes an upper portion, a lower portion, and a screw, which assembly can be attached to the plate 1004 in a similar manner to the fastener clamp portions 1012 and 1016 described above. The stop locks 1024 may be preloaded before tightening the stop lock screw. The stop locks 1024 may also utilize springs or other force generating means to maintain compression on the vertebra/graft interface.

FIG. 38 shows that two stabilization devices 1000 can be used in conjunction on either side of the spinous processes, extending across three vertebrae. The stabilization device 1000 may alternatively be applied with one or more plates, and they may extend across two or more vertebrae.

In one embodiment, the unidirectional, dynamized action between the fasteners 1008 and plate 1004 preserves subsidence of the vertebrae, motion of an upper vertebra in a caudal direction. Among other advantages, this allows for graft resorption and settling. It also provides improved fusion conditions and prevents graft distraction. The stabilization device 1000 can also provide stress shielding to the stabilized vertebrae along other directions, including: rotation causing axial shear; lateral bending causing contralateral distraction; flexion causing posterior distraction; extension causing anterior distraction; horizontal force causing translation shear; and extension causing distraction.

Further details of structures that provide support and stability while preserving motion may be found in U.S. patent application Ser. No. 09/846,956 filed on May 1, 2001, published as U.S. Patent Application No. 2001/0037111 on Nov. 1, 2001, which is hereby incorporated by reference in its entirety.

Figure 41:
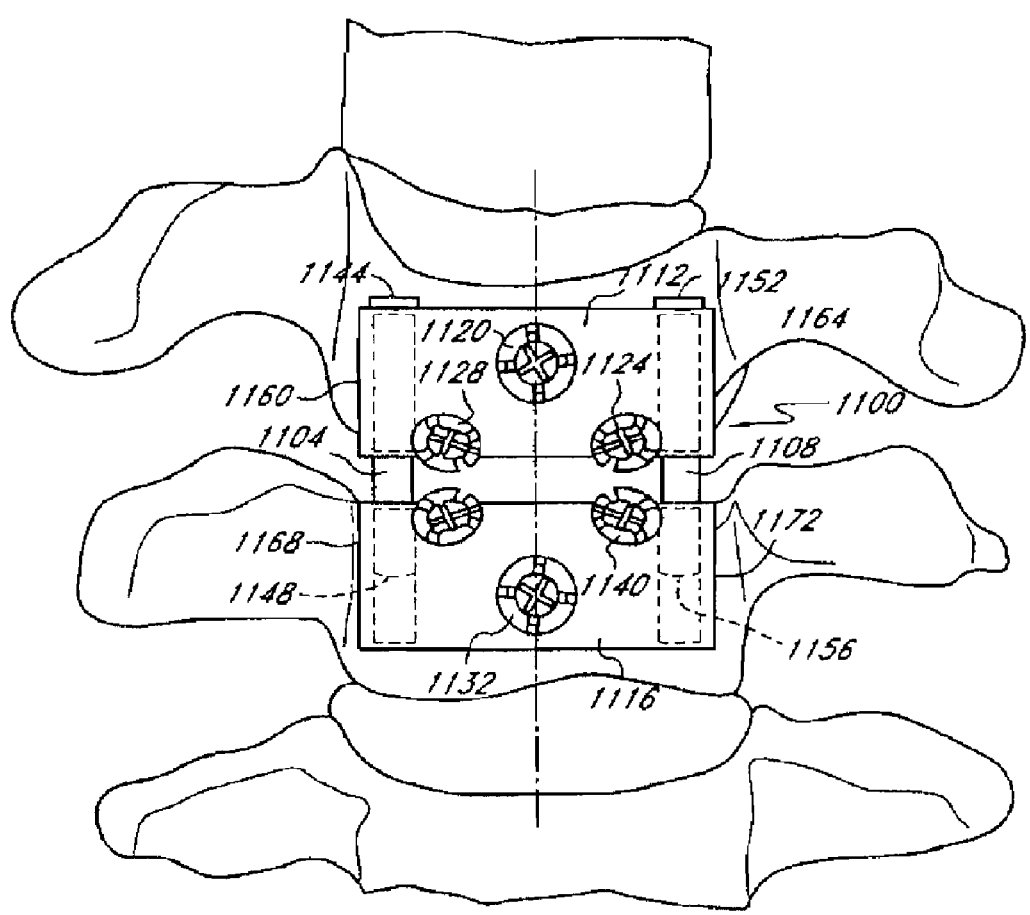
FIG. 41 is an elevation view illustrating one embodiment of a dynamic stabilization device applied to a human spine.

FIG. 41 shows another, similar embodiment of a motion preserving stabilization device 1100, which includes rods 1104, 1108 interconnected by a pair of plates 1112, 1116 each secured to a respective vertebra by multiple fasteners. In one embodiment, although the FIGURE shows an anterior insertion, the stabilization device 1100 is configured to be secured to the posterior side of the spine. The device 1100 may also be modified for use on the anterior or lateral sides of the spine, or at a location between the anterior and lateral sides, or at a location between the lateral and posterior sides, e.g., posterolateral.

In one embodiment, the stabilization device 1100 comprises a pair of surgically implantable rods 1104 and 1108. The stabilization device 1100 may also include first and second plates 1112 and 1116, which engage the rods 1104 and 1108; three fasteners 1120, 1124, and 1128 for connecting the first plate 1112 with the first vertebra V1; and three fasteners 1132, 1136, and 1140 for connecting the second plate 1116 with the second vertebra V2.

The first rod 1104 is made of a suitable biocompatible material, such as titanium or stainless steel. In one embodiment, the first rod 1104 has an elongate cylindrical configuration and has a circular cross section taken in a plane extending perpendicular to the longitudinal central axis of the first rod. The first rod 1104 may also have a smooth outer surface. A first end portion of the first rod 1104 may comprise a cap 1144. The first rod 1104 may also have a second end portion 1148 opposite from the cap 1144. In one embodiment, the rod 1104 has a uniform diameter of about three (3) millimeters throughout its extent except at the cap 1144.

The second rod 1108 may be substantially identical to the first rod 1104. In one embodiment, the second rod 1108 has a first end portion comprising a cap 1152. The second rod 14 may also have a second end portion 1156 opposite from the cap 1152. In one embodiment, the rods 1104 and 1108 are bendable to a desired configuration to conform to a desired curvature of the spinal column. In a preferred embodiment, the rods 1104 and 1108 together have sufficient strength and rigidity to maintain the vertebrae V1 and V2 in a desired spatial relationship.

In one embodiment, the rods 1104 and 1108 have a length sufficient to enable them to span at least the two vertebrae V1 and V2. The length of the rods 1104 and 1108 will depend upon the condition to be corrected and the number of vertebrae to be held in a desired spatial relationship relative to each other by the stabilization device 1100. If more than two vertebrae are to be held in a desired spatial relationship relative to each other by the stabilization device 1100, the rods 1104 and 1108 could be longer, and more than two plates, such as the plates 1112 and 1116, may be used.

The first plate 1112 may be made of any suitable biocompatible material, such as titanium or stainless steel. In one embodiment, the first plate 1112 includes a main body portion. The main body portion of the first plate 1112 may have a planar outer side surface for facing away from the first vertebra V1. The first plate 1112 may have an arcuate inner side surface for facing toward the first vertebra V1. The inner side surface of the first plate 1112 may engage the surface of the first vertebra V1 when the first plate is connected with the first vertebra as described below.

The main body portion of the first plate 1112 may also have a central portion which extends laterally between a first side portion 1160 and a second side portion 1164 of the first plate 1112. Because the inner side surface of the first plate 1112 has an arcuate configuration, the central portion of the first plate 1112 may be relatively thin as compared to the first side portion 1160 and to the second side portion 1164.

In one embodiment, the main body portion of the first plate 1112 also has first and second end portions 1168 and 1172. The first end portion 1168 of the first plate 1112 may include a planar first end surface of the first plate 1112. The second end portion 1172 may include a planar second end surface of the first plate 1112. The second end surface may extend parallel to the first end surface.

In one embodiment, a first rod passage is formed in the first side portion 1160 of the first plate 1112. The first rod passage is an opening that extends between the first and second end surfaces of the first plate 1112, in a direction parallel to the planar outer side surface of the first plate 1112. The first rod passage may be defined by a cylindrical surface and tapered pilot surfaces and at opposite ends of the cylindrical surface. The diameter of the cylindrical surface is optionally slightly greater than the diameter of the first rod 1104, so that the first rod 1104 and the first plate 1112 can be relatively movable.

In one embodiment, the second side portion 1164 of the first plate 1112 is a mirror image of the first side portion 1160. A second rod passage is formed in the second side portion 1164 of the first plate 1112. The second rod passage is an opening that extends between the first and second end surfaces of the first plate 1112, in a direction parallel to the planar outer side surface of the first plate 1112. The second rod passage extends parallel to the first rod passage. In one embodiment, the second rod passage is defined by a cylindrical surface and tapered pilot surfaces at opposite ends of the cylindrical surface. The diameter of the second rod passage is preferably the same as the diameter of the first rod passage. The diameter of the cylindrical surface is optionally slightly greater than the diameter of the second rod 1108, so that the second rod 1108 and the first plate 1112 can be relatively movable.

In one embodiment, a circular first fastener opening extends through the central portion of the first plate 1112. The first fastener opening has an axis that extends perpendicular to the plane of the outer side surface of the first plate 1112. The first fastener opening may be partially defined by a larger diameter cylindrical surface, which extends from the outer side surface of the first plate 1112 in a direction into the material of the central portion of the first plate 1112. The cylindrical surface is centered on the axis of the first fastener opening. The first fastener opening may also be partially defined by a smaller diameter cylindrical surface, which extends from the inner side surface of the first plate 1112 in a direction into the material of the central portion of the first plate to a location spaced radially inward from the larger diameter cylindrical surface. This smaller diameter cylindrical surface may also be centered on the axis of the first fastener opening 90.

In one embodiment, an annular shoulder surface extends radially (relative to the axis of the first fastener opening 90) between the larger and smaller diameter cylindrical surfaces. The shoulder surface and the larger diameter cylindrical surface define a recess in the outer side surface of the first plate 1112.

The main body portion of the first plate 1112 may also include a circular second fastener opening fanned at a location adjacent to, but spaced apart from, the first rod passage in the first side portion 1160 of the first plate 1112. The second fastener opening may extend through both the second end surface of the first plate 1112 and the outer side surface of the first plate 1112. In one embodiment, the second fastener opening is partially defined by a larger diameter cylindrical surface, a smaller diameter cylindrical surface and an annular shoulder surface, in a configuration similar to that of the first fastener opening.

The main body portion of the first plate 1112 may also include a circular third fastener opening formed at a location adjacent to, but spaced apart from, the second rod passage in the second side portion 1164 of the first plate 1112. The third fastener opening may extend through both the second end surface of the first plate 1112 and the outer side surface of the first plate 1112. In one embodiment, the third fastener opening is partially defined by a larger diameter cylindrical surface, a smaller diameter cylindrical surface and an annular shoulder surface, in a configuration similar to that of the first fastener opening.

The second plate 1116 may be generally similar in configuration to the first plate 1112, with rod passages disposed on both sides. The second plate 1116 may be configured, however, so that the head ends of the fasteners 1136, 1140 received in certain fastener openings in the second plate 1116 are engageable with the rods 1104 and 1108 disposed in rod passages in the second plate 1116. This engagement can block movement of the second plate 1116 relative to the rods 1104 and 1108, in a manner described below.

One or both of the fastener openings receiving the fasteners 1136 or 1140 may be partially defined by a larger diameter cylindrical surface which extends from the outer side surface of the second plate 1116 in a direction into the material of the first side portion of the second plate. This larger diameter cylindrical surface is centered on an axis of the fastener opening. The larger diameter cylindrical surface may also intersect the cylindrical surface that defines a rod passage in the second plate 1116. Thus, the fastener opening overlaps a portion of a rod passage.

In one embodiment, the fasteners 1120, 1124, 1128, 1132, 1136, and 1140, which connect the first plate 1112 with the first vertebra V1, and the second plate 1116 with the second vertebra V2, may be identical to each other. These fasteners 1120, 1124, 1128, 1132, 1136, 1140 may comprise bone screws, such as conventional pedicle screws similar to the fastener 600 described above. In other embodiments, in place of a bone screw, other fastener means, such as straight pins or tapered pins, bone hooks, or others, may be used to provide attachment with the bone.

When the second plate 1116 is connected with the second vertebra V2, the fasteners 1132, 1136 and 1140 secure the second plate and the second vertebra. The outer fasteners 1136 and 1140 may also serve to interlock the second plate 1116 with the rods 1104 and 1108, by moving into engagement with the rods 1104 and 1108, respectively, when each fastener is fully screwed into a respective vertebra. In one embodiment, the engagement between the fasteners 1136 and 1140 and the rods 1104 and 1108 blocks movement of the fasteners 1136 and 1140 relative to the rods. As a result, the fasteners 1136 and 1140 may also block movement of the second plate 1116 relative to the rods 1104 and 1108. Other means of blocking the movement of the second plate 1115 relative to the rods 1104 and 1108 are well known to those of skill in the art.

In one embodiment, the first plate 1112, in contrast, preserves motion relative to the rods 1104 and 1108, because the second and third fastener openings are spaced apart from the first plate's rod passages. In a preferred embodiment, the first plate 1112 is thus movable relative to the second plate 1116. In other embodiments, this motion preserving stabilization system 1100 may consist of two or more movable plates like 1112, with no fixed plates like 1116.

Accordingly, the first vertebra V1 may be movable vertically downward relative to the second vertebra V2. This relative movement allows for the maintaining of a load on bone graft placed between the vertebrae V1 and V2. If the first plate 1112 were not movable vertically downward relative to the second plate 1116, then the distance between the vertebrae V1 and V2 would be fixed. If bone graft were placed between the vertebrae V1 and V2 and the bone graft resorbed sufficiently, the bone graft could possibly shrink out of engagement with one or both of the vertebrae V1 and V2. Allowing relative movement of the plates 1112 and 1116 can help to maintain a load on bone graft placed between the vertebrae V1 and V2 and maintains the vertebrae in contact with the bone graft to facilitate bone growth.

The caps 1144 and 1152 on the rods 1104 and 1108, respectively, limit movement of the first vertebra V1 in a direction away from the second vertebra V2. This helps to maintain the vertebrae V1 and V2 in contact with the bone graft.

The stabilization device 1100 can also provide stress shielding to the stabilized vertebrae along other directions, including: rotation causing axial shear; lateral bending causing contralateral distraction; flexion causing posterior distraction; extension causing anterior distraction; horizontal force causing translation shear; and extension causing distraction.

Further details of structures that provide support and stability while preserving motion may be found in U.S. Pat. No. 6,036,693 filed on Nov. 30, 1998, which is hereby incorporated by reference in its entirety.

B. Stabilization Device Having a Flexible Elongate Member

Figure 42:
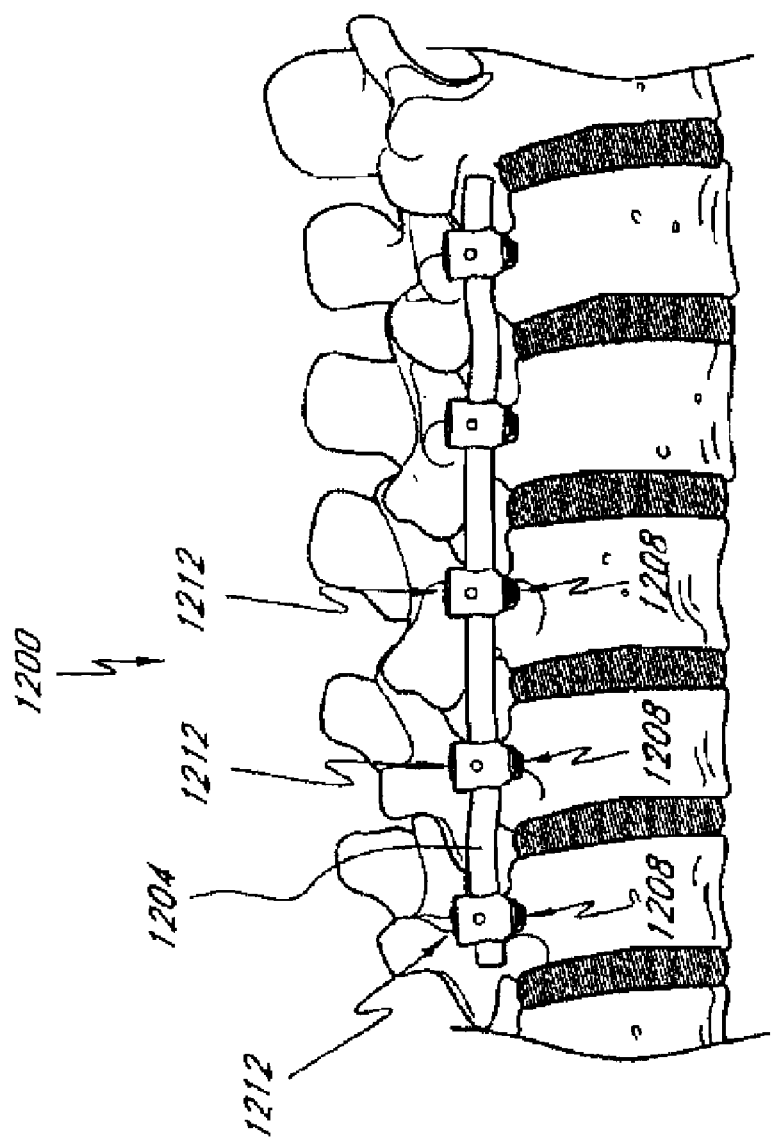
FIG. 42 is a lateral elevation view illustrating one embodiment of a dynamic stabilization device applied to a human spine.

FIG. 42 shows another embodiment of a motion preserving stabilization device 1200. While the FIGURE shows one stabilization device 1200, extending across five vertebrae. As discussed more fully below, multiple stabilization devices 1200 may be applied to a spine in parallel, and may extend across more or fewer vertebrae. The stabilization device 1200 includes an elongate member 1204 secured to a plurality of fasteners 1208. In one embodiment, each fastener 1208 is engaged to a respective one of the vertebrae V1, V2, V3, V4, V5. A coupling member 1212 is engaged to each of the fasteners 1208 with the elongate member 1204 positioned between each fastener 1208 and its respective coupling member 1212.

It should be understood that the stabilization device 1200 may be utilized in all regions of the spine, including the cervical, thoracic, lumbar, lumbo-sacral and sacral regions of the spine. Additionally, although the stabilization device 1200 is shown in FIG. 42 as having application in a posterior region of the spine, it may alternatively be applied in other surgical approaches and combinations of surgical approaches to the spine such that one or more stabilization devices 1200 are attached to the anterior, antero-lateral, lateral, and/or postero-lateral portions of the spine.

In one embodiment, the stabilization device 1200 allows at least small degrees of spinal motion between the vertebrae to which it is attached, since the stabilization device 1200 includes an elongate member 1204 that is at least partially flexible between adjacent fasteners 1208. It should be understood that the stabilization device 1200 can be used in conjunction with fusion or non-fusion treatment of the spine. In one embodiment, the elongate member 1204 is a tether made from one or polymers, such as, for example, polyester or polyethylene; one or more superelastic metals or alloys, such as, for example, nitinol; or from resorbable synthetic materials, such as, for example suture material or polylactic acid. It is further contemplated that the elongate member 1204 may have elasticity such that when tensioned it will tend to return toward its pre-tensioned state. In other embodiments, the shape and size of the elongate member 1204 can be modified to adjust its elasticity and flexibility along different axes.

The fasteners 1208 and coupling members 1212 described herein may be employed with the shown stabilization device 1200. In addition, it is contemplated that the fasteners 1208 and coupling members 1212 described herein may be employed in isolation or in devices that include two or more coupling members 1212 and fasteners 1208. Examples of other devices include: one or more elongate members 1204 extending laterally across a vertebral body; one or more elongate members 1204 extending in the anterior-posterior directions across a vertebral body; one or more elongate members 1204 wrapped around a vertebral body; and combinations thereof. Further examples include application of the fasteners 1208 and coupling members 1212 of the present disclosure with bony structures in regions other than the spinal column.

In one embodiment, a fastener 1208 may comprise a bone screw, such as a conventional pedicle screw similar to the fastener 600 described above. In other embodiments, in place of a bone screw, other fastener means, such as straight pins or tapered pins, bone hooks, or others, may be used to provide attachment with the bone. Similarly, a coupling member 1212 may comprise a cap screw similar to the cap screw 610 described above. In another embodiment, the coupling member 1212 comprises a threadable portion to threadably engage the fastener 1208, and a penetrating element to penetrate the elongate member 1204. In other embodiments, the coupling member 1212 may comprise another means of engaging a fastener 1208 and the elongate member 1204.

The motion preserving elongate member 1204 of this stabilization device 1200 enables adjacent vertebrae to move relative to each other depending on the elongate member's 1204 flexibility, while partially reproducing the restorative forces of a healthy spine. Moreover, the stabilization device 1200 may be stiffer along the direction of the longitudinal axis, reducing the compressive forces imposed upon the intervertebral regions, and providing support for the spine's load-bearing functions.

Further details of structures that provide support and stability while preserving motion may be found in U.S. patent application Ser. No. 10/013,053 filed on Oct. 30, 2001, published as U.S. Patent Publication No. 2003/0083657 on May 1, 2003, and U.S. patent application Ser. No. 09/960,770 filed on Sep. 21, 2001, published as U.S. Patent Publication No. 2002/0013586 on Jan. 31, 2002, which are hereby incorporated by reference in their entirety.

C. Stabilization Device with a Jointed Link Rod

Figure 43:
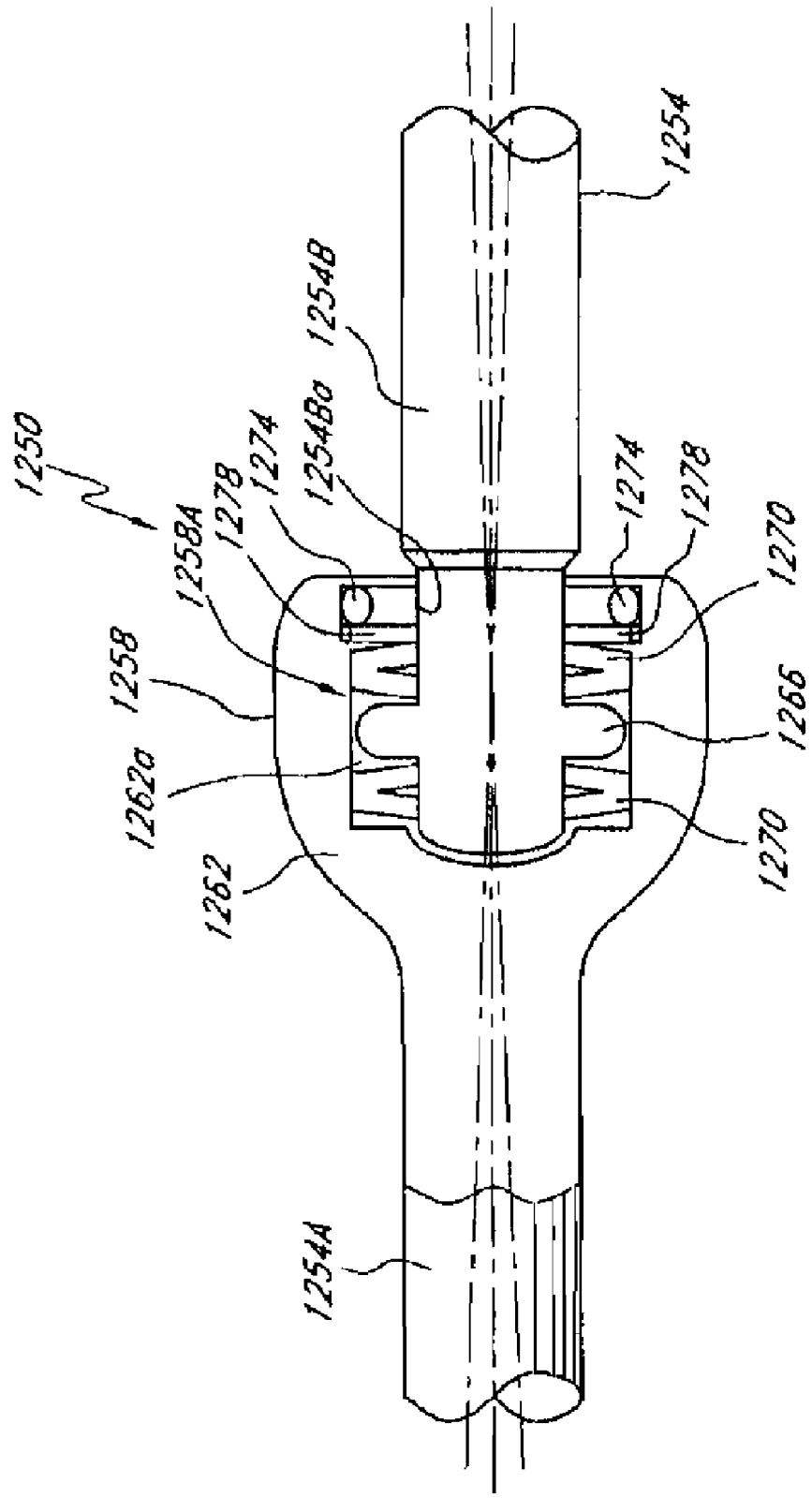
FIG. 43 is a detail view illustrating one embodiment of a dynamic stabilization device.

FIG. 43 illustrates a portion of another embodiment of a stabilization device 1250. In one embodiment, the stabilization device 1250 is configured to be secured to the posterior side of the spine. However, the device 1250 may be modified for use on the anterior or lateral sides of the spine, or at a location between the anterior and lateral sides, or at a location between the lateral and posterior sides, e.g., posterolateral.

In the example shown in FIG. 43, a set of fasteners connected to at least two vertebrae may be interconnected by a link rod 1254 comprising at least two rigid segments 1254A and 1254B, which are interconnected by means of a damper element 1258 interposed between their facing free ends, so as to oppose elastic resistance between the segments 1254A and 1254B with amplitude that may be controlled not only in axial compression and traction a, but also in angular bending b.

A single link rod 1254 may include a plurality of dampers 1258 disposed between the vertebrae. Also, the link rod 1254 may advantageously be cut to a selected length and curved to a selected radius.

As can be seen more clearly in FIG. 43, the damper element 1258 may be made up of two elastically deformable members 1258A disposed around the free end of a pin 1254Ba extending from one of the segments 1254B constituting the rod 1254. The pin 1254Ba may be engaged inside a housing 1262a formed in a blind sleeve or cage 1262 made at the free end 1254Aa of the other link segment 1254A. In one embodiment, the damper element 1258 comprises a rigid piston 1266 formed on the pin 1254Ba to constitute a joint 1266 making multidirectional relative pivoting possible between the cage 1262 and the pin 1254Ba, at least about axes contained in a plane perpendicular to the longitudinal axis x-x' of the damper element 1258 when the pin 1254Ba and the cage 1262 are in alignment.

In one embodiment, the resulting joint 1266 is of the ball-and-socket type that also allows the cage 1262 to rotate relative to the pin 1254Ba about the axis x-x'. The joint 1266 may comprise a collar projecting radially from the pin 1254Ba and having an outside surface with a rounded profile that is designed to come into contact with the inside surface of the housing 1262a in the cage 1262. In the embodiment shown in FIG. 43, the collar 1266 is an integral part of the pin 1254Ba, although in other examples, the collar 1266 may comprise a separate ring that is fixed on the pin 1254Ba.

The collar 1266 is disposed relative to the pin 1254Ba in such a manner as to receive thrust on both of its lateral faces from two sets of spring washers 1270 each in the form of a pair of facing frustoconical cups of identical diameter stacked on the pin 1254Ba. The washers 1270 and the joint 1266 occupy at least part of the circular section housing 1262a, whose end wall constitutes a compression abutment for one of the elastically deformable members 1258A. It should be observed that the spring washers 1270, which are also known as "Belleville" washers, can be replaced by other spring-like elements, such as elastomer rings.

In one embodiment, the housing 1262a of the cage 1262 is closed by a first washer 1274 secured to the cage 1262 and having an inside face against which there bears a second washer 1278 secured to the pin 1254Ba. The deformable members 1258A may be placed freely on the pin 1254Ba between the second washer 1278 and the end wall of the housing 1262a. For example, the first washer 1274, which constitutes an axial abutment, can be implemented in the form of a threaded ring screwed into tapping made inside the housing from its outer end, thereby making it possible to adjust the extension position of the damper. It should be observed that the second washer 1278, which is secured to the pin 1254Ba, constitutes a bearing surface for an elastically deformable member 1258A. This second washer 1278 can serve as an abutment for the damper in axial traction. This second washer 1278 thus makes it possible to exert compression force on the deformable member without damaging it. In addition, according to an advantageous characteristic, the second washer 1278 can be made of a material that is identical to that constituting the elastically deformable member, so as to make it possible to control the friction which appears between the second washer 1278 and the elastically deformable member 1258A.

The elastically deformable members 1258A are maintained with axial clearance that makes it possible, when they deform elastically, to accommodate relative axial movements in compression and traction between the pin 1254Ba and the cage 1262. For example, it is possible to obtain axial compression or traction having a value of 0.8 mm. In addition, the elastically deformable members 1258A may be mounted to allow multidirectional relative pivoting between the pin 1254Ba and the cage 1262. The washers 1270 may therefore be mounted inside the housing 1262a with clearance relative to the inside wall of the housing.

In one embodiment, the damper element 1258 includes an angular abutment for limiting the multidirectional relative pivoting to a determined value having an amplitude of about 4 degrees. Thus, as can be seen more clearly in FIG. 43, the displacement b of the pin 1254Ba in the cage 1262 relative to its normal, aligned position is 2 degrees. In the embodiment shown, the angular abutment is provided by the housing 1262a against which the pin 1254Ba comes into abutment, which pin 1254Ba has a predetermined amount of radial clearance relative to the housing 1262a to enable relative pivoting to take place through the predetermined angle b. Thus, the pin 1254Ba presents radial clearance both between its collar 1266 and the housing 1262a, and between its free end and a blind recess 1262b extending the housing 1262a. Relative pivoting between the cage 1262 and the pin 1254Ba is thus limited by implementing two angular abutments defined by the co-operation firstly between the collar 1266 and the housing 1262a, and secondly between the free end of the pin 1254Ba and the blind recess 1262b. It should be observed that the two abutments constituted in this way are set up in opposition about the axis x-x'. This allows limited bending to be obtained between the cage and the pin in all directions of angular displacement.

This motion preserving link rod 1254 of this stabilization device 1250 enables adjacent vertebrae to move relative to each other depending on the flexibility of the incorporated joint 1266, while partially reproducing the restorative forces of a healthy spine. Moreover, the stabilization device 1250 may be stiffer along the direction of the longitudinal axis, reducing the compressive forces imposed upon the intervertebral regions, and providing support for the spine's load-bearing functions.

Further details of structures that provide support and stability while preserving motion may be found in U.S. Pat. No. 6,241,730 filed on Nov. 27, 1998, which is hereby incorporated by reference in its entirety.

D. Stabilization Device with a Spring Element

Figure 44:
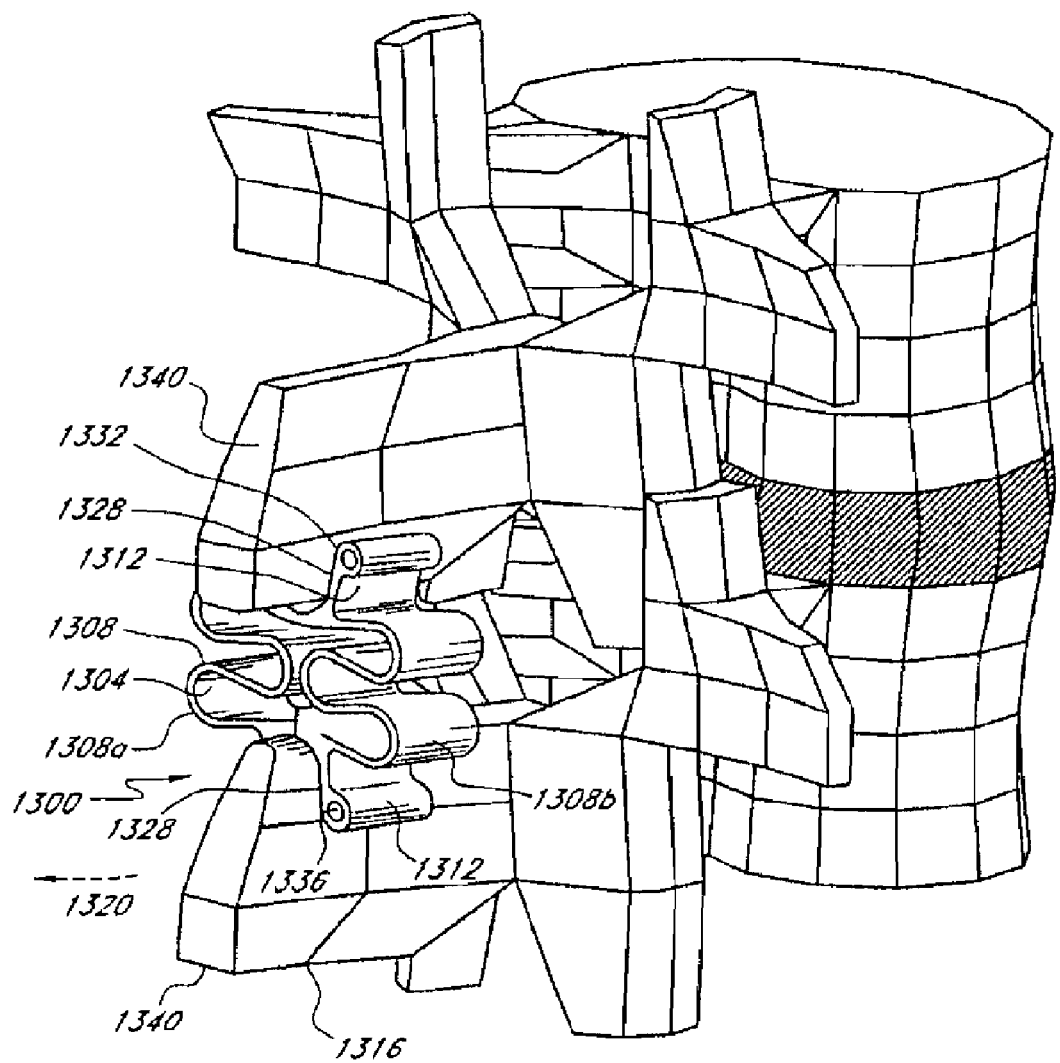
FIG. 44 is a perspective view illustrating one embodiment of a dynamic stabilization device applied to a human spine.

FIG. 44 illustrates another embodiment of a stabilization device 1300. In one embodiment, the stabilization device 1300 is configured to be secured to the posterior side of the spine. However, the device 1300 may be modified for use on the anterior or lateral sides of the spine, or at a location between the anterior and lateral sides, or at a location between the lateral and posterior sides, e.g., posterolateral.

In one embodiment, the body 1304 of the stabilization device 1300 comprises a leaf spring 1308 in the form of a closed loop and in one piece with fasteners 1312. The stabilization device 1300 is preferably made of titanium or titanium alloy, although other biocompatible materials may be used. In one embodiment, the spring 1308 defines two leaf spring parts 1308a, 1308b extending parallel to each other in the alignment direction 1316. The generatrix 1320 extends from front to rear, and defines the moving straight line, whose path defines the planar leaf spring 1308 of the stabilization device 1300.

The two parts 1308a, 1308b of the spring may be symmetrical to each other with respect to a median plane passing through the axis 1316. Each spring part forms a plurality of successive U-shapes alternately oriented in opposite directions in a plane perpendicular to the generatrix 1320. In one embodiment, each part 1308a, 1308b has three of these U-shapes. The U-shapes nearest the fasteners 1312 have their base facing towards the outside of the stabilizing device 1300, and the middle U-shape of each part has its base facing towards the inside of the stabilizing device 1300. Each part

1308a, 1308b therefore forms an undulation or zigzag. To be more precise, the general shape of this embodiment is that of an inverted M.

In one embodiment, each fastener 1312 comprises two jaws 1328, which are symmetrical to each other with respect to the median plane, generally flat in shape and have a generatrix parallel to the generatrix 1320. The two jaws 1328 face each other. Their facing faces have profiled teeth 1332. Each jaw has a passage 1336 for inserting a tool for maneuvering the jaw and whose axis is parallel to the generatrix 1320. The bases of the jaws 1328 extend at a distance from each other from one end of the spring 1308. The two jaws 1328 are mobile elastically relative to each other. At rest they diverge from their base.

To fit the stabilizing device 1300, the jaws 1328 of each fastener 1312 may be forced apart using tools inserted into the passages 1336. The stabilizing device 1300 may then be placed as shown in FIG. 44 so that each spinous process 1340 is between the respective jaws 1328. The jaws are then released so that they grip the processes and are anchored to them by their teeth 1332.

The leaf spring parts 1308a, 1308b may extend laterally beyond the spinous processes 1340. They can be configured to impart a low stiffness to them. A stabilizing device 1300 may optionally be fabricated by spark erosion from a mass of metal; this fabrication process being particularly simple because of the profile of the device 1300. In one embodiment, this stabilizing device 1300 has a relatively low stiffness for lateral flexing of the body, i.e. flexing about an axis parallel to the generatrix 1320. It has a high stiffness for flexing of the body from front to rear, i.e. flexing about an axis perpendicular to the direction 1316 and to the generatrix 1320. In other embodiments, the shape of the spring 1308 can easily be modified to increase or reduce at least one of the stiffnesses referred to above, independently of the volume available between the processes 1340.

Although the spring element 1308 resists deformation proportionally to an effective spring constant, its structure also preserves some amount of motion between adjacent vertebrae. In one embodiment, the spring 1308 may be configured to allow some proportion of the axial forces to be imposed upon the intervertebral region, while providing restorative forces. This motion preserving device thereby facilitates healing and shields the spine from some postoperative stress.

Further details of structures that provide support and stability while preserving motion may be found in U.S. Pat. No. 6,440,169 filed on Jan. 27, 1999, which is hereby incorporated by reference in its entirety.

E. Stabilization Devices Comprising an Array of Elongated Elements

As discussed above, dynamic stabilization of the spine stabilizes a diseased or damaged motion segment while preserving at least a portion of the natural motion of the segment. Stabilization can augment the spine, restoring support of or natural stiffness to an unstable motion segment. A motion segment includes, for example, a disk, or a disk and a vertebra, or a pair of vertebrae and a disk sandwiched between the pair, or a larger portion of the spine.

Figure 45:
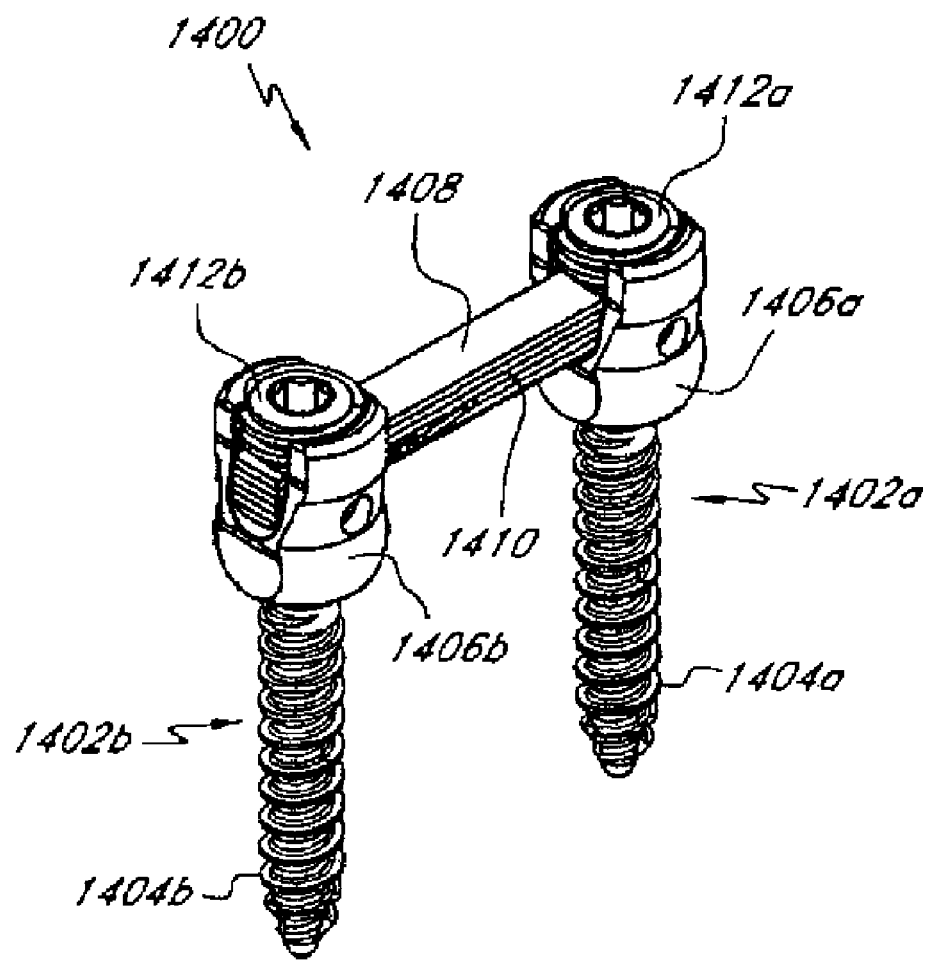
FIG. 45 is a perspective view illustrating one embodiment of a dynamic stabilization device or stabilization system having a longitudinal member comprising a plurality of thin sheets.

FIG. 45 illustrates an embodiment of a dynamic stabilization apparatus 1400. In one embodiment, the stabilization apparatus 1400 is configured to be secured to the posterior side of the spine. The apparatus 1400 may also be modified for use on the anterior or lateral sides of the spine, or at a location between the anterior and lateral sides, or at a location between the lateral and posterior sides, e.g., posterolateral. The stabilization apparatus 1400 may be used in one-level and two-level spinal fixation or fusion procedures and is capable of being implanted in a minimally invasive technique. Analogously to the procedure illustrated in FIG. 31, the components of the dynamic stabilization apparatus 1400 may be inserted through an access device, such as the expandable conduit 20, into the operative space 90 defined at least partially by the skirt portion 24 of the expandable conduit 20. One or more stabilization apparatuses 1400 may be used in the operative space 90. As with the other devices for dynamic stabilization described herein, the stabilization apparatus 1400 can be applied through the other access devices described herein or in connection with an open or mini-open procedure.

Figures 48, 49:
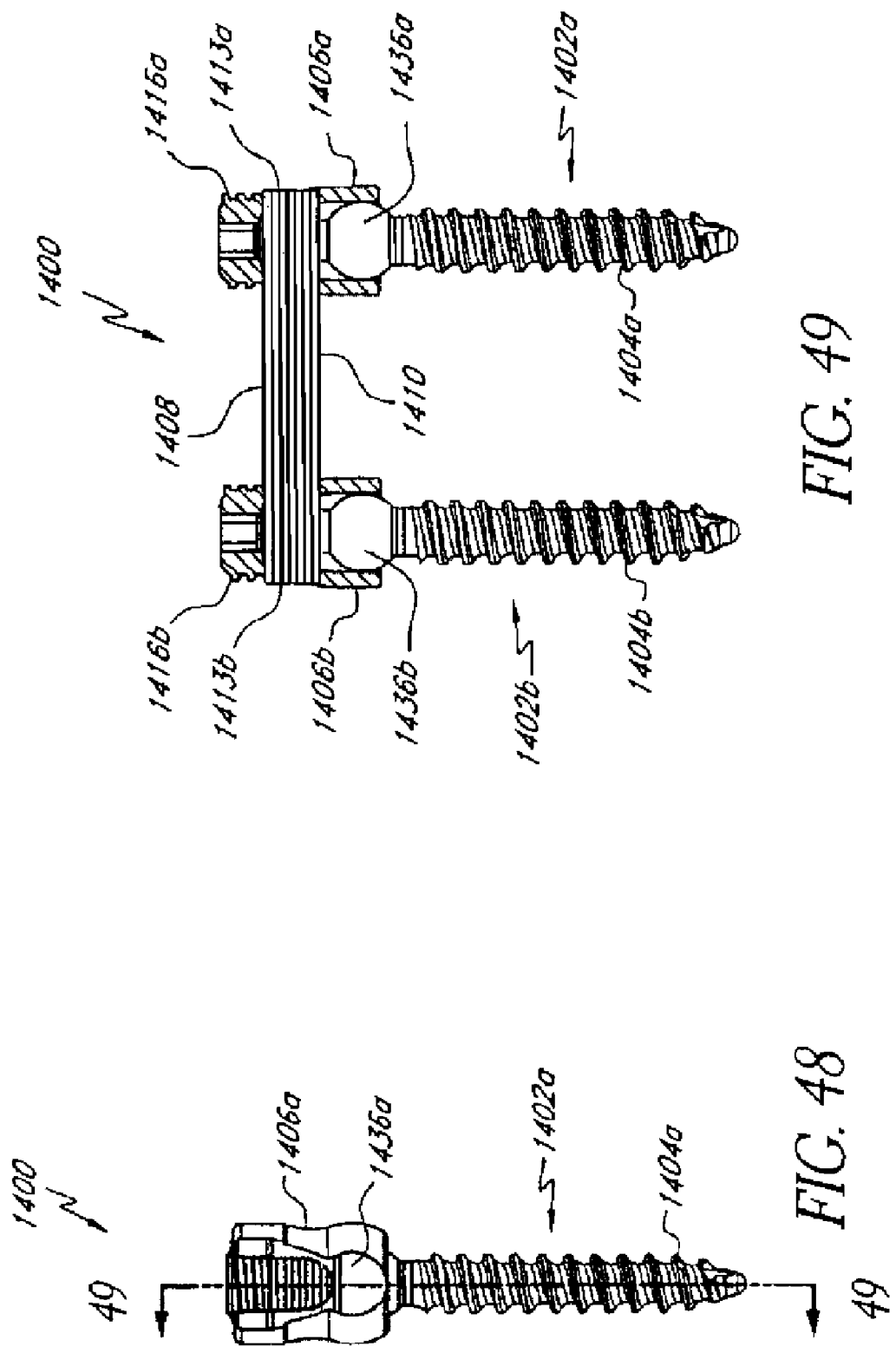
FIG. 48 is an end view of the dynamic stabilization device of FIG. 45.
FIG. 49 is a partial cross-section view of the dynamic stabilization device of FIG. 48 taken along section plane 49-49.

In one embodiment illustrated in FIG. 45, the dynamic stabilization apparatus 1400 comprises a first fastener 1402a and a second fastener 1402b. The first fastener 1402a has a threaded shank 1404a for engaging a portion of a vertebra $V_1$. The second fastener 1402b has a threaded shank 1404b for engaging a portion of a vertebra $V_2$. The vertebrae $V_1$ and $V_2$ may be adjacent or may be separated by one or more vertebrae. The fasteners 1402a and 1402b each have enlarged heads in one embodiment (shown in FIGS. 48-49). The threaded shanks 1404a, 1404b can take any suitable form, for example, including threads that are self-tapping and therefore can be advanced into a hole in a vertebra (e.g., a pedicle) that has not been pre-threaded. In some techniques, the threaded shanks 1404a, 1404b can be inserted into pedicle tunnels that have been pre-threaded. Also, although the dynamic stabilization device 1400 includes fasteners 1402a, 1402b that have threaded shanks 1404a, 1404b, other embodiments provide at least one fastener that can be coupled with a vertebrae in another manner, for example, without requiring threads.

Figure 52:
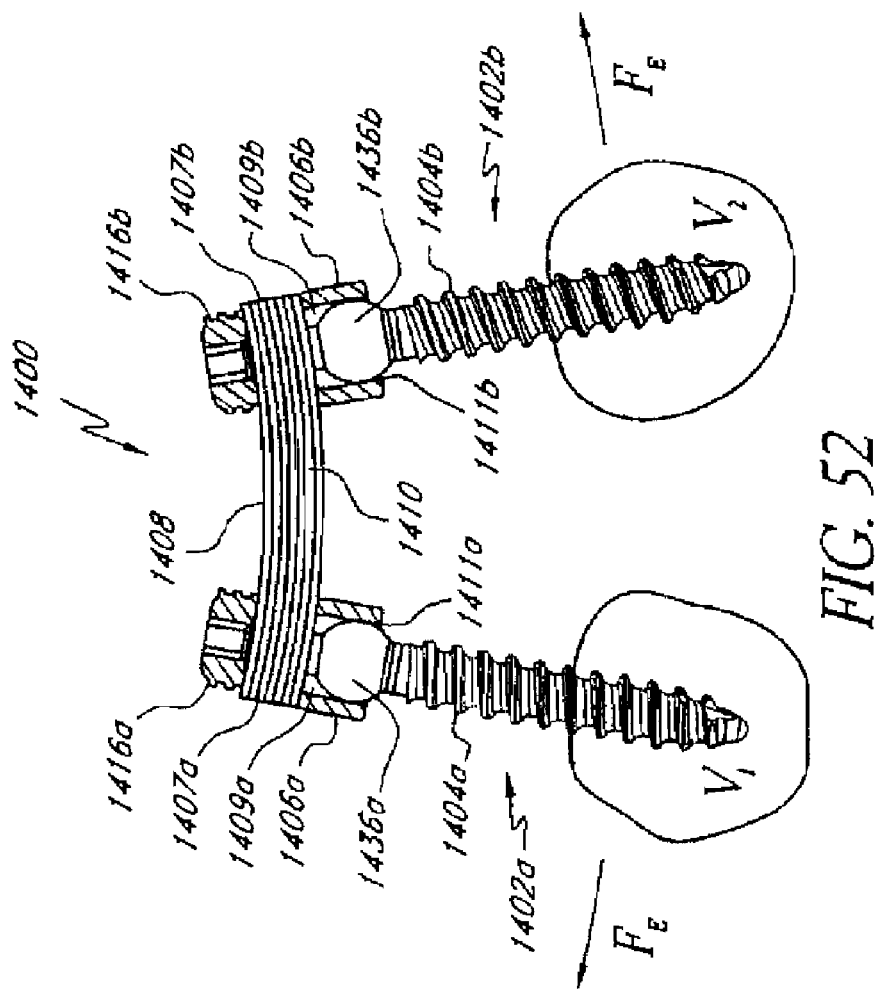
FIG. 52 is a partial cross-section view of the dynamic stabilization device of FIG. 51 taken along section plane 52-52.

The stabilization apparatus 1400 comprises a first housing 1406a and a second housing 1406b. As shown in FIG. 45 and FIG. 52, each of the housings 1406a and 1406b has a first passage 1407a, 1407b and a second passage 1409a, 1409b with transversely oriented longitudinal axes. The first fastener 1402a extends through an opening 1411a into the second passage 1409a of the housing 1406a. Similarly, the second fastener 1402b extends through an opening 1411b into the second passage 1409b of the housing 1406b.

Figure 46:
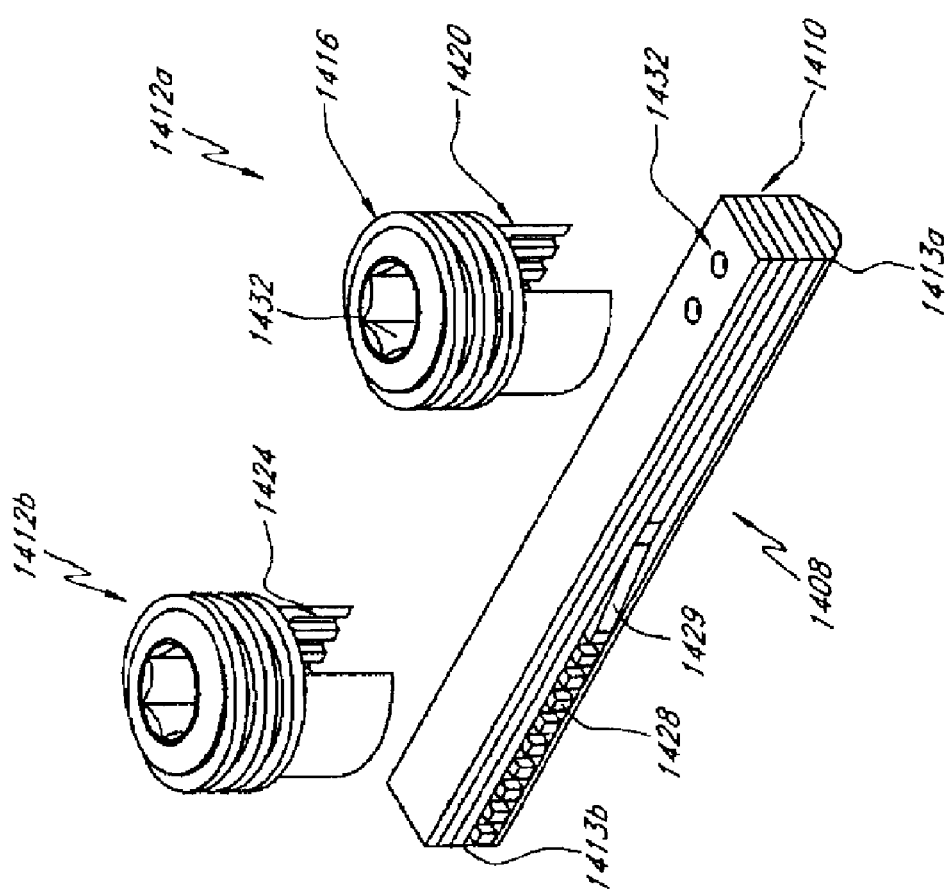
FIG. 46 is an exploded perspective view of the longitudinal member and clamping devices of the dynamic stabilization device of FIG. 45.
Figure 46A:
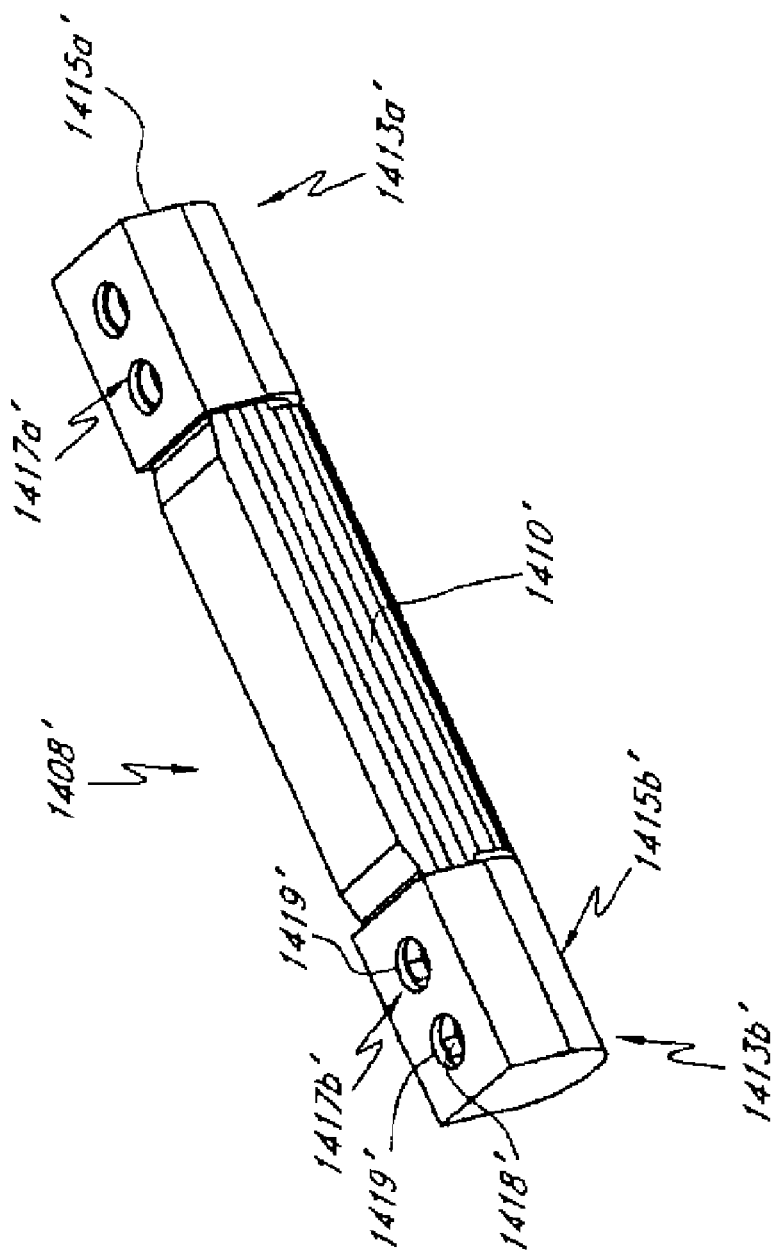
FIG. 46A is perspective view of another embodiment of a longitudinal member.
Figure 47:
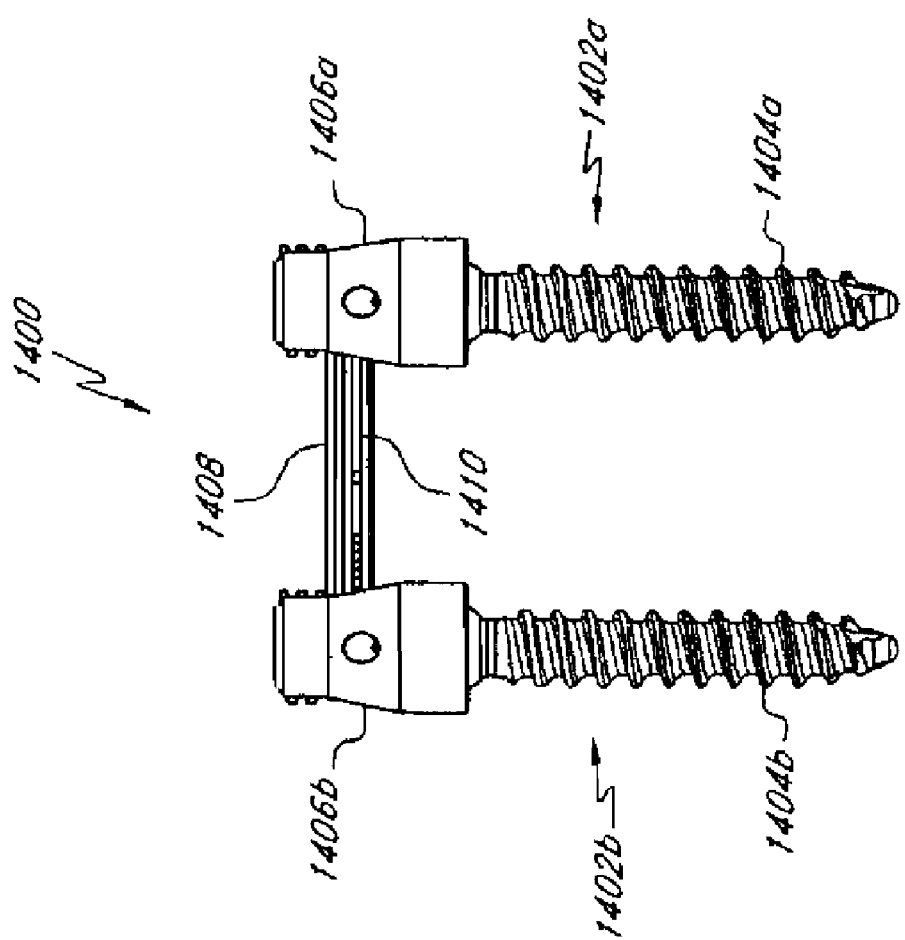
FIG. 47 is a plan view of the dynamic stabilization device of FIG. 45.

The stabilization apparatus 1400 comprises a stabilization device that permits a range of motion of the spine under normal body loads. As shown in FIG. 45, the stabilization device may comprise a longitudinal member 1408 that extends between the first housing 1406a and the second housing 1406b. In one embodiment, the longitudinal member 1408 extends from the first housing 1406a to the second housing 1406b. As discussed below, the longitudinal member 1408 has a first end 1413a (shown in FIG. 46) that is engaged in the first passage 1407a of the first housing 1406a and a second end 1413b that is engaged in the first passage 1407b of the second housing 1406b. The length of the longitudinal member 1408 between the first and second ends 1413a, 1413b is sufficient to span the distance between the vertebrae $V_1$ and $V_2$, which can be adjacent vertebrae or spaced apart, as discussed above. The longitudinal member 1408 comprises an array of elongated, load-bearing elements. As used herein, an array of elements refers to an arrangement of one, two, three, four, or more elements. An array of elements may be arranged as a substantially linear array (e.g., generally as shown in FIGS. 45-46A), a substantially cylindrical array (e.g., generally as shown in FIGS. 46E-46J), or as an array having any other suitable shape or configuration (e.g., as a rectangular array, an oval array, etc.). Elongated, load-bearing elements include, for example, sheets, plates, rods, or other suitable elongated members. The elongated load-bearing elements can have any suitable cross-sectional shapes, and different load-bearing elements can have different cross-sectional shapes. For example, rods may have a cross-sectional shape that includes circular shapes, oval shapes, or rectangular shapes. The cross-sectional shape of a load-bearing element can vary along its length (e.g., a rod may be rectangular near one or both ends and circular near the center).

The longitudinal member 1408 shown in FIG. 45 comprises a substantially linear array that comprises a plurality of thin sheets 1410. For example, in one embodiment, the longitudinal member 1408 includes two thin sheets 1410. In another embodiment, the longitudinal member 1408 includes more than two sheets, e.g., 10 or more, or as many as 12 or more thin sheets 1410. The thin sheets 1410 may be configured as a generally linear array of stacked sheets or layers (see, also, FIGS. 46 and 46A). The number, configuration, and materials selected for the sheets 1410 can be selected to provide desirable performance, e.g., rigidity and/or spring constant.

The stabilization apparatus 1400 comprises a first clamping device 1412a and a second clamping device 1412b. The first clamping device 1412a is coupled with the first housing 1406a and is configured to secure a portion of the first end 1413a of the longitudinal member 1408 to the first housing 1406a. The second clamping device 1412b is coupled with the second housing 1406b and configured to secure a portion of the second end 1413b of the longitudinal member 1408 to the second housing 1406b while allowing the thin sheets 1410 to slide relative to each other and relative to the second housing 1406b.

In the embodiment shown in FIG. 45, the first clamping device 1412a is configured to clamp the first end 1413a of the longitudinal member 1408. As used in this context, the phrase "to clamp" includes rigidly connecting a portion of the first end 1413a of the longitudinal member 1408 to the housing 1406a whereby the thin sheets 1410 thereof have a substantially limited or no range of motion relative to each other. As discussed further below, in this embodiment the thin sheets 1410 may be mechanically coupled together at a portion of the end 1413a to limit their relative motion, for example, by the use of one or more rivets.

In other embodiments, the first clamping device 1412a is configured to secure a portion of the first end 1413a of the longitudinal member 1408 without clamping the first end 1413a to the first housing 1406a. As used in this context, the phrase "to secure" includes connecting a portion of the first end 1413a of the longitudinal member 1408 to the housing 1406a, but allowing at least some of the thin sheets 1410 to slide relative to each other and relative to the second housing 1406a. In some embodiments, both ends 1413a, 1413b of the longitudinal member 1408 are secured to the housings 1406a, 1406b without being clamped. In another embodiment, both ends of a longitudinal member similar to the longitudinal member 1408 are clamped. In some variations where both ends of a longitudinal member are to be clamped, the longitudinal member is made more flexible than the member 1408 because clamping both ends of the member significantly increases the stiffness compared to the stiffness of the dynamic stabilization apparatus 1400.

When the first and second ends 1413a, 1413b of the longitudinal member 1408 are fastened as described, the longitudinal member 1408 acts as a spring. In some embodiments, the longitudinal member 1408 acts as a leaf spring. In a dynamic spinal stabilization procedure, the distal ends of the fasteners 1402a and 1402b are coupled to two vertebrae $V_1$ and $V_2$. Movement of the vertebrae causes a change in the distance between the distal ends of the fasteners 1402a and 1402b and the longitudinal member 1408 flexes, permitting motion between the vertebrae but resisting the change in distance between the ends of the fasteners 1402a and 1402b. The flexing of the longitudinal member 1408 is analogous to a spring, urging the fasteners 1402a, 1402b and the vertebrae $V_1$ and $V_2$ back to a selected orientation, e.g., consistent with minimal spinal curvature. Accordingly, the dynamic stabilization apparatus 1400 provides stability and restores natural stiffness to a diseased or damaged portion of the spine.

The components of the dynamic stabilization apparatus 1400 can comprise any suitable material, such as a biocompatible metal, e.g., titanium or a titanium alloy. The components may also be fabricated from other metals, or other suitable materials.

Although FIG. 45 illustrates a one-level treatment involving a stabilization apparatus, another variation enables multilevel stabilization. A multilevel stabilization can be performed with a longitudinal member that is similar to the longitudinal member 1408, e.g., one that operates as a spring (e.g., a leaf spring) at least along a portion of the member. The multilevel longitudinal member is longer such that it can extend between three or more successive vertebrae. The multilevel stabilization apparatus or the longitudinal member therefore can be arranged to preserve at least some of the natural movement of the vertebrae with which it is coupled in a manner similar to the apparatus 1400 and the member 1408.

In one variation, a multilevel stabilization apparatus is configured to applied in different ways to different patients. For example, the apparatus can be configured such that an end of the multilevel stabilization member can be clamped or secured, as defined above, depending on the needs of the patient. The multilevel stabilization member can be further configured such that when two or more adjacent clamping devices clamp the member to two adjacent fasteners, the adjacent fasteners and the span of the member extending therebetween are very rigid and provide a rigid fixation of the vertebrae with which they are connected. The stabilization member can be further configured such that if one of two adjacent clamping devices is clamped while the other of the two adjacent clamping devices is secured, the span of the member therebetween acts as a spring and in certain embodiments as a leaf spring. The multilevel stabilization apparatus is flexible in its application in that it can be applied to rigidly fix two of three adjacent vertebrae together (e.g., the caudal-most and a central vertebrae) while permitting movement between one of the two fixed vertebrae and the third vertebrae (e.g., the cephalad-most and a central vertebrae). In another technique, a multilevel procedure can involve clamping a central portion of a multilevel longitudinal member and securing peripheral portions, e.g., portions coupled with cephalad-most and caudal-most screws of a multilevel stabilization apparatus. The multilevel stabilization apparatuses can employ end caps, as discussed below in connection with FIG. 46A, to enable the multilevel longitudinal member to be used in connection with standard fasteners and with fasteners with yokes, as discussed above.

FIG. 46 further illustrates features of an embodiment of the clamping devices 1412a and 1412b and the longitudinal member 1408. The first clamping device 1412a clamps the first end 1413a of the longitudinal member 1408 in the second passage 1409a, and the second clamping device 1412b secures the second end 1413b of the member 1408 in the second passage 1409b. The first clamping device 1412a comprises a threaded portion 1416 configured to engage the housing 1406a (shown in FIG. 45) and a yoke 1420 that is rotatably coupled with the threaded portion 1416. Accordingly, the threaded portion 1416 can spin relative to the yoke 1420. The yoke 1420 is configured to engage the sides of the longitudinal member 1408 as the threaded portion 1416 engages threads formed in the housing 1406*a*. A portion of the first end 1413*a* of the longitudinal member 1408 is clamped into the first housing 1406*a* by screwing the threaded portion 1416 into the housing 1406*a* while the yoke 1420 engages the sides of the longitudinal member 1408. The threaded portion 1416 may be rotated relative to the yoke 1420 by using a device such as the endoscopic screwdriver 660 (shown in FIG. 28). A recess 1432 is provided in the threaded portion 1416 to allow the endoscopic screwdriver 660 or other similar device to engage and rotate the threaded portion 1416. Other structures can be provided to spinning or rotating the threaded portion 1416.

The second clamping device 1412*b* illustrated in FIG. 46 is similar to the first clamping device 1412*a* in one embodiment. The second clamping device 1412*b* secures the second end of the longitudinal member 1408 to the second housing 1406*b* in a manner similar to that described for the first clamping device 1412*a*. As discussed further below, a set of retaining members 1424 and 1428 may be provided such that the thin sheets 1410 may slide relative to each other and relative to the second housing 1406*b*.

In some embodiments, a position-limiting device 1429 is provided to limit the range of positions at which the clamping device 1412*b* can secure the longitudinal member 1408. In one arrangement, the position-limiting device 1429 is a ramp-like structure that has a length that is more than the length of the individual retaining members 1428. Because the length of the ramp exceeds that of the retaining members 1428, the members 1424 on the clamping device 1412*b* cannot couple with the position-limiting device. Thus, the position limiting device 1429 prevents the clamping devices 1412*b* from being positioned too close to the clamping device 1412*a*.

In one arrangement, the longitudinal member 1408 is thinner (e.g., 0.005 inches thinner) at the end without the rivets 1432. This arrangement permits the clamping devices 1412*a*, 1412*b* to be interchangeable.

As discussed above, in some applications, it is desirable to contain any debris that might be generated by the dynamic stabilization apparatus 1400. One technique for limiting the spread of debris generated, e.g., by wear of the apparatus 1400, is to provide a coating that reduces friction or otherwise limits generation of particles or fragments from the apparatus 1400. The coating may be a conformal coating, e.g., comprising a dielectric material selected to protect one or more components of the apparatus 1400 from moisture, corrosion, abrasion, and other environmental stresses. Some conformal coatings that could be used include silicone, acrylic, urethane, epoxy, and Parylene The longitudinal member 1408 comprises a plurality of thin sheets 1410. In one embodiment, the thin sheets 1410 are fixed together at the first end 1413*a* of the longitudinal member 1408. The sheets 1410 may be fixed together by one or more rivets 1432 extending through some or all of the sheets. Two rivets 1432 are depicted in the embodiment shown in FIG. 46, although other numbers of rivets, including one, more than two, or none can be used. One of ordinary skill in the art will recognize that the thin sheets 1410 can be mechanically coupled together in other ways, such as by welding or with an adhesive. In some embodiments, the thin sheets 1410 are mechanically coupled together by the pressure exerted on the end portion 1413*a* by the first clamping device 1412*a* while it is firmly secured to the housing 1406*a*.

The second clamping device 1412*b* may comprise a first retaining member 1424, and the longitudinal member 1408 may comprise a second retaining member 1428. The first and second retaining members 1424, 1428 are configured to limit the longitudinal motion of the longitudinal member 1408 while allowing at least some of the thin sheets 1410 to slide relative to each other. In the embodiment shown in FIG. 46, the retaining members 1424, 1428 comprise a plurality of notches configured to mate with each other and to allow the second end of the longitudinal member 1408 to be secured by the second clamping device 1412*b* without clamping the thin sheets 1410 together. In some embodiments, fewer notches than shown can be provided. For example, a single notch may be used in the retaining members 1424, 1428. In other embodiments 8 to 10 or more notches may be provided to limit the motion of the longitudinal member 1408. The notches in the retaining member 1428 may be provided on one or more of the thin sheets 1410 of the longitudinal member 1408. It will be apparent to one of ordinary skill in the art that the retaining members 1424, 1428 may take alternative forms. For example, a pin on the bottom of the threaded portion 1416 may be configured to engage a groove or dimple on the upper surface of the proximal-most sheet 1410 of the longitudinal member 1408 in order to limit its motion. Alternatively, the first passage 1407*b* of the second housing 1406*b* may be configured to prevent one or more of the thin sheets 1410 from extending through the second housing 1406*b* while allowing other thin sheets 1410 to extend therethrough.

The first clamping device 1412*a* shown in FIG. 46 is similar to the second clamping device 1412*b* in one embodiment. In embodiments in which the first end 1413*a* of the longitudinal member 1408 is clamped rather than secured to the first housing 1406*a*, the first clamping member 1412*a* may be configured without the retaining member 1424.

By fastening the first and second ends 1413*a*, 1413*b* of the longitudinal member 1408 as described, the motion of the longitudinal member 1408 in a direction parallel to its longitudinal axis of the member 1408 is limited while the sliding of the thin sheets 1410 allows the member 1408 to flex, for example, at least partially in the transverse direction. Accordingly, this embodiment of the longitudinal member 1408 acts as a leaf spring. The characteristics of the spring, such as its spring rate, can be selected by appropriately selecting the number, the length and thickness, and the material properties of the thin sheets 1410. Accordingly, different embodiments of the longitudinal member 1408 may comprise a linear spring rate or a nonlinear spring rate.

Each of the thin sheets 1410 of the longitudinal member 1408 may be fabricated from a different material. To limit the extensibility of the longitudinal member 1408, some of the thin sheets 1410 may be fabricated from a material substantially incompressible or substantially inextensible along the longitudinal axis of the member 1408 under loads provided in normal spinal motion. Suitable materials include a biocompatible metal, e.g., titanium or a titanium alloy. The thin sheets 1410 may also be fabricated from other metals, or other suitable materials.

The operation of the longitudinal member 1408 may be facilitated by configuring the member 1408 to minimize wear, for example, to configure the thin sheets 1410 to promote sliding thereof. Wear may be minimized by, for example, coating the sheets 1410 with low-friction material. One embodiment of the longitudinal member 1408 comprises thin sheets 1410 made from at least two materials. One material may be substantially incompressible or inextensible along its longitudinal axis, such as, for example, a biocompatible material like titanium or titanium alloy. The other material may be a low-friction material to minimize wear and to promote sliding of the thin sheets 1410. Suitable low-friction materials include, for example, ultra high molecular weight polyethylene (UHMWPE) or nylon. In the embodiment shown in FIG. 46, sheets of an incompressible material are alternated with sheets of a low-friction material to minimize wear and promote sliding. Some of the arrangements that reduce friction and promote sliding also substantially prevent generation of loose debris that might otherwise result from relative motion of the sheets 1410.

FIG. 46A illustrates one variation of a longitudinal member 1408' that permits the use of a conventional fastener, such as a conventional pedicle screw with a housing and cap screw arrangement, similar to those disclosed in, for example, U.S. patent application Ser. No. 11/490,511, filed Jul. 20, 2006, entitled "APPARATUS FOR CONNECTING A LONGITUDINAL MEMBER TO A BONE PORTION," and U.S. patent application Ser. No. 10/483,605, filed Jan. 13, 2004, entitled "APPARATUS FOR CONNECTING A LONGITUDINAL MEMBER TO A BONE PORTION," each of which is hereby incorporated by reference herein in its entirety.

The longitudinal member 1408' is similar to the longitudinal member 1408 except as set forth below. The longitudinal member 1408' has first and second ends 1413a', 1413b' and a plurality of laminations or thin sheets 1410' extending therebetween. The thin sheets 1410' are configured in a generally linear array of laminations. The thin sheets 1410' and the longitudinal member 1408' act as a leaf spring in use, as discussed further below. The longitudinal member also includes a first end cap 1415a' and a second end cap 1415b'. The first end cap 1415a' is located adjacent to the first end 1413a' of the longitudinal member 1408' and houses one end of the thin sheets 1410'. The second end cap 1415b' is located adjacent to the second end 1413b' of the longitudinal member 1408' and houses the other end of the thin sheets 1410' in one embodiment.

Preferably at least one of the two end caps is coupled with a corresponding end portion of the thin sheets 1410' in a manner that permits the sheets to move relative to each other, similar to the movement of the thin sheets 1410. For example, a first riveted connection 1417a' can be provided between the first end cap 1415a' and the thin sheets 1410' adjacent to the first end 1413a'. The first riveted connection 1417a' can include two rivets. The first riveted connection 1417a' is a rigid connection in one arrangement that substantially prevents sliding of the thin sheets 1410' relative to each other adjacent to the first end 1413a'. A second riveted 1417b' connection can be provided between the second end cap 1415b' and the thin sheets 1410' adjacent to the second end 1413b'. The second riveted connection 1417b' can include one or more slots 1418' formed in the thin sheets 1410' and corresponding rivet holes 1419' formed in the second end cap 1415b'. One or a plurality, e.g., two, rivets can be extended through the rivet holes 1419' and into the slots 1418'. When installed in the rivet holes 1419' and the slots 1418' the rivet(s) permit movement of the thin sheets 1410' in a manner similar to a leaf spring as discussed above.

The longitudinal member 1408' is advantageous in that the end caps 1415a', 1415b' absorb the force of conventional cap screws or other similar clamping devices while permitting the leaf-spring-like movement of the thin sheets 1410'. This enables the longitudinal member 1408' to be used with a wide array of standard, as well as propriety, fasteners, including screws configured for insertion into pedicles or other bony segments.

FIG. 46B is a perspective view schematically illustrating another embodiment of a dynamic stabilization apparatus 1400a that comprises a first fastener 1402a, a second fastener 1402b, and a longitudinal member 1408a. The first fastener 1402a has a threaded shank 1404a for engaging a portion of a vertebra $V_1$. The second fastener 1402b has a threaded shank 1404b for engaging a portion of a vertebra $V_2$. The vertebrae $V_1$ and $V_2$ may be adjacent or may be separated by one or more vertebrae. The fasteners 1402a and 1402b comprise housings 1406a and 1406b, respectively. Cap screws 1438a and 1438b may be used to secure ends of the longitudinal member 1408a to the fasteners 1402a and 1402b, respectively. The fasteners 1402a and 1402b may be standard pedicle screws or bone anchors such as the fastener 600 illustrated in FIGS. 26 and 27. In some embodiments, at least one of the fasteners 1402a and 1402b is positionable in any one of a plurality of angular positions relative to the housing 1406a or 1406b, respectively, as further described below. FIGS. 46C and 46D, respectively, are side and top plan views of the dynamic stabilization apparatus 1400a.

FIG. 46E is a side cross-section view of the dynamic stabilization apparatus 1400a taken along section plane 46E-46E of FIG. 46D. The longitudinal member 1408a comprises retention members 1442a and 1442b, an elongated central core 1440, and a plurality of narrow rods 1450 arranged in a generally cylindrical array surrounding the central core 1440 (best seen in FIGS. 46F and 46G). Each retention member 1442a, 1442b has a longitudinal passageway 1462a, 1462b (see FIG. 46F) having a cross-sectional area sufficiently large for ends 1454a, 1454b of the central core 1440 to pass therethrough. Opposing ends of the narrow rods 1450 engage the retention members 1442a, 1442b, respectively, and in one embodiment are configured in a substantially cylindrical, cage-like array. As depicted, the rods 1450 have generally circular cross-sectional shapes, but in other embodiments the rods 1450 may have different cross-sectional shapes (e.g., oval, rectangular, flattened, etc.).

End caps 1448a, 1448b secure the retention members 1442a, 1442b to the ends 1454a, 1454b of the central core 1440, respectively. The core 1440 and the rods 1450 may be configured so that the longitudinal member 1408a resists axial compression but permits a degree of transverse flexibility when subjected to spinal loads. For example, the number of the rods 1450, their flexibility, as well as the flexibility of the core 1440, can be selected to provide a desired range of motion for the spine of a patient. Embodiments of the longitudinal member 1408a advantageously can flex in multiple directions, for example, in substantially all directions that are substantially transverse to the elongated core member 1440. Accordingly, the longitudinal member 1408a beneficially provides dynamic spinal stabilization not only for forces corresponding to spinal flexion and compression but also for forces corresponding to lateral or transverse displacements of the spinal. Further details of embodiments of the longitudinal member 1408a are provided below.

The longitudinal member 1408a may be attached to the fasteners 1402a, 1402b by inserting ends of the member 1408a into the housings 1406a, 1406b and securing the cap screws 1438a, 1438b, respectively. The length of the longitudinal member 1408a between the first and second ends 1454a and 1454b is sufficient to span the distance between the vertebrae $V_1$ and $V_2$, which can be adjacent vertebrae or spaced apart. The longitudinal member 1408a may be sufficiently flexible to provide dynamic stability to portions of the spine near the vertebrae $V_1$ and $V_2$.

FIG. 46F is an exploded perspective view of one embodiment of the longitudinal member 1408a. The core 1440 is an elongated element extending between the ends 1454a and 1454b. The core 1440 has two flanges 1444a and 1444b defining a central portion 1441 therebetween. The core 1440 may be fabricated as an integral unit or as separate pieces that are thereafter joined. The core 1440 may be made from a material that flexes under normal spinal loads. In some embodiments, the central portion 1441 comprises a different cross-sectional area, cross-sectional shape, and/or material than portions near the ends 1454a, 1454b. For example, the ends 1454a, 1454b may be made from a substantially rigid material (e.g., titanium), while the central portion 1441 is made from an elastomeric material (e.g., a polymer). In the embodiment shown in FIG. 46F, the central portion 1441 is a flexible rod. In other embodiments, the central portion 1441 may be configured in part as a flexible tether, braided fabric, spring, and/or ball-and-socket linkage. Compressible O-rings 1446a and 1446b are disposed adjacent the flanges 1444a and 1444b, respectively, and permit a degree of longitudinal compression of the member 1408a as further described below. The O-rings 1446a, 1446b may be made from any suitable elastomeric material.

The retention members 1442a, 1442b have substantially central, longitudinal passageways 1462a, 1462b, respectively, having a cross-section sufficient to permit the ends 1454a, 1454b of the core 1440, respectively, to pass therethrough. In the embodiment shown in FIG. 46F, each retention member 1442a, 1442b comprises a lateral portion 1443a, 1443b and a medial portion 1445a, 1445b, respectively, which are substantially cylindrical in shape. The medial potions 1445a, 1445b have larger cross sectional areas than the lateral portions 1443a, 1443b, although this is not a requirement. Likewise, the cross-sectional area of the passageways 1462a, 1462b may be larger within the medial portions 1445a, 1445b than within the lateral portions 1443a, 1443b. The retention members 1442a, 1442b may be made from a substantially rigid biocompatible material such as titanium or a titanium alloy.

In the embodiment shown in FIG. 46F, each of the medial portions 1445a, 1445b comprises openings 1452a, 1452b configured to receive opposite ends of the rods 1450. The openings 1452a, 1452b extend substantially parallel to the longitudinal passageways 1462a, 1462b, so that the rods 1450 are maintained substantially parallel to the elongated core 1440, In certain embodiments, the openings 1452a, 1452b in the medial portions 1445a, 1445b are spaced in a substantially uniform azimuthal manner around the respective longitudinal passageways 1462a, 1462b. Accordingly, when opposing ends of the rods 1450 are disposed in the openings 1452a, 1452b, respectively, the rods 1450 will form a substantially cylindrical, cage-like array, which surrounds the elongated core 1440 (see FIGS. 46F and 46G). In other embodiments, the array of rods 1450 (as viewed perpendicularly to the longitudinal axis of the member 1408a) may be configured in a linear array, an oval array, a rectangular array, or any other suitably shaped array. Many variations are contemplated.

The number of openings 1452a, 1452 may be equal to the number of rods 1450 used in the longitudinal member 1408a. In some embodiments, the medial portions 1445a, 1445b may be fabricated with a relatively large number of openings 1452a, 1452b (e.g., generally as shown in FIG. 46F). Rods 1450 may be placed in all, or fewer than all, of the openings 1452a, 1452b. Additionally, in embodiments using fewer rods 1450 than openings 1452a, 1452b, individual rods 1450 can be disposed at selected azimuthal positions surrounding the core 1440 to provide an appropriate range of spinal flexibility for the patient.

Generally, each of the rods 1450 used in the longitudinal member 1450 is made from the same material, but this is not a requirement. Each rod 1450 may be made from a material that resists axial compression but which permits a degree of transverse flexibility. The transverse cross-sectional shape, area, length, or diameter of the rods 1450 may also be selected to provide suitable axial inflexibility and transverse flexibility. In some embodiments, the rods 1450 are made from a biocompatible material such as titanium, a titanium alloy, or stainless steel.

FIG. 46G shows an embodiment of the longitudinal member 1408a in an assembled state. Opposing ends of the rods 1450 are disposed in the openings 1452a, 1452b of the retention members 1442a, 1442b, respectively. The retention members 1442a, 1442b engage the core 1440 so that the O-rings 1446a, 1446b abut inner surfaces of the medial portions 1445a, 1445b, respectively. In some embodiments, the ends 1454a, 1454b extend entirely through the passageways 1452a, 1452b, which permits the retention members 1442a, 1442b to be secured to the core member 1400 by the end caps 1448a, 1448b. In various embodiments, the end caps 1448a, 1448b are threaded and/or welded to the core 1440. In other embodiments, adhesives are used. As shown in FIG. 46F, notches or grooves 1465a, 1465b may be formed in the ends 1454a, 1454b, respectively, to permit the end caps 1448a, 1448b to be snap-fit onto the core 1440. In some embodiments, a combination of these techniques may be used.

The longitudinal member 1408a can be configured so that there is an end space 1462 (best seen in FIG. 46E) in the openings 1452a and/or 1452b in the retention members 1442a and/or 1442b. The end space 1462 may permit relatively small ranges of extension and/or retraction of the rods 1450 in the openings 1452a and/or 1452b or relative movement between the rods 1450 and the retention members 1442a, 1442b when the longitudinal member 1408a is flexed, compressed, and/or extended. In some embodiments, the range of longitudinal retraction of the member 1408a is limited in part by the length of the end space 1462, because at a limiting value of the retraction, ends of the rods 1450 in the end space 1462 will contact the bottom of the openings, thereby preventing further retraction. The length of the end space 1462 is determined by, for example, the depth of the openings 1452a, 1452b, the length of the rods 1450, and the spacing between of the retention members 1442a, 1442b. Additionally, the length of the end space 1462 can be configured to permit the longitudinal member 1408a to be slightly compressible in an axial direction generally parallel to the elongated care 1440. For example, if a compressive load is applied to opposing ends of the longitudinal member 1408a, the O-rings 1446a, 1446b will compress, and ends of the rods 1450 will slide into the end space 1462, thereby permitting the retention members 1442a and 1442b to move toward each other. Accordingly, in certain embodiments, the longitudinal member 1408a is relatively inflexible along its longitudinal axis but may be configured to retain a limited range of longitudinal motion under spinal forces of compression or tension.

In some embodiments, an optional outer sheath 1460 is used to cover a central portion 1462 of the longitudinal member 1408a. The outer sheath 1460 may comprise a cylindrical piece of heat-shrink tubing or other suitable protective covering. The outer sheath 1460 can be left on the longitudinal member 1408a after delivery to the surgical site to prevent tissue growth into the array of rods 1450. In some surgical applications, the outer sheath 1460 is removed after the longitudinal member 1408a is inserted into the patient. The outer sheath 1460 is illustrated in FIGS. 46E and 46F but is removed for clarity in FIG. 46G.

FIGS. 46H and 46I are perspective views schematically illustrating additional embodiments of the longitudinal member 1408a. In these embodiments, a substantially cylindrical, cage-like array of rods 1450 is secured between two substantially cylindrical retention members 1442a and 1442b. In these embodiments, an elongated core 1440 may be disposed substantially symmetrically within the array of rods 1450 and may also extend between the retention members 1442a, 1442b. The core 1440 may be secured to the retention members 1442a, 1442b by, e.g., welding and/or adhesives. As described above, the rods 1450 and the optional core 1440 may be fabricated from a material that permits embodiments of the longitudinal member 1408a to be relatively inflexible in directions along the longitudinal axis of the member 1408a and to be relatively flexible in directions generally transverse to the longitudinal axis of the member 1408a.

As can be seen in FIGS. 46H and 46I, ends of the rods 1450 and the core 1440 may extend through openings in the retention members 1442a, 1442b, which may permit their easier arrangement in and attachment to the longitudinal member 1408a. The rods 1450 and the optional core 1440 may be attached to the retention members 1442a, 1442b by, for example, welding and/or adhesives. End caps generally similar to those described above are used in some embodiments. In certain embodiments, the core 1440 is secured (e.g., clamped) to both of the retention members 1442a, 1442b, while some or all of the rods 1450 are secured to a retention member at one end of the longitudinal member 1408a but are allowed to slide through the openings in the retention member at the opposing end of the longitudinal member 1408a. Such embodiments advantageously permit the undamped ends of the rods to slide relative to the retention member as the longitudinal member 1408a flexes.

Some embodiments of the longitudinal member 1408a comprise an optional sheath 1460 covering the rods 1450; for example, as shown in FIG. 46I. The outer sheath 1460 can be left on the longitudinal member 1408a after delivery to the surgical site to prevent tissue growth into the array of rods 1450. In some surgical applications, the outer sheath 1460 is removed after the longitudinal member 1408a is inserted into the patient.

FIG. 46J is a perspective view of another embodiment of a longitudinal member 1408a' comprising an array of rods 1450' extending between two retention members 1442a' and 1442b'. The array of rods 1450' may be configured in a substantially cylindrical, cage-like configuration (e.g., substantially as shown in FIG. 46J), and in some embodiments, the array includes a rod disposed along a substantially central, longitudinal axis of the member 1408a'. The rods 1450' may be formed from a material that resists axial compression (e.g., is relatively inflexible axially), but that permits a range of transverse deflection (e.g., is relatively flexible transversely). In some embodiments, the rods 1450' are made from a biocompatible metal such as titanium. The retention members 1442a' and 1442b' may be generally spherically shaped and may include substantially planar portions 1470a' and 1470b', respectively. The planar portions 1470a' and 1470b' may permit the cap screws 1438a and 1438b to more securely couple the retention members 1442a' and 1442b' to the fasteners 1402a and 1402b. As described above with reference to FIG. 46H, in some embodiments, ends of some of the rods 1450' are clamped by one retention member (e.g., the retention member 1442a') while opposing ends of these rods 1450' are configured to slide relative to the other retention member (e.g., the retention member 1442b'). In such embodiments, the array of rods 1450' may include a central rod that is secured to the retention members 1442a' and 1442b'. Such embodiments advantageously permit some of the rods 1450' to slide relative to the undamped retention member (e.g., the member 1442b') when the longitudinal member 1408a' flexes. Some embodiments of the longitudinal member 1408a' may include an outer sheath surrounding the array of rods 1450' (not shown in FIG. 46J). In some embodiments, an outer sheath (not shown in FIG. 46J) is used to cover the array of rods 1450'. The outer sheath can be is left on the longitudinal member 1408a' after delivery to the surgical site to prevent tissue growth into the array of rods 1450'. In some surgical applications, the outer sheath is removed after the longitudinal member 1408a' is inserted into the patient.

The longitudinal member 1408a, 1408a' man be configured to act like a spring (e.g., similar to a leaf spring) as further described below. The longitudinal member 1408a, 1408a' may be configured to have a spring rate (e.g., stiffness) that provides a desired degree of dynamic stabilization and range of motion. Embodiments of the longitudinal member 1408a, 1408a' can be configured with a linear spring rate or a nonlinear spring rate. In certain embodiments, the longitudinal member 1408a, 1408a' is also configured to act as a spring along the longitudinal axis of the member 1408a, 1408a'. In certain such embodiments, the spring rate along the longitudinal direction is larger than the spring rate along a transverse direction (e.g., the member 1408a, 1408a' is suffer longitudinally than transversely).

FIGS. 47-54 illustrate the operation of one embodiment of the dynamic stabilization apparatus 1400. Each of the fasteners 1402a and 1402b has a threaded shank 1404a and 1404b and an enlarged head 1436a and 1436b, respectively. Each of the housings 1406a, 1406b has a first passage 1407a, 1407b and a second passage 1409a, 1409b that has a longitudinal axis extending transverse to the first passage 1407a, 1407b. The fasteners 1402a and 1402b extend through an opening in the second passage 1409a, 1409b of the corresponding housings 1406a and 1406b. In one embodiment of the dynamic stabilization apparatus 1400, at least one of the fasteners 1402a and 1402b is positionable in any one of a plurality of angular positions relative to the longitudinal axis of the second passage 1409a, 1409b of the corresponding housing 1406a or 1406b. Arrangements that facilitate such positioning and that can be used in connection with any of the members 1408, 1408', or 1408a are described in, for example, U.S. patent application Ser. No. 11/490,511, filed Jul. 20, 2006, entitled "APPARATUS FOR CONNECTING A LONGITUDINAL MEMBER TO A BONE PORTION," and U.S. patent application Ser. No. 10/483,605, filed Jan. 13, 2004, entitled "APPARATUS FOR CONNECTING A LONGITUDINAL MEMBER TO A BONE PORTION," each of which is hereby incorporated by reference herein in its entirety.

Figure 50:
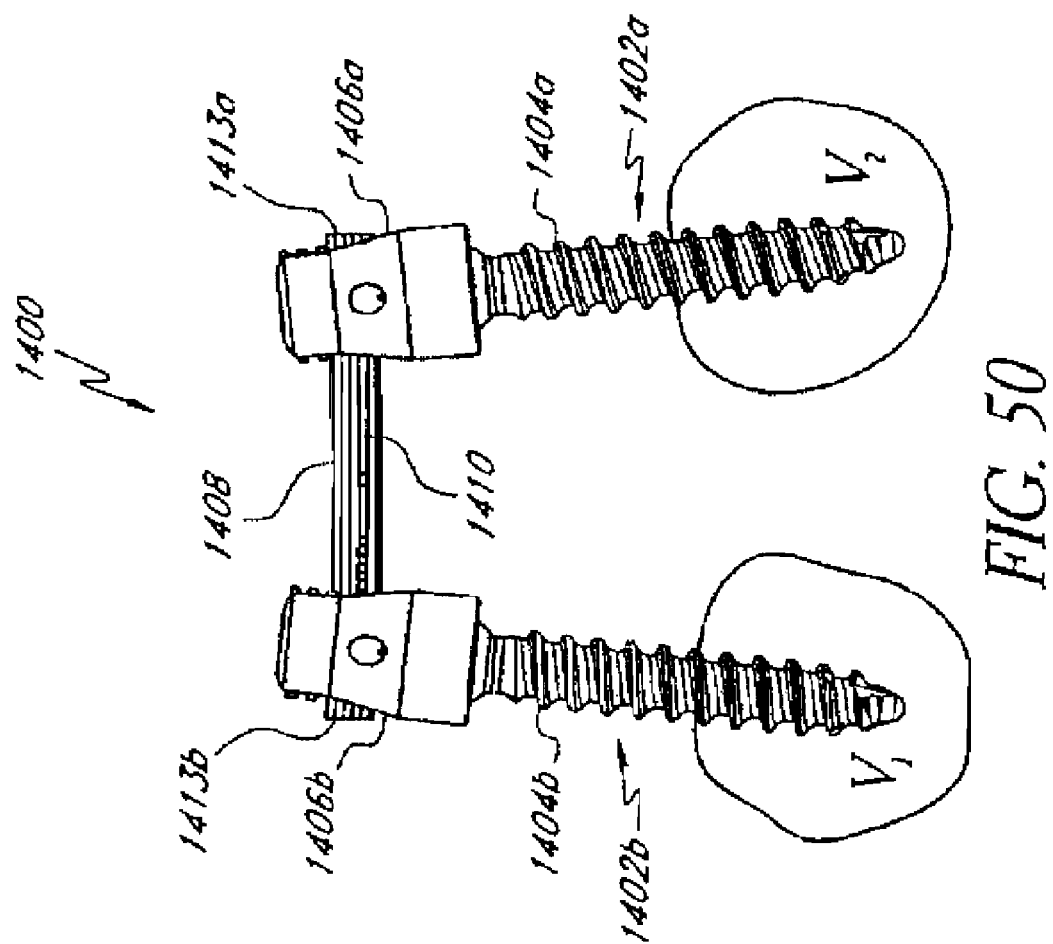
FIG. 50 is a plan view of the dynamic stabilization device of FIG. 47 in a configuration corresponding to extension of the spine.
Figure 51:
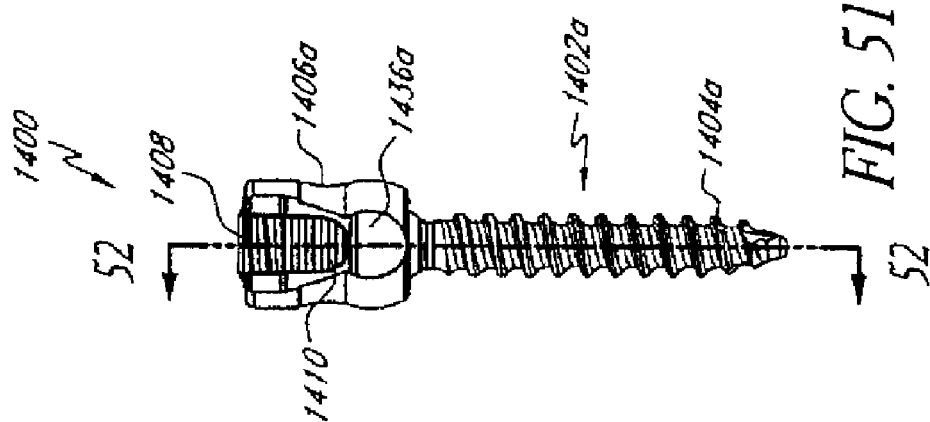
FIG. 51 is an end view of the dynamic stabilization device of FIG. 47 in the configuration of FIG. 50.

FIGS. 50-52 illustrate a configuration of the dynamic stabilization apparatus 1400 of FIG. 45 when the vertebrae $V_1$ and $V_2$ are in extension. The vertebrae $V_1$ and $V_2$ exert extension forces $F_E$ on the distal ends of the fasteners 1402a and 1402b, which causes the distal ends to separate from each other. As shown in FIG. 52, the thin sheets 1410 of the longitudinal member 1408 flex transversely to the longitudinal axis of the member 1408. When undergoing spinal extension, the shape of the longitudinal member 1408 becomes concave in the direction away from the spine (upward in FIG. 52), because the first end of the longitudinal member 1400 is clamped by the first housing 1406a while the second end of the longitudinal member 1408 permits the thin sheets 1410 to slide relative to each other and relative to the second housing 1406b. Accordingly, the longitudinal member 1408 acts like a leaf spring and exerts a restoring force that tends to resist the extension of the vertebrae $V_1$ and $V_2$.

Figure 54:
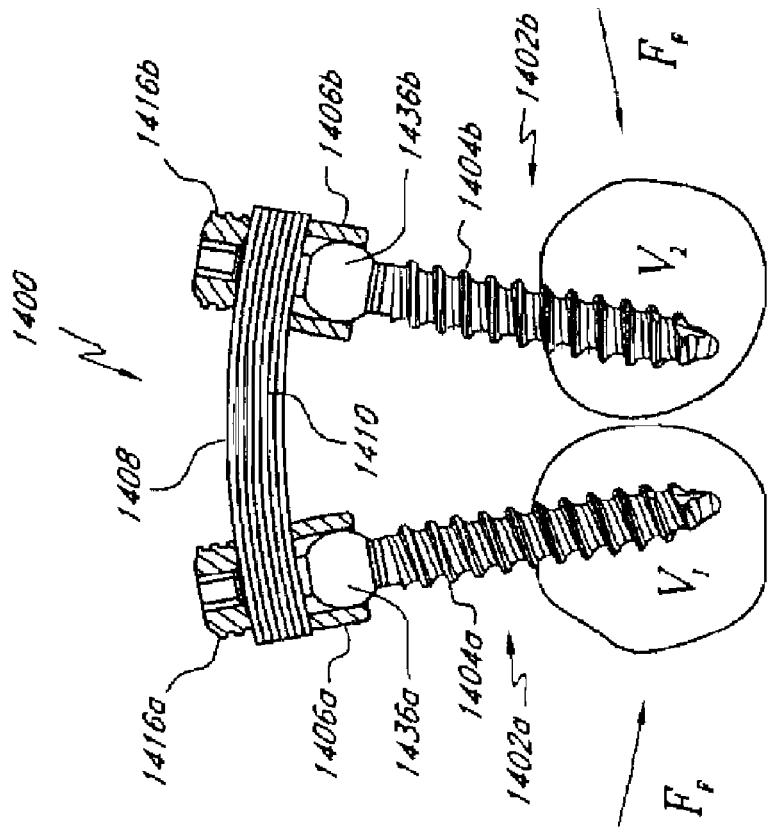
FIG. 54 is a partial cross-section view of the dynamic stabilization device of FIG. 53 taken along section plane 54-54.
Figure 53:
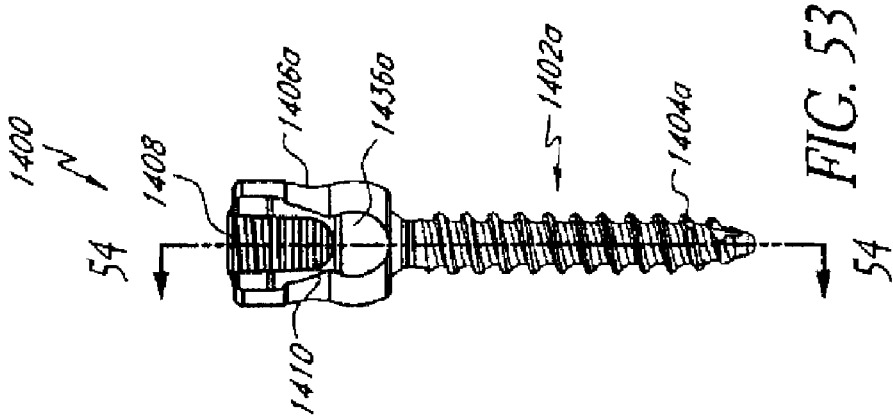
FIG. 53 is an end view of the dynamic stabilization device of FIG. 47 in a configuration corresponding to flexion of the spine.

FIGS. 53-54 illustrate a configuration of the dynamic stabilization apparatus 1400 when the vertebrae $V_1$ and $V_2$ are in flexion. The vertebrae $V_1$ and $V_2$ exert flexion forces $F_F$ on the distal ends of the fasteners 1402a and 1402b, which causes the distal ends to approach each other. As shown in FIG. 54, the thin sheets 1410 of the longitudinal member 1408 flex transversely to the longitudinal axis of the member 1408. When undergoing spinal flexion, the shape of the longitudinal member 1408 becomes concave in the direction toward the spine (downward in FIG. 54), because the first end of the longitudinal member 1400 is clamped by the first housing 1406a while the second end of the longitudinal member 1408 permits the thin sheets 1410 to slide relative to each other and relative to the second housing 1406b. Accordingly, the longitudinal member 1408 acts like a leaf spring and exerts a restoring force that tends to resist the flexion of the vertebrae $V_1$ and $V_2$.

In other embodiments of the dynamic stabilization apparatus 1400, the number, the length and thickness, and the material properties of the thin sheets 1410 (or 1410') can be selected such that the longitudinal member 1408 (or 1408') exhibits a leaf spring restoring force having predetermined characteristics to resist flexion or extension of the vertebrae $V_1$ and $V_2$. For example, in one embodiment the restoring force may be directly proportional to the transverse deformation of the longitudinal member 1408 (or 1408'), e.g., with a linear spring rate, according to Hooke's law. In other embodiments, the restoring force can be a nonlinear function of the transverse deformation of the longitudinal member 1408 (or 1408'), e.g., exhibiting a nonlinear spring rate. In such a manner, the transverse stiffness of the longitudinal member 1408 (or 1408') may be predetermined to achieve the appropriate amount of dynamic stabilization of the spine.

The dynamic stabilization apparatus 1400a can also be configured so that the longitudinal member 1408a (or 1408a') exhibits desired stabilization properties under spinal loads. For example, the elastic properties of the core 1440 as well as the number, the length and the diameter, and the material properties of the array of rods 1450 (or 1450') can be selected so that the longitudinal member 1408a (or 1408a') acts as a spring with a restoring force having predetermined characteristics to resist flexion or extension of the vertebrae $V_1$ and $V_2$. Embodiments of the longitudinal members 1408a and 1408a' may be configured to exhibit a linear spring rate or a nonlinear spring rate. In certain embodiments, the longitudinal member 1408a (or 1408a') acts as a spring along the longitudinal direction and along one or more transverse directions. In certain such embodiments, the spring rate along the longitudinal direction is larger than the spring rate along a transverse direction (e.g., the member 1408a or 1408a' is stiffer longitudinally than transversely).

In certain embodiments, the longitudinal member 1408a (or 1408a') may be configured so that it is relatively inflexible along its longitudinal axis in order to provide suitable support between vertebrae. The longitudinal member 1408a (or 1408a') may be configured to have a desired range of longitudinal flexibility under compressive or tensile loads by suitably selecting, for example, elastomeric properties of the O-rings 1446a, 1446b, the length of the end space 1462, the longitudinal compressibility of the core 1440 and/or the rods 1450, etc. In some embodiments, the longitudinal member 1408a (or 1408a') is relatively flexible in directions generally transverse to the longitudinal axis of the member 1408a (or 1408a'). The longitudinal member 1408a (or 1408a') may be configured to have a range of transverse flexibility by selecting, for example, the transverse flexibility of the core 1440 and the rods 1450, the length of the end space 1462, etc. In certain embodiments, the longitudinal member 1408a (or 1408a') is relatively more flexible in one (or more) transverse directions than in the longitudinal direction.

Additionally, an advantage of certain embodiments of the longitudinal members 1408a and 1408a' is that they can be configured to exhibit flexibility in multiple dimensions. For example, the longitudinal members 1408a, 1408a' shown in FIGS. 46B-46J are capable of flexing in any direction substantially transverse to the longitudinal axis of the members 1408a, 1408a'. Accordingly, the longitudinal members 1408a, 1408a' can be configured to provide dynamic stabilization not only under forces of spinal flexion and compression (e.g., similarly as shown in FIGS. 52 and 54), but also under spinal forces acting generally transverse to the spinal axis.

The foregoing structures are useful for stabilizing at least two vertebrae of the spine of a patient. An embodiment comprises coupling a first screw with a vertebra, the first screw having a first housing. A second screw having a second housing is coupled with another vertebra. A first end of a multi-layered longitudinal member is secured with the first screw. A second end of the multi-layered longitudinal member is secured with the second screw while allowing relative motion between the layers of the longitudinal member.

In other techniques, a first cap screw is secured onto the first end of the longitudinal member to secure the longitudinal member in the first housing. A second cap screw is secured on the second end of the longitudinal member to secure the second end of the longitudinal member in the second housing while allowing relative motion between the second end of the longitudinal member and the second housing. In some embodiments, the cap screw comprises a threaded portion configured to engage the housing and a yoke that is rotatably coupled with the threaded portion and configured to engage the longitudinal member.

In other variations, the layers of the longitudinal member may comprise different materials, including, for example, titanium, titanium alloys, or other biocompatible materials. In some embodiments, the longitudinal member comprises a low friction material that is used to promote sliding between the layers and to reduce wear and to substantially prevent generation of loose debris due to the relative motion within the member. A suitable low-friction material includes ultra high molecular weight polyethylene (UHMWPE). In some embodiments, the longitudinal member has layers that alternate in composition. For example, in one embodiment the layers alternate between titanium and UHMWPE.

In some embodiments, one or both ends of the longitudinal member may be secured to the housings such that the layers may slide relative to each other and relative to the housings. In other embodiments, at least one end of the longitudinal member may be clamped to the housing such that motion of the layers relative to each other and relative to the housing is minimized. In such embodiments, the layers toward at least one end of the longitudinal member may be mechanically coupled together to prevent their relative motion, for example, by the use of rivets, welds, or adhesives.

The spinal stabilization apparatus may comprise retention members that limit the longitudinal motion of an end of the longitudinal member while allowing the layers to slide relative to each other and relative to the housing. In some embodiments, the retention members may comprise a set of notches on the longitudinal member that are mated to a set of notches on the housing or on the cap screw. The set of notches may be disposed on one or more layers of the longitudinal member.

By coupling the multi-layered longitudinal member to the vertebrae as described, the longitudinal member acts as a leaf spring that resists extension and flexion of the vertebrae to which the stabilization device is coupled, thereby imparting stability and natural stiffness to a diseased or damaged portion of the spine. The characteristics of the leaf spring such as its spring rate and stiffness may be chosen by appropriately selecting the number, the length and thickness, and the material properties of the layers. The spring rate may be linear or nonlinear.

Analogously to the procedure illustrated in FIG. 31, the spinal stabilization apparatus comprising the screws, the longitudinal member, the housings, and the cap screws may be inserted through an access device, such as the expandable conduit 20, into the operative space 90 defined at least partially by the skirt portion 24 of the expandable conduit 20.

Many variants of the method and apparatuses described above will be clear from the application. For example, the spinal stabilization apparatus may be coupled to the vertebrae with conventional pedicle screws or the fastener 600, described above. Also, the longitudinal member may be secured or clamped to the housings by use of the endoscopic screwdriver 660 or other similar device.

F. Stabilization Device Made from Flexible Material

Figure 55:
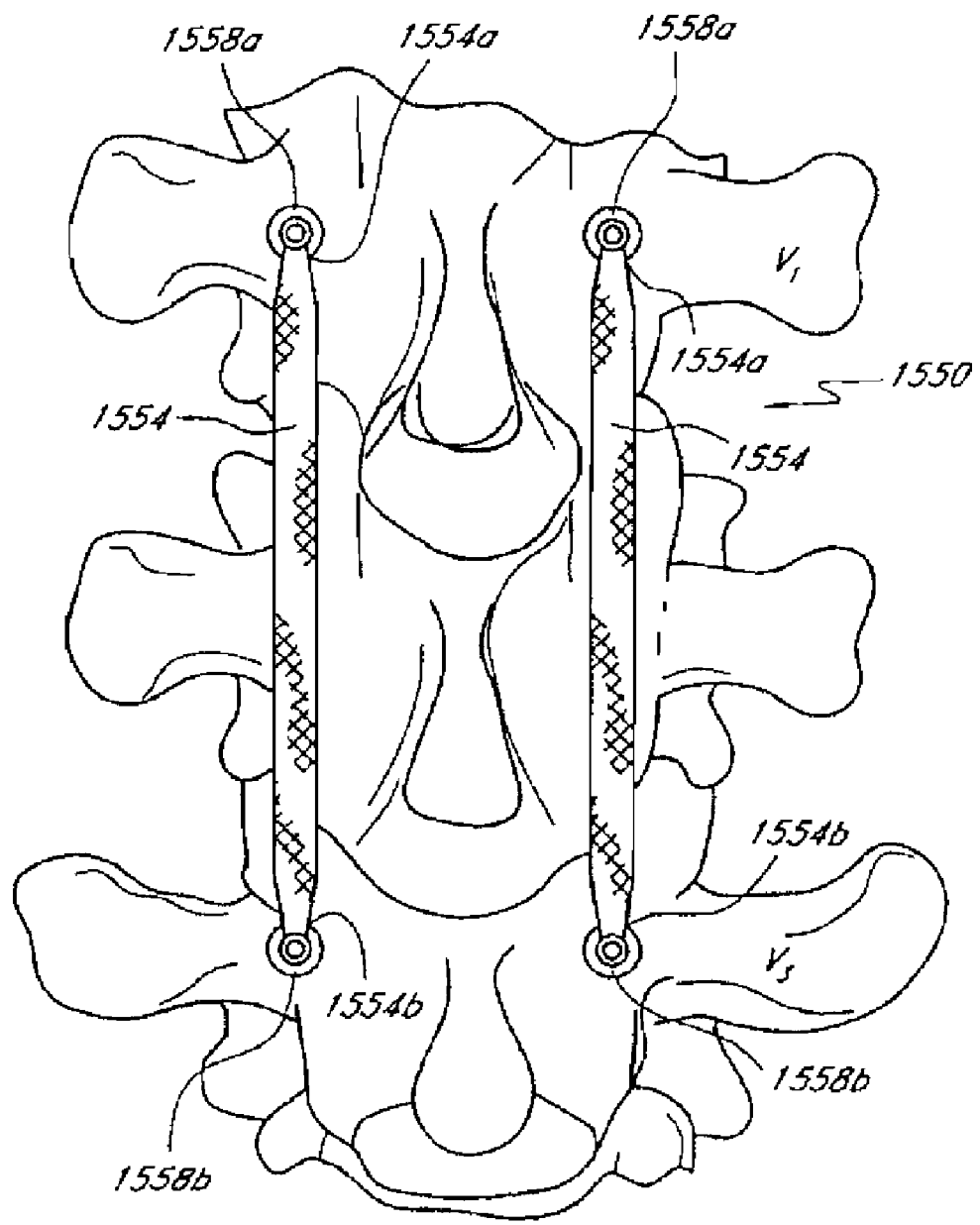
FIG. 55 is an elevation view illustrating one embodiment of a dynamic stabilization device applied to a human spine.

FIG. 55 illustrates another embodiment of a stabilization device 1550. In one embodiment, the stabilization device 1550 is configured to be secured to the posterior side of the spine. However, the device 1550 may be modified for use on the anterior or lateral sides of the spine, or at a location between the anterior and lateral sides, or at a location between the lateral and posterior sides, e.g., posterolateral.

In this embodiment of a stabilization device 1550, flexible implants 1554 are anchored to the adjacent vertebrae V1, V2 and V3. The implants 1554 preferably have a low profile and are conformable to the spinal anatomy to minimize intrusion into the surrounding tissue and vasculature. The implants 1554 attach to vertebrae and prevent separation of the vertebrae while allowing normal extension and articulation of the spinal column segment. Portions of the implants 1554 and the fasteners 1558 attaching the implant 1554 to vertebrae can be at least partially or fully embedded within the vertebrae to minimize intrusion into the surrounding tissue and vasculature.

It is contemplated that the flexible implants 1554 of the stabilization device 1550 described herein can be made from resorbable material, nonresorbable material and combinations thereof. In one example, resorbable implants 1554 can be used with interbody fusion devices since a permanent exterior stabilization may not be desired after fusion of the vertebrae. It is also contemplated that the fasteners 1558 used to attach the implants 1554 to the vertebrae can be made from resorbable material, nonresorbable material, and combinations thereof.

The implants 1554 can be flexible, tear resistant, and/or suturable. The flexible implant 1554 can also be fabricated from synthetic flexible materials in the form of fabrics, nonwoven structures, two or three dimensional woven structures, braided structures, and chained structures. The implants 1554 can also be fabricated from natural/biological materials, such as autograft or allograft, taken from patellar bone-tendon-bone, hamstring tendons, quadriceps tendons, or Achilles tendons, for example. Growth factors or cells can be incorporated into the implants 1554 for bone ingrowth and bony attachment or for soft tissue ingrowth. Possible growth factors that can be incorporated include transforming growth factor pi, insulin-like growth factor 1, platelet-derived growth factor, fibroblast growth factor, bone morphogenetic protein, LIM mineralization protein (LMP), and combinations thereof.

Possible implant materials include synthetic resorbable materials such as polylactide, polyglycolide, tyrosine-derived polycarbonate, polyanhydride, polyorthoester, polyphosphazene, calcium phosphate, hydroxyapatite, bioactive glass and combinations thereof. Possible implant materials also include natural resorbable materials such as autograft, allograft, xenograft, soft tissues, connective tissues, demineralized bone matrix, and combinations thereof. Possible implant material further include nonresorbable materials such as polyethylene, polyester, polyvinyl alcohol, polyacrylonitrile, polyamide, polytetrafluorethylene, poly-paraphenylene terephthalamide, cellulose, shape-memory alloys, titanium, titanium alloys, stainless steel, and combinations thereof.

The stabilization device 1550 described herein includes fasteners 1558 to attach the implant 1554 to the vertebrae. It is contemplated that the fasteners 1558 can be, for example, interference screws or anchors, gull anchors, suture anchors, pin fasteners, bone screws with spiked washers, staples, buttons, or bone screws such as the fastener 600 described above. It is contemplated that the fasteners 1558 can be made from resorbable materials, nonresorbable materials, and combinations thereof. Possible synthetic resorbable materials include polylactide, polyglycolide, tyrosine-derived polycarbonate, polyanhydride, polyorthoester, polyphosphazene, calcium phosphate, hydroxyapatite, bioactive glass, and combinations thereof. Possible natural resorbable materials include cortical bone, autograft, allograft, and xenograft. Possible nonresorbable materials include carbon-reinforced polymer composites, shape-memory alloys, titanium, titanium alloys, cobalt chrome alloys, stainless steel, and combinations thereof.

Referring now to FIG. 55, the stabilization device 1550 includes a flexible implant 1554 that extends along the posterior faces of vertebrae V1, V2 and V3, and is attached to a first vertebra V1 and a second vertebra V3. The flexible implant 1554 may be configured to resist extension, flexion, and/or lateral bending loads created by motion of the spinal column depending on the location or locations of the spinal column segment on which the implant 1554 is positioned.

In one embodiment, the flexible implant 1554 has a first end 1554a and an opposite second end 1554b. Vertebra V1 includes a first opening on its posterior face and a first tunnel extending therefrom. Vertebra V3 has a second opening on its posterior face and a second runnel extending therefrom. The ends 1554a and 1554b are inserted into respective ones of the first and second tunnels through these openings. An fastener 1558a is also inserted through the opening in V1, and into the tunnel of vertebra V1 to secure end 1554a to vertebra V1. Similarly, an fastener 1558b is inserted through the opening in V3, and into the tunnel of vertebra V3 to secure end 1554b to vertebra V3. Fasteners 1558a, 1558b are illustrated as threaded interference screws that are embedded into vertebral bodies V1 and V3 so that they do not protrude from the posterior faces of vertebrae V1 and V2. However, other fasteners and fastening techniques described herein could also be employed with implant 1354.

In one embodiment, the fasteners 1558a, 1558b can be oriented at an angle, alpha, with respect to the axial plane of the spinal column, in order to provide a smooth transition for implant 1554 as it enters the openings of the vertebrae V1 and V3. This reduces stress concentrations at the junction between the implant 1554 and the vertebrae. In one embodiment, angle, alpha, is about 45 degrees. Other embodiments contemplate angular orientations that range from 0 degrees to about 80 degrees and from about 25 degrees to 65 degrees.

The ends of implant 1554 and other possible implants can be provided with pigtails or other extensions of reduced size for insertion through the openings and tunnels formed in the vertebrae. It is also contemplated that the ends of the implant can include eyelets, holes, loops or other configuration suitable for engagement with an anchor. In another embodiment, not shown in the FIGURE, the implant 1554 may comprise a broad swath of material through which the fasteners 1558 are threaded to provide attachment to the underlying vertebrae.

In FIG. 55, two stabilization devices 1550 are shown extending across three vertebrae. It is further contemplated that more or fewer stabilization devices 1550 may be applied to a spine in parallel, and may extend across more or fewer vertebrae.

While the implants 1554 do not provide stress shielding against compressive loading, they do provide stabilization by resisting extension, lateral bending, and rotation. Thus, this stabilization device provides some stabilization while preserving motion between the vertebrae. Further details of structures that provide support and stability while preserving motion may be found in U.S. patent application Ser. No. 10/078,522 filed on Feb. 19, 2002, published as U.S. Patent Publication No. 2002/0120269 on Aug. 29, 2002, and U.S. patent application Ser. No. 10/083,199 filed on Feb. 26, 2002, published as U.S. Patent Publication No. 2002/0120270 on Aug. 29, 2002, which are hereby incorporated by reference in their entirety.

III. Further Methods of Applying a Stabilization Device

FIGS. 56-59 illustrate further methods of applying various types of motion preserving stabilization devices through an access device. The term "access device" is used in its ordinary sense (i.e. a device that can provide access) and is a broad term and it includes structures having an elongated dimension and defining a passage, e.g., a cannula or a conduit. These and similar methods also can be used to deliver any suitable stabilization device, including those hereinbefore described. Also, some aspects of these methods may be similar to or combinable with the methods described above in connection with the application of single or multi-level fixation devices.

Figure 56:
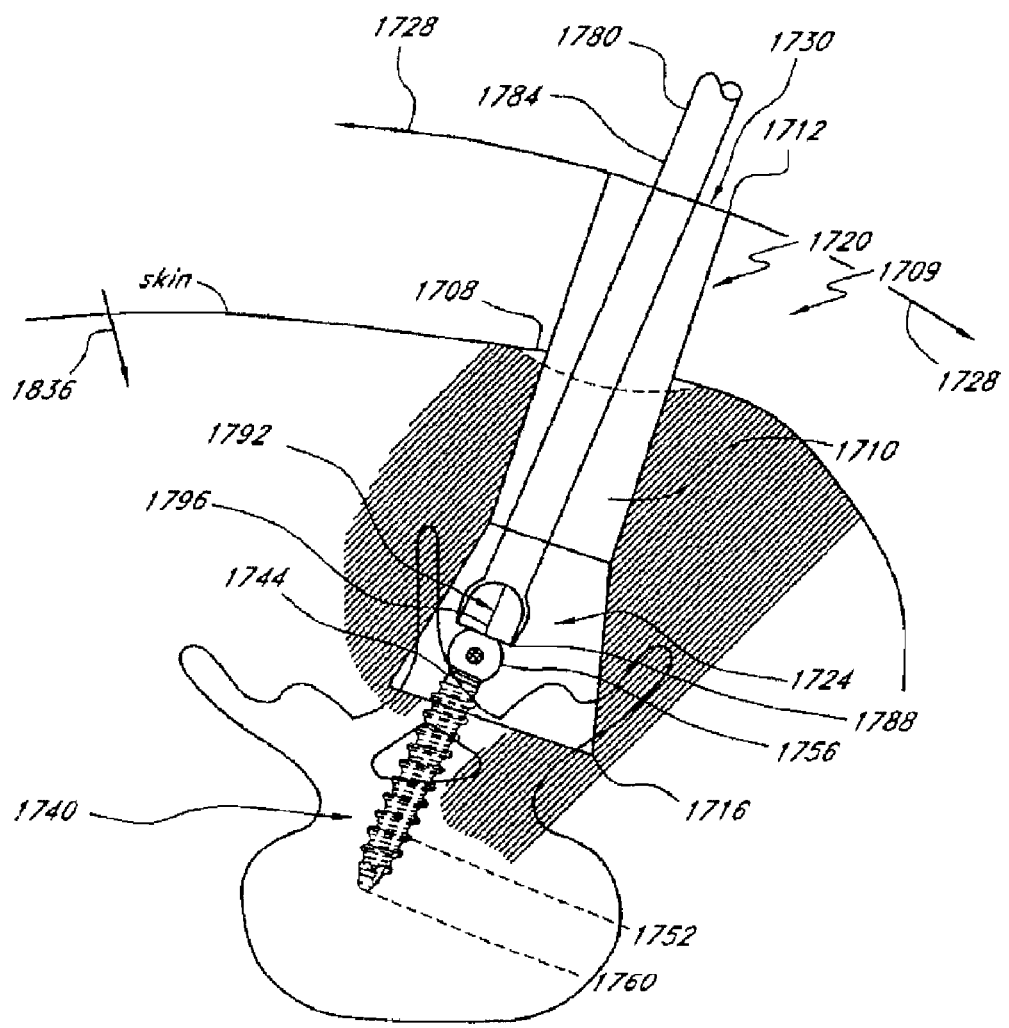
FIG. 56 is a schematic view of one embodiment of an access device applied through the skin of a patient to provide access to a surgical location near the spine in connection with a dynamic stabilization procedure.

FIG. 56 shows that in one method, an access device 1704 is advanced through an incision 1708 in the skin and is further advanced to a surgical location adjacent the spine of the patient. The term "surgical location" is used in its ordinary sense (i.e. a location where a surgical procedure is performed) and is a broad term and it includes locations subject to or affected by a surgery. The term "spinal location" is used in its ordinary sense (i.e. a location associated with a spine) and is a broad term and it includes locations near a spine that are sites for surgical spinal procedures. The access device 1704 may be advanced generally posteriorly. The terms "posterior" and "posteriorly" are used in their ordinary sense (i.e., from or through the rear-facing side of the patient) and are broad terms and they include an approach along any line generally behind and between the two lateral sides of the patient. In the illustrated embodiment, the access device 1704 is advanced along a generally postero-lateral approach and is positioned above a portion of the spine. In one application, the access device 1704 is positioned above at least one pedicular area of at least one of two adjacent vertebrae. In another application, the access device 1704 may be positioned above one or more pedicular areas of more than two adjacent vertebrae.

The access device 1704 may be similar to those described above, e.g., the expandable conduit 20, except as set forth below. The access device 1704 preferably has an elongate body 1710 that extends between a proximal end 1712 and a distal end 1716. The elongate body 1710 has a length between the proximal end 1712 and the distal end 1716 that is selected such that when the access device 1704 is applied to a patient during a surgical procedure, e.g., as shown in FIGS. 56-59, the distal end 1716 can be positioned inside the patient adjacent a spinal location. When so positioned, the selected length of the elongate body 1710 is such that the proximal end 1712 is located outside the patient at a suitable height.

In one embodiment, the elongate body 1710 comprises a proximal portion 1720 and a distal portion 1724. The proximal portion 1720 may have a generally oblong, oval, circular, or other suitable shape. The term "oblong" is used in its ordinary sense (i.e. having an elongated form) and is a broad term and it includes a structure having a dimension, especially one of two perpendicular dimensions, such as, for example, width or length, that is greater than another. The term "oval" is used in its ordinary sense (i.e., egg like or elliptical) and is a broad term and includes oblong shapes having curved portions and oblong shapes having parallel sides and curved portions. The access device 1704 may further have a circular cross-section near the proximal end 1712, near the distal end 1716, at the proximal and distal ends 1712, 1716, and from the proximal end 1712 to the distal end 1716. As discussed above, in another embodiment, the access device 1704 has an oblong cross-sectional shape in the proximal portion 1720. In particular, the access device 1704 may have an oblong cross-section near the proximal end 1712, near the distal end 1716, at the proximal and distal ends 1712, 1716, and from the proximal end 1712 to the distal end 1716.

The access device 1704 preferably is capable of having a first configuration for insertion to the surgical location over the two vertebrae, which may be a relatively low-profile configuration, and a second configuration wherein increased access is provided to the surgical space. In the second configuration, the distal end 1716 may have a cross-sectional area that is larger than that of the first configuration at the distal end 1716. The distal portion 1724 of the access device 1704 may be expanded from the first configuration to the second configuration using an expander apparatus, such as the expander apparatus 200, as discussed above in connection with the skirt portion 24. When so expanded, the distal portion 1724, at the distal end 1716, defines a surgical space that includes a portion of at least one vertebra, and preferably two adjacent vertebrae.

The proximal and distal portions 1720, 1724 preferably are pivotally coupled to each other, as indicated by the arrows 1728 in FIG. 56. The arrows 1728 indicate that the proximal portion 1720 may be pivoted medially and laterally with respect to the distal portion 1724. This pivotal motion tends to expose to a greater extent medial and lateral portions of the surgical space defined within the perimeter of the distal end 1716 of the access device 1704. In particular, pivoting the proximal portion 1720 laterally with respect to the distal portion 1724 exposes a portion of one or more vertebrae (or a portion of an external surface of an annulus A of an intervertebral disc) generally closer to the midline of the spine. Similarly, pivoting the proximal portion 1720 medially with respect to the distal portion 1724 exposes a portion of one or more vertebrae (or a portion of an external surface of the annulus A) generally closer to the transverse processes of the vertebrae.

In a like manner, as discussed further below, pivotal motion can be provided in the cephalad-caudal direction to expose generally cephalad or generally caudal peripheral portions of the surgical space defined within the perimeter of the distal end 1716.

At least one passage 1730 extends through the elongate body 1710 between the proximal end 1712 and the distal end 1716. The passage 1730 provides visualization of the surgical space in any suitable manner, e.g., by a viewing element, as discussed above. The passage 1730 also can provide sufficient access to the surgical space, e.g., adjacent the spine, such that components of a wide variety of dynamic stabilization systems, as well as implements adapted to deliver and apply such components, may be passed therethrough to the surgical location.

Figure 57:
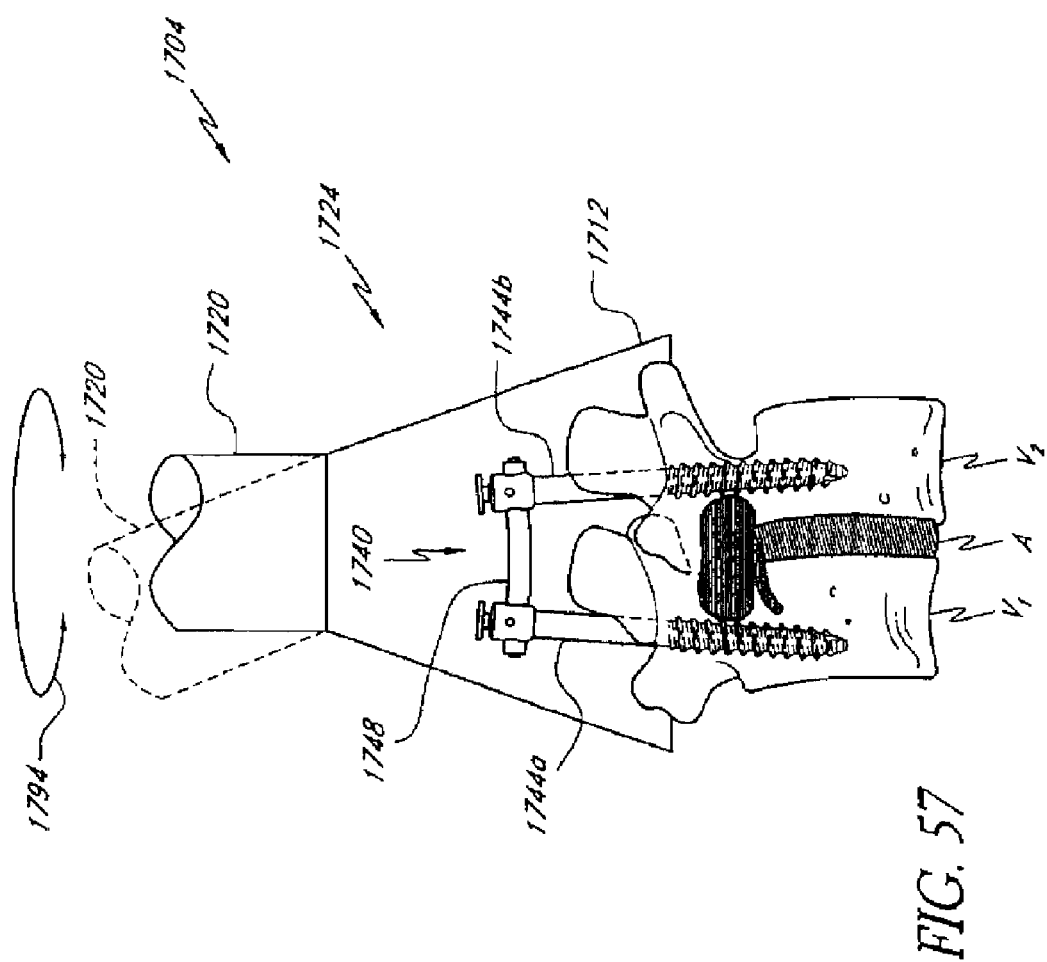
FIG. 57 is a lateral view of two adjacent vertebrae of the spine to which the access device of FIG. 56 has been applied, illustrating the application of one embodiment of a dynamic stabilizer.

As discussed above, in the method illustrated by FIG. 56, the distal end 1716 of the access device 1704 may be inserted postero-laterally, to a surgical location adjacent to at least one vertebra and preferably adjacent to the first vertebra $V_1$ and the second vertebra $V_2$ (See FIG. 57). Insertion of the access device 1704 may be facilitated by first delivering a series of dilators, as discussed above in connection with the expandable conduit 20. In one application, as discussed above, after the access device 1704 has been delivered, it can be expanded to the second configuration, as indicated schematically in FIG. 56. Further details of various additional embodiments of the access device 1704 may be found in U.S. patent application Ser. No. 10/678,744, filed Oct. 2, 2003, entitled MINIMALLY INVASIVE ACCESS DEVICE AND METHOD, published as U.S. Patent Application No. 2005/0075540 on Apr. 7, 2005, which is hereby incorporated by reference herein in its entirety.

After the access device 1704 is delivered, a stabilization device 1740 is applied to the patient. In one embodiment, the stabilization device 1740 is configured to stabilize at least two adjacent vertebrae while preserving a degree of motion. The term "dynamic stabilization" is used in its ordinary sense (i.e., stabilizing adjacent vertebrae while permitting some degree of motion) and is a broad term and it includes stabilization that allows movement on a macroscopic or a microscopic level between adjacent vertebrae. The term "motion preserving" or "motion preservation" are used in their ordinary senses (i.e., maintaining the ability for motion or movement) and is a broad term and it includes restoring at least some motion that had been lost due to spinal conditions. In one embodiment, the stabilization device 1740 includes a fastener, e.g., a bone anchor 1744, to be secured to each vertebra $V_1$, $V_2$ and a connecting element 1748 configured to couple with the bone anchors 1744 and to extend between the adjacent vertebrae and to preserve motion of the adjacent vertebrae with respect to each other. The bone anchor 1744 may be a screw that is similar to a standard pedicle screw or may be similar to the fastener 600. In one embodiment, the bone anchor 1744 has an elongate body 1752 that extends between a proximal end 1756 and a distal end 1760. The distal end 1760 preferably is configured to engage bone, e.g., a vertebrae, in a suitable manner. In one embodiment, threads extend proximally from the distal end 1760. The proximal end 1756 of the bone anchor 1744 is configured to reside a suitable height above a vertebra when the bone anchor 1744 is applied thereto and to couple with the connecting element 1748 in a suitable manner, e.g., in a manner similar to the coupling between the elongated member 650 and the fastener 600.

The stabilization device 1740 is configured to allow movement, on a macroscopic or a microscopic level, between adjacent vertebrae to which it is applied. In one embodiment, the connecting element 1748 is configured such that motion is permitted at the point at which the connecting element 1748 is coupled with the bone anchor 1744 (See FIG. 38). In another embodiment, the connecting element 1748 is configured such that movement is allowed at a location between two adjacent bone anchors 1744 applied to two adjacent vertebrae (See FIG. 42).

In one application, the bone anchor 1744 is advanced through the proximal end 1712 of the access device 1704, through the passage 1730, and to the surgical location defined by the distal portion 1724 of the access device 1704. Thereafter, the bone anchor 1744 is advanced into a portion of a bone, e.g., into a pedicle of a vertebra which is to be dynamically stabilized.

Prior to insertion of the stabilization device 1740, surgical tools may be delivered through the access device 1704 to prepare the vertebrae $V_1$, $V_2$ to receive the bone anchors 1744. In various methods, bone probes, taps, or sounders may be inserted through the access device 1704 in order to perform procedures, e.g., drill and tap holes in the pedicle structures. Sounders may be used to assess the integrity of the portion of the vertebra or other bone where the bone anchor 1744 is to be applied. Bone probes may be used to make the initial invasion into the bone. Taps may be used to thread a hole or to create a threaded hole in the bone into which a bone anchor 1744 may be advanced. Any other useful instruments or preparatory procedures known to those skilled in the art may also be used in various applications. These instruments preferably have lengths chosen such that when they are inserted through the access device 1704 to the surgical space, their proximal ends extend proximally of the proximal end 1712 of the access device 1704. This arrangement permits the surgeon to manipulate these instruments proximally of the access device 1704.

The bone anchor 1744 may be advanced by any suitable implant insertion tool, e.g., a bone anchor insertion tool 1780. In one embodiment, the bone anchor insertion tool 1780 is an elongate body 1784 that extends from a proximal end (not shown) configured to be grasped, e.g., manually by the surgeon, to a distal end 1788 and defines a length therebetween. The length of the elongate body 1784 is selected such that when the bone anchor insertion tool 1780 is inserted through the access device 1704 to the surgical space, the proximal end extends proximally of the proximal end 1712 of the access device 1704. This arrangement permits the surgeon to manipulate the bone anchor insertion tool 1780 proximally of the access device 1704.

The distal end 1788 is configured to engage the proximal end 1756 of the bone anchor 1744. For example, the distal end 1788 may have a cavity 1792 shaped to receive the proximal end 1756 of the bone anchor 1744. In one embodiment, the cavity 1792 engages the proximal end 1756 of the bone anchor 1744 in a manner to enable the bone anchor 1744 to be advanced, e.g., by transferring torsion applied to the proximal end of the bone anchor tool 1780 to the bone anchor 1744, into the pedicle or other bone segment. In another embodiment, the bone anchor insertion tool 1780 has a grip portion configured to engage the bone anchor 1744. In one embodiment, both the grip portion and the bone anchor 1744 are hexagonal and are configured such that the width of the proximal end of the bone anchor 1744 is slightly less than the width of the grip portion. Other means of coupling the bone anchor insertion tool 1780 to the bone anchor 1744 that permit the bone anchor 1744 to be inserted through the access device 1704 could also be used.

As discussed above, in one embodiment, the access device 1704 provides pivotal motion between the proximal and distal portions 1720, 1724, as indicated by the arrows 1728. This pivotal motion enables the bone anchor 1744 to be applied within a range of angles with respect to the mid-plane of the spine. This enables the surgeon to select a preferred orientation of the bone anchor 1744 with respect to the vertebrae or other bone segment.

After the desired orientation of the bone anchor 1744 has been selected and the bone anchor 1744 has been advanced into the vertebra, as indicated in FIG. 56, the bone anchor insertion tool 1780 may be disengaged from the proximal end 1766 of the bone anchor 1744 and withdrawn from the access device 1704, as indicated by the arrow 1796.

FIG. 57 shows that in one application, the access device 1704 is configured to extend between two adjacent vertebrae $V_1$, $V_2$ and to provide access to at least a portion of a pedicle of each of the vertebrae $V_1$, $V_2$ at the same time. In this manner, a first bone anchor 1744a may be applied to the first vertebra $V_1$ and a second bone anchor 1744b may be applied to the second vertebra $V_2$ (which may be superior or inferior to the first vertebra $V_1$) without the need to repeat the steps of inserting the access device 1704 over each vertebra to provide access to the pedicles thereof. Two separate access devices may be used to access the pedicles of adjacent vertebrae or one access device may be inserted twice, once over each of the adjacent vertebra. Further variations and combination are also possible, e.g., one or two access device may be applied on each side of the mid-line of the spine to access three adjacent vertebrae so that a multi-level dynamic stabilization device may be applied to couple three adjacent vertebrae. These procedures may be repeated on each side of the mid-line of the spine to apply multi-level dynamic stabilization devices on each side thereof.

An arrow 1794 in FIG. 57 indicates that the proximal portion 1720 may be pivoted with respect to the distal portion 1724 to provide access to the peripheral regions of the surgical space defined by the distal end 1712 of the access device 1704. This arrangement may simplify or facilitate the insertion of the bone anchors 1744a, 1744b.

Once the bone anchors 1744a, 1744b are applied to the patient, the connecting element 1748 may be advanced into the proximal end 1712 of the access device 1704, through the passage 1730, to the surgical location. Once at the surgical location, the connecting element 1748 may be coupled with the bone anchors 1744a, 1744b in a suitable manner. As discussed above, one arrangement preserves motion of the vertebrae $V_1$, $V_2$ by permitting movement at or near the coupling of one or both of the connecting element 1748 and the bone anchors 1744. Another arrangement preserves motion of the vertebrae $V_1$, $V_2$ by permitting movement at a location between the bone anchors 1744a, 1744b. Another arrangement preserves motion of the vertebrae $V_1$, $V_2$ by permitting movement both at or near the connecting element/bone anchor coupling(s) and at a location between the bone anchors 1744a, 1744b.

Figure 58:
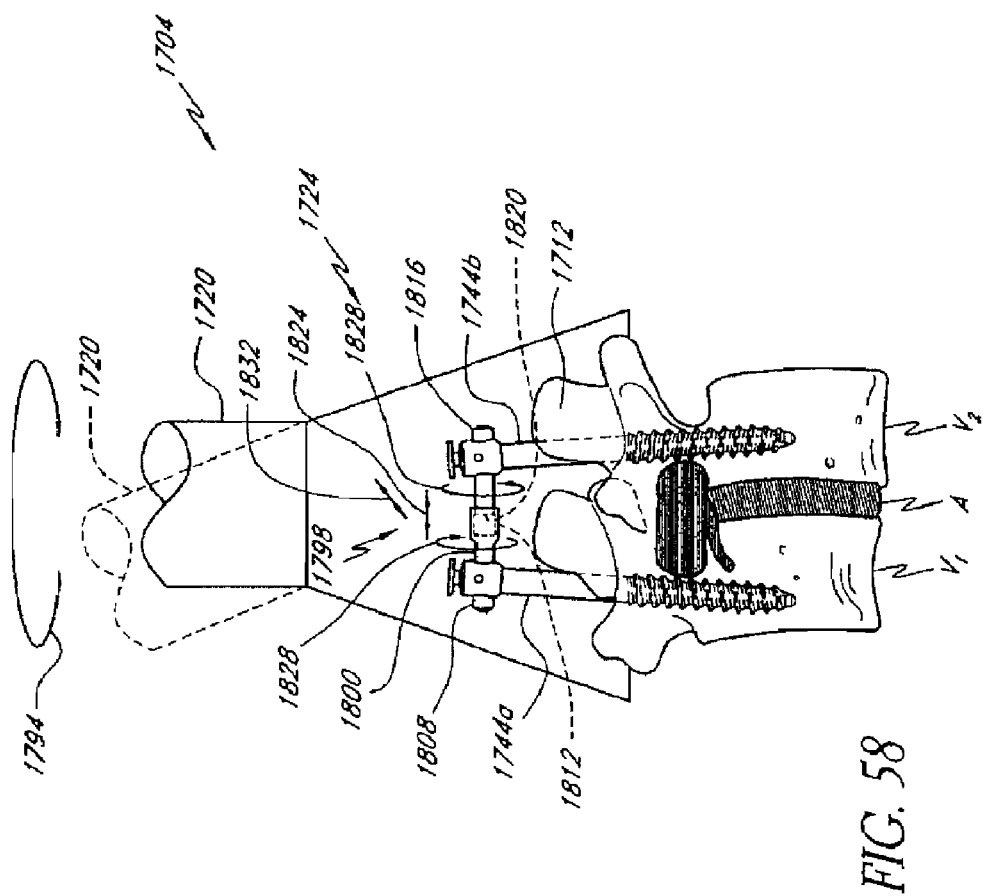
FIG. 58 is a lateral view of two adjacent vertebrae of the spine to which the access device of FIG. 56 has been applied, illustrating the application of another embodiment of a dynamic stabilizer.

In one embodiment, the connecting element 1748 is a flexible member that permits a degree of motion between the vertebrae $V_1$, $V_2$. FIG. 58 shows another embodiment of a connecting element 1798 that is a dynamic connecting element, e.g., an element that is configured such that movement is allowed at a location along the connecting element 1798 at a location between two adjacent bone anchors 1744 applied to two adjacent vertebrae (See FIG. 42). In one embodiment, the connecting element 1798 has a first member 1800 coupled with the first bone anchor 1744a, and thereby with the first vertebra $V_1$, and a second member 1804 coupled with the second bone anchor 1744b, and thereby coupled with the second vertebra $V_2$. The first and second members 1800, 1804 may be rigid members or they may be flexible. The first member 1800 has a first end 1808 configured to couple with the first bone anchor 1744a and a second end with a chamber 1812 formed therein. The second member 1804 has a first end 1816 configured to couple with the second bone anchor 1744b and a second end with a piston 1820 arranged thereon. When the connecting element 1798 is assembled, the piston 1820 is arranged to move within the chamber 1812, providing motion indicated by an arrow 1824. The coupling of the piston 1820 and the chamber 1812 could also permit rotational motion of the first and second members 1800, 1804 as indicated by arrows 1828. The piston and chamber arrangement could be configured to permit a degree of pivoting of the first member 1800 with respect to the second member 1804, as indicated by an arrow 1832. Other arrangements of connecting elements could employ spring mechanisms, ball-and-socket joints, or any of the other geometries or arrangements described hereinabove.

The access device 1704 is advantageously configured to permit the foregoing steps to be performed in any order. For example, the connecting elements 1748, 1798 may be advanced to the surgical location before or after the first bone anchor 1744a is applied to the first vertebra $V_1$. In a like manner, the connecting elements 1748, 1798 may be advanced to the surgical location before the second bone anchor 1744b is applied to the second vertebra $V_2$. The connecting element 1748, 1798 may further be coupled with the first bone anchor 1744a before the second bone anchor 1744b is applied to the second vertebra $V_2$. Other orders of the foregoing steps are also possible.

In one procedure, once the bone anchors 1744 have been attached to the two adjacent vertebrae $V_1$, $V_2$, the connecting element 1748, 1798 may be delivered through the access device 1704 to couple with the bone anchors 1744. To facilitate insertion, a gripping apparatus, such as, e.g., the guide apparatus 800 described above, may be used to engage the connecting element 1748, 1798 and manipulate it through the access device 1704 to the surgical space. The connecting elements 1748, 1798 may take many forms depending on the particular stabilization device being delivered and the combination of vertebrae being treated.

In one embodiment, shown in FIG. 57, the connecting element 1748 is a flexible member, such as that described above for stabilization device 1400. In another embodiment, shown in FIG. 58, the connecting element 1798 may comprise a jointed link rod, such as that described above for stabilization device 1450.

Once the connecting element 1748, 1798 is appropriately seated on or near the bone anchors 1744, clamping elements may be inserted through the access device 1704 in a manner similar to that described above. The clamping elements may then be threadably or otherwise engaged with the bone anchors 1744, fixing the connecting element 1748, 1798 between the clamping element and the bone anchors 1744.

In some applications, a second access device, such as an expandable conduit 20 or other suitable access device, may be inserted into the patient. For example, a second access device could be inserted through a postero-lateral approach on the contralateral side of the spine, e.g., the opposite side of the spine across the mid-line of the spine, as indicated by an arrow 1836, to provide access to at least one of two or more adjacent vertebrae. In another embodiment, a second access device may be inserted through an alternative approach on the same or opposite side of the spine to provide access to at least one of two or more adjacent vertebrae. This second access device may provide access to the vertebrae at about the same time as the first access device 1704 or during a later or earlier portion of a procedure. In one method, two stabilization devices are inserted from both sides of the spine using first and second access devices. Any combination of single, multiple stabilization devices, or stabilization device sub-components may be delivered through one or more access devices from any combination of one or more approaches, such as the approaches shown in FIGS. 56-59, or any other suitable approach.

Figure 59:
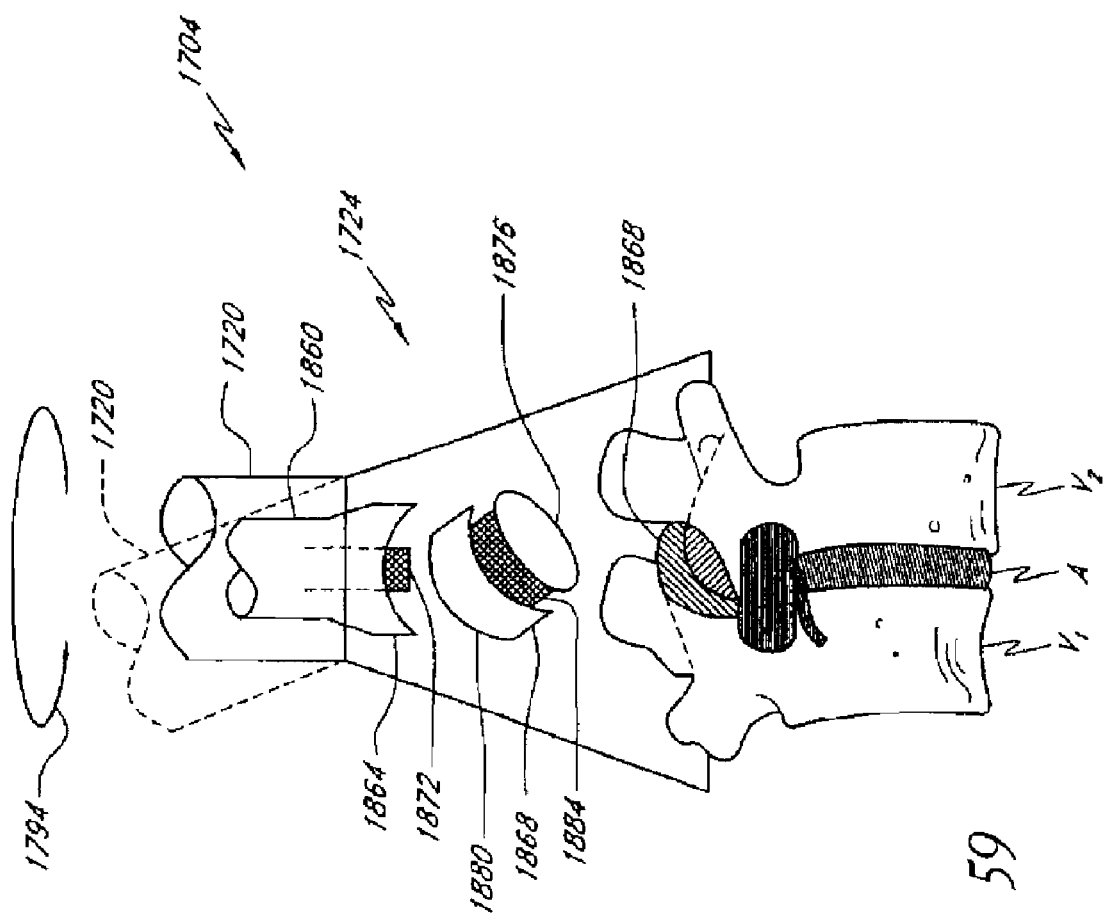
FIG. 59 is a lateral view of two adjacent vertebrae of the spine to which the access device of FIG. 56 has been applied, illustrating the application of another embodiment of a dynamic stabilizer.

FIG. 59 shows schematically another form of a dynamic stabilization treatment that could be provided through the access device 1704. In this treatment, one or more facet joints are removed and one or more artificial facet joints are inserted in their place. As above, the access device 1704 is delivered to the surgical location and is configured to provide access to a surgical location.

The facet joint may be removed using any suitable technique. Preferably, the facet joint is removed by inserting one or more implements to the surgical location through the access device 1704 and withdrawing facet joint fragments from the surgical location through the access device 1704.

After the facet joint is removed, a facet joint insertion tool 1860 may be advanced into the access device 1704 and may be advanced through the passage 1730 to a location adjacent where the natural facet joint had been.

The facet joint insertion tool 1860 preferably has an elongate body with a proximal end (not shown) that is configured to be manipulated by a surgeon and a distal end 1864 that is configured to selectively engage an artificial facet joint configured to preserve motion of the vertebrae forming the face joint. One such artificial face joint is the replacement facet joint 1868. Preferably the distal end 1864 includes a releasable clamp 1872 or other means for engaging the facet joint. In one embodiment, the clamp 1872 is releasable at the proximal end of the facet joint insertion tool.

The replacement facet joint 1868 preferably includes a generally superior member 1876, a generally inferior member 1880, and a connecting member 1884 that is positioned between the superior member 1876 and the inferior member 1880. The superior member 1876 is configured to engage the generally superior aspect of the facet portion of the vertebra $V_1$. The inferior member 1880 is configured to engage the generally inferior aspect of the facet portion of the vertebra $V_2$. In one embodiment, bone growth features are provided on the surfaces of the superior and inferior members 1876, 1880 that are intended to engage the vertebral surfaces facing the facet joint. Although the bone growth features are shown as spikes in the illustrated embodiment, they may take any other suitable form. The connecting member 1884 is a deformable member in one embodiment that permits movement of the facets of the vertebrae $V_1$, $V_2$ with respect to each other to provide dynamic stabilization of the vertebrae $V_1$, $V_2$.

FIG. 59 illustrates at least two stages of a method for implanting replacement facet joint by way of the access device 1704 to provide dynamic stabilization. In one stage, when the replacement facet joint 1868 has been advanced to the surgical location, the facet joint insertion tool 1860 is caused to release the replacement facet joint 1868. This stage is represented by the schematic depiction of the replacement facet joint 1868 located between the distal end of the facet joint insertion tool 1860 and the vertebrae $V_1$, $V_2$. In another stage, the replacement facet joint 1868 is coupled with the adjacent vertebrae $V_1$, $V_2$ to form a replacement joint, as shown by the dashed outline of a replacement facet joint in positioned where the natural facet joint had been.

The proximal portion 1720 of the access device 1704 is pivotal with respect to the distal portion 1724 thereof, as illustrated by the dashed line representation of the proximal portion 1720 and the arrow 1794, as discussed above. This may facilitate one or more of the foregoing steps of facet joint replacement dynamic stabilization.

Although the forgoing procedures are described in connection with a single level postero-lateral procedure, other procedures are possible. For example, multiple level stabilization could be performed with the expandable conduit 20 or other suitable access device as described above with reference to FIGS. 30-37. As discussed above, other applications are also possible in which the access device 1704 is not expanded prior to delivery of the stabilization device 1700. In such applications, the access device 1704 remains in the first configuration while some, all, or any of the steps described above are performed. Also, a motion preserving stabilization procedure could be combined with various spinal procedures used to partially fuse or rigidly fix adjacent vertebrae for stabilization along any suitable approach, e.g., anterior, lateral, posterior, transforaminal.

Although the methods discussed above are particularly directed to the insertion of a stabilization device, the access device 1704 may also be used advantageously to extract or remove the stabilization device. The surgical tools also may be further configured to facilitate removal as well as insertion. In one application, a motion preserving stabilization device may be replaced with a generally inflexible stabilization device, such as those described above, through the access device 1704. In another application, a previously inserted generally inflexible stabilization device may be replaced with a motion preserving stabilization device, such as those described above, through the access device 1704.

The foregoing methods and apparatuses advantageously provide minimally invasive treatment of a person's spine in a manner that preserves some degree of motion between the vertebrae. Accordingly, trauma to the patient may be reduced thereby, and recovery time shortened. As discussed above, the stabilization devices described herein provide a more normal post-recovery range of motion of the spine, which can reduce the need for additional procedures.

It will be understood that the foregoing is only illustrative of the principles of the invention, and that various modifications, alterations, combinations, and equivalents can be made by those skilled in the art without departing from the scope and spirit of the invention.

What is claimed is:

1. A stabilization system for a spinal column, the stabilization system comprising:
    a first vertebral fastener configured to be engaged with a first vertebra, the first vertebral fastener including a housing and a threaded shank extending from the housing, the housing of the first vertebral fastener including a channel extending from a first side of the housing to a second side of the housing;
    a second vertebral fastener configured to be engaged with a second vertebra, the second vertebral fastener including a housing and a threaded shank extending from the housing, the housing of the second vertebral fastener including a channel extending from a first side of the housing to a second side of the housing;
    a longitudinal member having a first end and a second end, the longitudinal member configured to extend between the housing of the first vertebral fastener and the housing of the second vertebral fastener;
    the longitudinal member comprising a plurality of thin sheets configured to slide relative to one another to impart a degree of lateral flexibility on the longitudinal member;
    a first clamping device configured to engage the housing of the first vertebral fastener to fasten the longitudinal member in the channel of the housing of the first vertebral fastener; and
    a second clamping device configured to engage the housing of the second vertebral fastener to fasten the longitudinal member in the channel of the housing of the second vertebral fastener.

2. The stabilization system of claim 1, wherein the plurality of thin sheets are mechanically coupled together proximate the first end of the longitudinal member to limit relative motion between the plurality of thin sheets proximate the first end of the longitudinal member.

3. The stabilization system of claim 1, wherein the first clamping device secures the longitudinal member in the channel of the housing of the first vertebral fastener such that at least some of the plurality of thin sheets are permitted to slide relative to each other.

4. The stabilization system of claim 3, wherein the second clamping device secures the longitudinal member in the channel of the housing of the second vertebral fastener.

5. The stabilization system of claim 3, wherein the second clamping device clamps the longitudinal member in the channel of the housing of the second vertebral fastener to rigidly connect a portion of the longitudinal member to the housing of the second vertebral fastener.

6. The stabilization system of claim 1, wherein a first thin sheet of the plurality of thin sheets comprises a first material and a second thin sheet of the plurality of thin sheets comprises a second material different from the first material.

7. The stabilization system of claim 6, wherein the first material is substantially incompressible along a longitudinal axis of the longitudinal member.

8. The stabilization system of claim 7, wherein the second material comprises a low-friction material.

9. The stabilization system of claim 1, wherein at least a portion of the plurality of sheets is coated with a low-friction material.

10. The stabilization system of claim 1, wherein the second clamping device includes an interlocking feature interlocking with an interlocking feature of the longitudinal member when the second clamping device is engaged with the housing of the second vertebral fastener while allowing the plurality of thin sheets to slide relative to each other and relative to the housing of the second vertebral fastener.

11. A stabilization system for a spinal column, the stabilization system comprising:
a first vertebral fastener configured to be engaged with a first vertebra, the first vertebral fastener including a housing and a threaded shank extending from the housing, the housing of the first vertebral fastener including a channel extending from a first side of the housing to a second side of the housing;
a second vertebral fastener configured to be engaged with a second vertebra, the second vertebral fastener including a housing and a threaded shank extending from the housing, the housing of the second vertebral fastener including a channel extending from a first side of the housing to a second side of the housing;
a longitudinal member having a first end and a second end, the longitudinal member configured to extend between the housing of the first vertebral fastener and the housing of the second vertebral fastener;
the longitudinal member comprising a plurality of elongated load-bearing elements arranged in an array, the array of elongated load-bearing element configured to resist axial elongation and compression of the longitudinal member while allowing lateral flexing of the longitudinal member when subjected to spinal loads;
a first clamping device configured to engage the housing of the first vertebral fastener to fasten the longitudinal member in the channel of the housing of the first vertebral fastener; and
a second clamping device configured to engage the housing of the second vertebral fastener to fasten the longitudinal member in the channel of the housing of the second vertebral fastener.

12. The apparatus of claim 11, wherein the array of elongated load-bearing elements comprises a linear array.

13. The apparatus of claim 11, wherein the elongated load-bearing elements comprise sheets.

14. The apparatus of claim 13, wherein the sheets are stacked adjacent one another.

15. The apparatus of claim 14, wherein the sheets are moveable relative to one another in a longitudinal direction.

16. The apparatus of claim 11, wherein the array of elongated load-bearing elements comprises a cylindrical array.

17. The apparatus of claim 11, wherein the elongated load-bearing elements comprise axial rods.

18. The apparatus of claim 17, wherein the axial rods are arranged in a cylindrical array around a core element of the longitudinal member.

* * * * *

UNITED STATES PATENT AND TRADEMARK OFFICE
CERTIFICATE OF CORRECTION

| | |
|---|---|
| PATENT NO. | : 8,016,828 B2 |
| APPLICATION NO. | : 12/651808 |
| DATED | : September 13, 2011 |
| INVENTOR(S) | : Alan Shluzas |

Page 1 of 1

It is certified that error appears in the above-identified patent and that said Letters Patent is hereby corrected as shown below:

Column 14
Line 3, delete "min", and insert therefore -- mm --.

Column 27
Line 61, delete "fanned", and insert therefore -- formed --.

Signed and Sealed this
First Day of November, 2011

David J. Kappos
*Director of the United States Patent and Trademark Office*